US012799200B2

(12) United States Patent
Zhou et al.

(10) Patent No.: US 12,799,200 B2
(45) Date of Patent: Nov. 17, 2026

(54) IMMUNE CELL EXPRESSING A CHIMERIC ANTIGEN RECEPTOR TARGETING CD7 AND HAVING SUPPRESSED OR SILENCED EXPRESSION OF TCR/CD3- AND MHC-II-RELATED-GENES AND METHOD OF USE THEREOF FOR TREATMENT

(71) Applicant: IMVIVABIO LLC, Boston, MA (US)

(72) Inventors: Yali Zhou, Nanjing (CN); Xiaoyan Jiang, Nanjing (CN); Gong Chen, Nanjing (CN); Jiangtao Ren, Nanjing (CN); Xiaohong He, Nanjing (CN); Yanbin Wang, Nanjing (CN); Lu Han, Nanjing (CN)

(73) Assignee: IMVIVABIO LLC, Boston, MA (US)

( * ) Notice: Subject to any disclaimer, the term of this patent is extended or adjusted under 35 U.S.C. 154(b) by 709 days.

(21) Appl. No.: 18/034,177

(22) PCT Filed: Oct. 29, 2021

(86) PCT No.: PCT/CN2021/127567

§ 371 (c)(1),
(2) Date: Apr. 27, 2023

(87) PCT Pub. No.: WO2022/095802

PCT Pub. Date: May 12, 2022

(65) Prior Publication Data

US 2023/0390336 A1 Dec. 7, 2023

(30) Foreign Application Priority Data

Nov. 3, 2020 (CN) ........................ 202011209352.X

(51) Int. Cl.

| | |
|---|---|
| ***C07K 16/28*** | (2006.01) |
| ***A61K 40/11*** | (2025.01) |
| ***A61K 40/15*** | (2025.01) |
| ***A61K 40/24*** | (2025.01) |
| ***A61K 40/31*** | (2025.01) |
| ***A61K 40/42*** | (2025.01) |
| ***A61P 35/02*** | (2006.01) |
| ***C12N 5/0783*** | (2010.01) |

(52) U.S. Cl.

CPC .......... *C07K 16/2803* (2013.01); *A61K 40/11* (2025.01); *A61K 40/15* (2025.01); *A61K 40/24* (2025.01); *A61K 40/31* (2025.01); *A61K 40/421* (2025.01); *A61K 40/4211* (2025.01); *A61K 40/4254* (2025.01); *A61P 35/02* (2018.01); *C12N 5/0636* (2013.01); *A61K 2239/13* (2023.05); *A61K 2239/28* (2023.05); *A61K 2239/29* (2023.05); *A61K 2239/48* (2023.05)

(58) Field of Classification Search

CPC .......... C07K 16/2803; C07K 2317/622; C07K 2317/73; C07K 2317/76; C07K 2317/565; C07K 14/70503; C07K 14/7051; C07K 14/70539; C07K 14/70548; C07K 2319/03; C07K 2319/33; C07K 2319/02; C07K 2319/74; A61K 40/11; A61K 40/15; A61K 40/24; A61K 40/31; A61K 40/421; A61K 40/4211; A61K 40/4254; A61K 40/50; A61K 40/30; A61K 40/36; A61K 40/4224; A61K 2239/13; A61K 2239/28; A61K 2239/29; A61K 2239/48; A61P 35/02; A61P 35/00; C12N 5/0636; C12N 2510/00; C12N 2501/505; C12N 2501/515; C12N 2740/13043; C12N 2740/16043

See application file for complete search history.

(56) References Cited

U.S. PATENT DOCUMENTS

| | | | |
|---|---|---|---|
| 2016/0009813 | A1 | 1/2016 | Themeli et al. |
| 2020/0087398 | A1 | 3/2020 | Qasim et al. |

FOREIGN PATENT DOCUMENTS

| | | | |
|---|---|---|---|
| CN | 109694854 | A | 4/2019 |
| CN | 109996811 | A | 7/2019 |
| CN | 107723275 | A | 9/2020 |
| CN | 110760007 | A | 8/2022 |
| EP | 3699268 | A1 | 8/2020 |
| JP | 2019536480 | A | 12/2019 |
| JP | 2020513832 | A | 5/2020 |
| JP | 2020519277 | A | 7/2020 |
| WO | 2018098306 | A1 | 5/2018 |
| WO | 2019112899 | A3 | 7/2019 |
| WO | 2020088631 | A1 | 5/2020 |
| WO | 2020102589 | A1 | 5/2020 |
| WO | 2020210398 | A1 | 10/2020 |

OTHER PUBLICATIONS

Gomes-Silva D, et al. (Jan. 2, 2019) Mol Ther. 27(1):272-280. (doi: 10.1016/j.ymthe.2018.10.001). Epub Oct. 4, 2018.*

(Continued)

*Primary Examiner* — Robert S Landsman

(74) *Attorney, Agent, or Firm* — Platinum Intellectual Property PC

(57) ABSTRACT

Provided is an engineered immune cell. The cell expresses a chimeric antigen receptor comprising an antigen-binding region. The antigen-binding region comprises an anti-CD7 antibody, and the expression of endogenous CD7, at least one TCR/CD3 gene, and at least one MHC-II related gene is suppressed or silenced. Further provided is the use of the engineered immune cell in the treatment of diseases associated with CD7 expression.

19 Claims, 8 Drawing Sheets

Specification includes a Sequence Listing.

(56) References Cited

OTHER PUBLICATIONS

Rasaiyaah (2018) JCI Insight. 3(13):e99442. (https://doi.org/10.1172/jci.insight.99442).*
Villard J, et al. (May 2000) Molecular and Cellular Biology, 20(10):3364-3376.*
Miller BC and Maus MV (2015) Oncol Res Treat. 38:683-690. (DOI: 10.1159/000442170).*
Hong M, et al. (Oct. 12, 2020) Cancer Cell. 38:473-488. (https://doi.org/10.1016/j.ccell.2020.07.005).*
Cook KD and Whitmire JK (Jan. 15, 2013) J Immunol. 190(2):1-20. (doi:10.4049/jimmunol.1202448).*
Hall T, et al. (2019) Journal for Immuno Therapy of Cancer. 7(263):8 pages. (https://doi.org/10.1186/s40425-019-0761-3).*
Cooper Matthew L et al: "An "off-the-shelf" fratricide-resistant CAR-T for the treatment of T cell hematologic malignancies", Blood Cancer Journal, Nature Publishing Group UK, London, vol. 32, No. 9, Feb. 20, 2018 (Feb. 20, 2018), pp. 1970-1983, XP036583020, ISSN: 0887-6924, DOI: 10.1038/S41375-018-0065-5; [retrieved on Feb. 20, 2018].
Diogo Gomes-Silva: "CD7-edited T cells expressing a CD7-specific CAR for the therapy of T-cell malignancies", Blood, [Online]; vol. 130, No. 3, Jul. 20, 2017 (Jul. 20, 2017), pp. 285-296, XP093158481, US, ISSN: 0006-4971, DOI: 10.1182/blood-2017-01-761320; Retrieved from the Internet: U RL:http://ashpublications.org/blood/article-pdf/130/3/285/1404621/blood761320.pdf[retrieved on Jul. 23, 2024].
First Office Action by EPO of counterpart European patent application No. 21888499, dated Sep. 11, 2024.
First Office Action by JPO of counterpart Japanese application No. 2023-526562, dated Jul. 9, 2024.
First Office Action by KIPO of counterpart Korean paten application No. 10-2023-7014559, dated Sep. 29, 2025.
Second Office Action by EPO of counterpart European patent application No. 21888499, dated May 16, 2025.
Second Office Action by JPO of counterpart Japanese application No. 2023-526562, dated Jan. 21, 2025.
Third Office Action by EPO of counterpart European patent application No. 21888499, dated Oct. 1, 2025.
Advances in gene editing in treatment of CAR-T.
English translation of ISR of WO2022095802.
International Search Report of WO2022095802.
Military Medical Journal of SW China vol. 19 No 1.
Written Opinion of The International Searching Authority of WO2022095802.

* cited by examiner

IMMUNE CELL EXPRESSING A CHIMERIC ANTIGEN RECEPTOR TARGETING CD7 AND HAVING SUPPRESSED OR SILENCED EXPRESSION OF TCR/CD3- AND MHC-II-RELATED-GENES AND METHOD OF USE THEREOF FOR TREATMENT

RELATED APPLICATIONS

This application is a United States National Stage Application filed under 35 U.S.C § 371 of PCT Patent Application Serial No. PCT/CN2021/127567, filed Oct. 29, 2021, which claims priority to Chinese Patent Application Serial No. CN 202011209352.X, filed Nov. 3, 2020, the disclosure of all of which are hereby incorporated by reference in their entirety.

TECHNICAL FIELD

The present disclosure belongs to the field of immunotherapy. More specifically, the present disclosure relates to a CD7-targeting chimeric antigen receptor and use thereof in the treatment of diseases.

BACKGROUND ART

In recent years, cancer immunotherapy technology has developed rapidly. In particular, chimeric antigen receptor T cell (CAR-T)-related immunotherapy, as a new type of adoptive immunotherapy technology, has shown very significant clinical efficacy in the treatment of various solid tumors and hematological tumors.

According to the source of T cells used to construct CAR-T cells, CAR-T cells can be divided into autologous CAR-T cells and allogeneic CAR-T cells (also known as universal CAR-T). Autologous CAR-T cells have the advantage of avoiding the risk of immune rejection, because the initial T cells come from the patient receiving CAR-T therapy; but they also have very obvious disadvantages: high cost and long production cycle. Therefore, more and more researches focus on the development of universal CAR-T cells. Universal CAR-T can be prepared from T cells isolated from the peripheral blood of healthy donors, which greatly shortens the time for patients to wait for treatment. In addition, the viability and function of T cells obtained from healthy donors are also superior to that of T cells derived from patients, and can increase the infection rate of CAR cells and improve the therapeutic effect.

CD7 is a cell surface glycoprotein with a molecular weight of about 40 kDa and belongs to the immunoglobulin superfamily. CD7 is expressed in most T cells, NK cells, myeloid cells, T cell acute lymphoblastic leukemia/lymphoma, acute myelogenous leukemia and chronic myelogenous leukemia. It has been reported that the CD7 molecule acts as a co-stimulatory signal during T cell activation through the binding with its ligand K12/SECTM1. In addition, disruption of the CD7 molecule in mouse T progenitor cells still resulted in normal T cell development and homeostasis, suggesting that CD7 does not appear to have critical effects on T cell development and function, making it a very suitable therapeutic target for the treatment of T-cell acute lymphoblastic leukemia (T-ALL). Indeed, CD7 has been extensively studied as a target of cytotoxic molecules for the treatment of leukemia and lymphoma.

The current CAR-T therapy targeting CD7, especially the universal CAR-T therapy, is still very limited. Therefore, the present disclosure aims to provide a highly efficient universal CAR-T cell targeting CD7 and a use thereof in treating diseases.

SUMMARY

In a first aspect, the present disclosure provides an engineered immune cell, (1) expressing a chimeric antigen receptor comprising an antigen-binding region, the antigen-binding region comprising an anti-CD7 antibody; and (2) having suppressed or silenced expression of endogenous CD7, at least one TCR/CD3 gene, and at least one MHC-II related gene.

In an embodiment, the chimeric antigen receptor comprises the anti-CD7 antibody, a transmembrane domain, and an intracellular signaling domain.

In an embodiment, the anti-CD7 antibody comprises CDR-L1, CDR-L2 and CDR-L3 as set forth in SEQ ID NOs: 1, 2 and 3 respectively, and CDR-H1, CDR-H2 and CDR-H3 as set forth in SEQ ID NOs: 4, 5 and 6 respectively. In a preferred embodiment, the anti-CD7 antibody comprises a light chain variable region having at least 90% identity to an amino acid sequence selected from the group consisting of SEQ ID NOs: 7, 10, 13, 16 and 19, and a heavy chain variable region having at least 90% identity to an amino acid sequence selected from the group consisting of SEQ ID NOs: 8, 11, 14, 17 and 20. In a preferred embodiment, the amino acid sequence of the anti-CD7 antibody is selected from the group consisting of SEQ ID NOs: 9, 12, 15, 18 and 21.

In an embodiment, the antigen-binding region of the chimeric antigen receptor further comprises an antibody targeting a second antigen selected from the group consisting of: TSHR, CD19, CD123, CD22, BAFF-R, CD30, CD171, CS-1, CLL-1, CD33, EGFRvIII, GD2, GD3, BCMA, GPRC5D, Tn Ag, PSMA, ROR1, FLT3, FAP, TAG72, CD38, CD44v6, CEA, EPCAM, B7H3, KIT, IL-13Ra2, mesothelin, IL-1 1Ra, PSCA, PRSS21, VEGFR2, LewisY, CD24, PDGFR-β, SSEA-4, CD20, AFP, Folate receptor α, ERBB2 (Her2/neu), MUC1, EGFR, CS1, CD138, NCAM, Claudin18.2, Prostase, PAP, ELF2M, Ephrin B2, IGF-I receptor, CAIX, LMP2, gploo, bcr-abl, tyrosinase, EphA2, Fucosyl GM1, sLe, GM3, TGS5, HMWMAA, o-acetyl-GD2, Folate receptor β, TEM1/CD248, TEM7R, CLDN6, GPRC5D, CXORF61, CD97, CD 179a, ALK, polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos associated antigen 1, p53, p53 mutant, prostate specific protein, survivin and telomerase, PCTA-1/Galectin 8, MelanA/MART1, Ras mutant, hTERT, sarcoma translocation breakpoint, ML-IAP, ERG (TMPRSS2 ETS fusion gene), NA17, PAX3, androgen receptor, Cyclin B1, MYCN, RhoC, TRP-2, CYP1B 1, BORIS, SART3, PAX5, OY-TES 1, LCK, AKAP-4, SSX2, RAGE-1, human telomerase reverse transcriptase, RU1, RU2, intestinal tract carboxylesterase, mut hsp70-2, CD79a, CD79b, CD72, LAIR1, FCAR, LILRA2, CD300LF, CLEC12A, BST2, EMR2, LY75, GPC3, FCRL5, IGLL1, PD1, PDL1, PDL2, TGF β, APRIL, NKG2D and any combination thereof. More preferably, the antibody targeting a second antigen is an antibody targeting CD19. In a preferred embodiment, the anti-CD19 antibody comprises a light chain variable region having at least 90% identity to an amino acid sequence selected from the group consisting of SEQ ID NOs: 52 and 55, and a heavy chain variable region having at least 90% identity to an amino acid sequence selected from the group consisting of SEQ ID NOs: 53 and 56. In a preferred embodiment, the amino acid sequence of the anti-CD19 antibody is selected from the group consisting of SEQ ID NOs: 54 and 57.

In an embodiment, the transmembrane domain is a transmembrane domain of a protein selected from the group consisting of: TCR α chain, TCR β chain, TCR γ chain, TCR δ chain, CD3 ζ subunit, CD3 ε subunit, CD3 γ subunit, CD3 δ subunit, CD45, CD4, CD5, CD8 α, CD9, CD16, CD22, CD33, CD28, CD37, CD64, CD80, CD86, CD134, CD137 and CD154. Preferably, the transmembrane domain is a transmembrane domain of a protein selected from the group consisting of CD8 α, CD4 and CD28.

In an embodiment, the intracellular signaling domain is an intracellular region of a protein selected from the group consisting of: FcR γ, FcR β, CD3 γ, CD3 δ, CD3 ε, CD3 ζ, CD22, CD79a, CD79b, and CD66d. Preferably, the intracellular signaling domain comprises a CD3 ζ intracellular region.

In an embodiment, the chimeric antigen receptor further comprises at least one co-stimulatory domain, which is an intracellular region of a protein selected from the group consisting of: TLR1, TLR2, TLR3, TLR4, TLR5, TLR6, TLR7, TLR8, TLR9, TLR10, CARD11, CD2, CD7, CD8, CD18 (LFA-1), CD27, CD28, CD30, CD40, CD54 (ICAM), CD83, CD134 (OX40), CD137 (4-1BB), CD270 (HVEM), CD272 (BTLA), CD276 (B7-H3), CD278 (ICOS), CD357 (GITR), DAP10, DAP12, LAT, NKG2C, SLP76, PD-1, LIGHT, TRIM, ZAP70 and a combination thereof. Preferably, the co-stimulatory domain is an intracellular region of CD27, CD28, CD134, CD137 or CD278 or a combination thereof.

In an embodiment, the TCR/CD3 gene is selected from the group consisting of TRAC, TRBC, CD3 γ, CD3 δ, CD3 ε, CD3 ζ and a combination thereof.

In an embodiment, the MHC-II related gene is selected from the group consisting of HLA-DPA, HLA-DQ, HLA-DRA, RFX5, RFXAP, RFXANK, CIITA and a combination thereof, preferably selected from the group consisting of RFX5, RFXAP, RFXANK, CIITA and a combination thereof.

In a preferred embodiment, the engineered immune cell of the present disclosure has suppressed or silenced expression of endogenous CD7, suppressed or silenced expression of at least one TCR/CD3 gene selected from the group consisting of TRAC and TRBC and suppressed or silenced expression of at least one MHC class II gene selected from the group consisting of RFX5, RFXAP, RFXANK and CIITA. More preferably, the engineered immune cell of the present disclosure has suppressed or silenced expression of endogenous CD7, at least one TCR/CD3 gene selected from the group consisting of TRAC and TRBC, and RFX5.

In an embodiment, the engineered immune cell further expresses a NK inhibitory molecule, which comprises one or more NK inhibitory ligands, a transmembrane domain and at least one co-stimulatory domain.

In an embodiment, the NK inhibitory ligand is an antibody targeting a NK inhibitory receptor selected from the group consisting of a NKG2/CD94 component (e.g., NKG2A, NKG2B, CD94); a member of the killer cell Ig-like receptor (KIR) family (e.g., KIR2DL1, KIR2DL2/3, KIR2DL5A, KIR2DL5B, KIR3DL1, KIR3DL2, and KIR3DL3); a member of the leukocyte Ig-like receptor (LIR) family (e.g., LIR1, LIR2, LIR3, LIR5, and LIR8); a member of the NK cell receptor protein 1 (NKR-P1) family (e.g., NKR-P1B and NKR-P1D); an immune checkpoint receptor (e.g., PD-1, TIGIT, and CD96, TIM3, LAG3); carcinoembryonic antigen-related cell adhesion molecule 1 (CEACAM1); a member of the sialic acid-binding immunoglobulin-like lectin (SIGLEC) family (e.g., SIGLEC7 and SIGLEC9); leukocyte-associated immunoglobulin-like receptor 1 (LAIR1); a member of the Ly49 family (e.g., Ly49A, Ly49C, Ly49F, Ly49G1 and Ly49G4) and killer cell lectin-like receptor G1 (KLRG1). Preferably, the NK inhibitory receptor is preferably selected from the group consisting of NKG2A, NKG2B, CD94, LIR1, LIR2, LIR3, LIR5, LIR8, KIR2DL1, KIR2DL2/3, KIR2DL5A, KIR2DL5B, KIR3DL1, KIR3DL2, KIR3DL3, CEACAM1, LAIR1, NKR-P1B, NKR-P1D, PD-1, TIGIT, CD96, TIM3, LAG3, SIGLEC7, SIGLEC9, Ly49A, Ly49C, Ly49F, Ly49G1, Ly49G4 and KLRG1. More preferably, the NK inhibitory receptor is selected from the group consisting of NKG2A, NKG2B, CD94, LIR1, LIR2, LIR3, KIR2DL1, KIR2DL2/3, KIR3DL1, CEACAM1, LAIR1 and KLRG1. Still more preferably, the NK inhibitory receptor is selected from the group consisting of NKG2A, NKG2B, LIR1, KIR2DL1, KIR2DL2/3, KIR3DL1, CEACAM1, LAIR1 and KLRG1.

In an embodiment, the NK inhibitory ligand is a natural ligand of a NK inhibitory receptor or a NK inhibitory receptor binding region comprised thereof. Preferably, the NK inhibitory ligand is selected from the group consisting of HLA-E, HLA-F, HLA-G, cadherin, collagen, OCIL, sialic acid, an immune checkpoint ligand (e.g., PD-L1/PD-L2, CTLA4, CD155, CD112, CD113, Gal-9, FGL1, etc.), and a NK inhibitory receptor binding region comprised thereof. More preferably, the NK inhibitory ligand is selected from the group consisting of HLA-E, HLA-F, HLA-G, cadherin, collagen, OCIL, sialic acid, PD-L1/PD-L2, CTLA-4, CD155, CD112, CD113, Gal-9, FGL1, and a NK inhibitory receptor binding region comprised thereof; more preferably selected from the group consisting of HLA-E, HLA-F, HLA-G, cadherin, PD-L1, PD-L2, and a NK inhibitory receptor binding region comprised thereof. In a preferred embodiment, the NK inhibitory ligand is selected from the group consisting of a HLA-E extracellular region, a HLA-G extracellular region, an E-cadherin extracellular region, a PD-L1 extracellular region and a PD-L2 extracellular region. In a preferred embodiment, the NK inhibitory ligand is an E-cadherin extracellular region comprising EC1 and EC2, more preferably comprising EC1, EC2, EC3, EC4 and EC5. In a preferred embodiment, the NK inhibitory ligand is an extracellular region of PD-L1 or PD-L2. In a preferred embodiment, the NK inhibitory ligand is a HLA-E extracellular region. In a preferred embodiment, the NK inhibitory ligand is a HLA-G extracellular region.

In an embodiment, the NK inhibitory molecule further comprises a CD3 ζ intracellular region as an intracellular signaling domain.

In an embodiment, the engineered immune cell is a T cell, a macrophage, a dendritic cell, a monocyte, a NK cell or a NKT cell. Preferably, the engineered immune cell is a T cell, such as CD4+/CD8+ T cell, CD4+ helper T cell (such as a Th1 or Th2 cell), CD8+ T cell (such as cytotoxic T cell), tumor infiltrating cell, memory T cell, naive T cell, γδ-T cell, αβ-T cell.

In an aspect, the present disclosure further provides a pharmaceutical composition, comprising the engineered immune cell described in the present disclosure as an active agent, and one or more pharmaceutically acceptable excipients.

In an aspect, the present disclosure further provide a method for treating a subject with a disease associated with CD7 expression, comprising administering to the subject an effective amount of the engineered immune cell or the pharmaceutical composition according to the present disclosure. Therefore, the present disclosure further encompasses the use of the engineered immune cell in the preparation of a medicine for treating a disease associated with CD7 expression.

DETAILED DESCRIPTION OF EMBODIMENTS

Unless otherwise specified, all scientific and technical terms used herein have the same meaning as commonly understood by one of ordinary skill in the art to which this disclosure belongs.

Chimeric Antigen Receptor

In a first aspect, the present disclosure provides an engineered immune cell, wherein the cell: (1) expresses a chimeric antigen receptor comprising an antigen-binding region, the antigen-binding region comprising an anti-CD7 antibody; and (2) has suppressed or silenced expression of endogenous CD7, at least one TCR/CD3 gene, and at least one MHC-II related gene.

As used herein, the term "chimeric antigen receptor" or "CAR" refers to an artificially constructed hybrid polypeptide, where the hybrid polypeptide generally includes an antigen-binding region (e.g., an antibody or antigen-binding portion thereof), a transmembrane domain, at least one optional co-stimulatory domain, and an intracellular signaling domain, and various domains are linked via a linker. CAR can redirect the specificity and reactivity of T cell and other immune cells to a selected target in a non-MHC-restricted manner by utilizing the antigen binding properties of antibodies. Non-MHC-restricted antigen recognition gives CAR-expressing immune cells the ability to recognize an antigen independent of antigen processing, thus bypassing the major mechanism of tumor escape.

In an embodiment, the CAR expressed by the engineered immune cells provided by the present disclosure comprises a CD7-targeting antibody or an antigen-binding fragment thereof, a transmembrane domain, and an intracellular signaling domain.

As used herein, the term "antibody" has the broadest meaning understood by those skilled in the art and includes monoclonal antibodies (including whole antibodies), polyclonal antibodies, multivalent antibodies, multispecific antibodies (e.g., bispecific antibodies), and antibody fragments or synthetic polypeptides carrying one or more CDR sequences capable of exhibiting the desired biological activity. The antibodies of the disclosure may be of any class (e.g., IgG, IgE, IgM, IgD, IgA, etc.) or subclass (e.g., IgG1, IgG2, IgG2a, IgG3, IgG4, IgA1, IgA2, etc.). Antibodies of the present disclosure also include recombinant antibodies, human antibodies, humanized antibodies, murine antibodies, chimeric antibodies, and antigen-binding portions thereof.

As used herein, "antibody fragment" or "antigen-binding portion" refers to a portion of an intact antibody, and typically comprises the antigen-binding site of the intact antibody and thus retains the ability to bind antigen. Examples of antibody fragments in the present disclosure include, but are not limited to: Fab, Fab', F(ab')2, Fd fragment, Fd', Fv fragment, scFv, disulfide-linked Fv (sdFv), heavy chain variable region (VH) or light chain variable region (VL) of an antibody, linear antibody, "diabody" with two antigen binding sites, single domain antibody, nanobody, a natural ligand for the antigen or a functional fragment thereof. Accordingly, an "antibody" of the present disclosure encompasses an antibody fragment or an antigen-binding portion of an antibody as defined above.

In an embodiment, the anti-CD7 antibody of the disclosure is an anti-CD7 scFv. "Single-chain antibody" and "scFv" are used interchangeably herein and refer to an antibody formed by linking the heavy chain variable region (VH) and the light chain variable region (VL) of an antibody through a linker. The optimal length and/or amino acid composition of the linker can be determined as desired. The length of the linker can significantly affect the folding and interaction of the variable domain of scFv. In fact, if shorter linkers (e.g., with between 5-10 amino acids) are used, intrachain folding can be prevented. For selection of linker size and composition, see, e.g., Hollinger et al., 1993 Proc Natl Acad. Sci. U.S.A. 90:6444-6448; U.S. Patent Application Publication Nos. 2005/0100543, 2005/0175606, 2007/0014794 and PCT Publication Nos. WO2006/020258 and WO2007/024715, the entire contents of which are incorporated herein by reference. A scFv may comprise VH and VL linked in any order, e.g. VH-linker-VL or VL-linker-VH.

In an embodiment, the CAR of the present disclosure comprises a CD7-targeting antibody, which comprises CDR-L1, CDR-L2 and CDR-L3 as set forth in SEQ ID NOs: 1, 2, and 3, respectively, and CDR-H1, CDR-H2 and CDR-H3 as set forth in SEQ ID NOs: 4, 5 and 6 respectively. Preferably, the CD7-targeting antibody of the present disclosure comprises a light chain variable region having at least 70%, preferably at least 80%, more preferably at least 90%, at least 95%, at least 97%, at least 99% or 100% sequence identity to an amino acid sequence selected from the group consisting of SEQ ID NOs: 7, 10, 13, 16 and 19, and a heavy chain variable region having at least 70%, preferably at least 80%, more preferably at least 90%, at least 95%, at least 97%, at least 99% or 100% sequence identity to an amino acid sequence selected from the group consisting of SEQ ID NOs: 8, 11, 14, 17 and 20. More preferably, the chimeric antigen receptor of the present disclosure comprises an anti-CD7 antibody having an amino acid sequence as set forth in SEQ ID NOs: 9, 12, 15, 18 or 21.

In an embodiment, in addition to the antibody targeting CD7, the antigen-binding region of the chimeric antigen receptor of the present disclosure comprises an antibody targeting a second antigen selected from the group consisting of: TSHR, CD19, CD123, CD22, BAFF-R, CD30, CD171, CS-1, CLL-1, CD33, EGFRvIII, GD2, GD3, BCMA, GPRC5D, Tn Ag, PSMA, ROR1, FLT3, FAP, TAG72, CD38, CD44v6, CEA, EPCAM, B7H3, KIT, IL-13Ra2, mesothelin, IL-1 1Ra, PSCA, PRSS21, VEGFR2, LewisY, CD24, PDGFR-β, SSEA-4, CD20, AFP, Folate receptor α, ERBB2 (Her2/neu), MUC1, EGFR, CS1, CD138, NCAM, Claudin18.2, Prostase, PAP, ELF2M, Ephrin B2, IGF-I receptor, CAIX, LMP2, gploo, bcr-abl, tyrosinase, EphA2, Fucosyl GM1, sLe, GM3, TGS5, HMWMAA, o-acetyl-GD2, Folate receptor β, TEM1/CD248, TEM7R, CLDN6, GPRC5D, CXORF61, CD97, CD 179a, ALK, polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos associated antigen 1, p53, p53 mutant, prostate specific protein, survivin and telomerase, PCTA-1/Galectin 8, MelanA/MART1, Ras mutant, hTERT, sarcoma translocation breakpoint, ML-IAP, ERG (TMPRSS2 ETS fusion gene), NA17, PAX3, androgen receptor, Cyclin B1, MYCN, RhoC, TRP-2, CYP1B 1, BORIS, SART3, PAX5, OY-TES 1, LCK, AKAP- 4, SSX2, RAGE-1, human telomerase reverse transcriptase, RU1, RU2, intestinal tract carboxylesterase, mut hsp70-2, CD79a, CD79b, CD72, LAIR1, FCAR, LILRA2, CD300LF, CLEC12A, BST2, EMR2, LY75, GPC3, FCRL5, IGLL1, PD1, PDL1, PDL2, TGF β, APRIL, NKG2D and any combination thereof. Preferably, the tumor antigen is selected from the group consisting of CD19, CD20, CD22, CD30, CD33, CD38, CD123, CD138, CD171, MUC1, AFP, Folate receptor α, CEA, PSCA, PSMA, Her2, EGFR, IL13Ra2, GD2, NKG2D, EGFRvIII, CS1, BCMA, mesothelin, and any combination thereof. All antibodies known in the art targeting the above tumor antigens can be used in the present disclosure.

In a preferred embodiment, the antibody targeting a second antigen is an antibody targeting CD19, which comprises a light chain variable region having at least 70%, preferably at least 80%, more preferably at least 90%, at least 95%, at least 97%, at least 99% or 100% sequence identity to an amino acid sequence as set forth in SEQ ID NO: 52 or 55, and a heavy chain variable region having at least 70%, preferably at least 80%, more preferably at least 90%, at least 95%, at least 97%, at least 99% or 100% sequence identity to an amino acid sequence as set forth in SEQ ID NO: 53 or 56. More preferably, the chimeric antigen receptor of the present disclosure comprises a CD7-targeting antibody and a CD19-targeting antibody, and the amino acid sequence of the CD19-targeting antibody is set forth in SEQ ID NO: 54 or 57.

The term "functional variant" or "functional fragment" refers to a variant that substantially includes the amino acid sequence of a parent, but, compared with the parent amino acid sequence, comprises at least one amino acid modification (i.e., substitution, deletion, or insertion), provided that the variant retains the biological activity of the parent amino acid sequence. In an embodiment, the amino acid modification is preferably a conservative modification.

As used herein, the term "conservative modification" refers to amino acid modification that does not significantly affect or alter the binding characteristics of the antibody or antibody fragment comprising the amino acid sequence. These conservative modifications include amino acid substitution, addition, and deletion. The modifications can be introduced into the chimeric antigen receptor of the present disclosure by standard techniques known in the art, such as site-directed mutagenesis and PCR-mediated mutagenesis. The conservative amino acid substitution is a substitution in which the amino acid residue is replaced with an amino acid residue having a similar side chain. Amino acid residue families having a similar side chain have been defined in the art, including basic side chain (e.g., lysine, arginine, histidine), acidic side chain (e.g., aspartic acid, glutamic acid), uncharged polar side chain (e.g., glycine, asparagine, glutamine, serine, threonine, tyrosine, cysteine), nonpolar side chain (e.g., alanine, valine, leucine, isoleucine, proline, phenylalanine, methionine, tryptophan), β-branched side chain (e.g., threonine, valine, isoleucine), and aromatic side chain (e.g., tyrosine, phenylalanine, tryptophan, histidine). The conservative modifications may be selected, for example, based on polarity, charge, solubility, hydrophobicity, hydrophilicity, and/or similarity in amphiphilic properties of residues involved.

Thus, the "functional variant" or "functional fragment" has at least 75%, preferably at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the parent amino acid sequence, and retains the biological activity, e.g., binding activity, of the parent amino acid.

As used herein, the term "sequence identity" indicates the degree to which two (nucleotide or amino acid) sequences have the same residue at the same position in an alignment, and is generally expressed by percentage. Preferably, the identity is determined over the entire length of the sequences being compared. Thus, two copies with completely identical sequences have 100% identity. Those skilled in the art will recognize that some algorithms can be used to determine sequence identity using standard parameters, for example, Blast (Altschul et al. (1997) Nucleic Acids Res. 25:3389-3402), Blast2 (Altschul et al. (1990) J. Mol. Biol. 215:403-410), Smith-Waterman (Smith et al. (1981) J. Mol. Biol. 147:195-197), and ClustalW.

As used herein, the term "transmembrane domain" refers to a polypeptide structure that enables expression of a chimeric antigen receptor on the surface of an immune cell (e.g., a lymphocyte, a NK cell, or a NKT cell), and guides a cellular response of the immune cell against the target cell. The transmembrane domain may be natural or synthetic, and also may be derived from any membrane-bound protein or transmembrane protein. The transmembrane domain is capable of signaling when the chimeric antigen receptor binds to the target antigen. The transmembrane domains particularly suitable for use in the present disclosure may be derived from, for example, a TCR α chain, a TCR β chain, a TCR γ chain, a TCR δ chain, a CD3 ζ subunit, a CD3 ε subunit, a CD3 γ subunit, a CD3 δ subunit, CD45, CD4, CD5, CD8 α, CD9, CD16, CD22, CD33, CD28, CD37, CD64, CD80, CD86, CD134, CD137, CD154, and functional fragments thereof. Alternatively, the transmembrane domain may be synthesized and may mainly comprise hydrophobic residues such as leucine and valine. Preferably, the transmembrane domain is derived from a CD8 α chain or CD28, and has at least 70%, preferably at least 80%, more preferably at least 90%, least 95%, least 97% or least 99% or 100% sequence identity to an amino acid sequence as set forth in SEQ ID NO: 22 or 24, or the encoding sequence thereof has at least 70%, preferably at least 80%, more preferably at least 90%, least 95%, least 97% or least 99% or 100% sequence identity to a nucleotide sequence as set forth in SEQ ID NO: 23 or 25.

In an embodiment, the chimeric antigen receptor of the present disclosure may further comprise a hinge region located between the antigen-binding region and the transmembrane domain. As used herein, the term "hinge region" generally refers to any oligopeptide or polypeptide that functions to link a transmembrane domain to an antigen-binding region. Specifically, the hinge region serves to provide greater flexibility and accessibility to the antigen-binding region. The hinge region may comprise up to 300 amino acids, preferably 10 to 100 amino acids and most preferably 25 to 50 amino acids. The hinge region may be completely or partially derived from a natural molecule, for example, completely or partially from the extracellular region of CD8, CD4 or CD28, or completely or partially from an antibody constant region. Alternatively, the hinge region may be a synthetic sequence corresponding to a naturally occurring hinge sequence, or may be a completely synthetic hinge sequence. In a preferred embodiment, the hinge region comprises a hinge region portion of a CD8 α chain, CD28, an Fc γ RIII a receptor, an IgG4, or an IgG1, more preferably a hinge from CD8α, CD28 or IgG4, which has at least 70%, preferably at least 80%, more preferably at least 90%, least 95%, least 97% or least 99% or 100% sequence identity to an amino acid sequence as set forth in SEQ ID NO: 38, 40 or 42, or the encoding sequence thereof has at least 70%, preferably at least 80%, more preferably at least 90%, least 95%, least 97% or least 99% or 100% sequence identity to a nucleotide sequence as set forth in SEQ ID NO: 39, 41 or 43.

As used herein, the term "intracellular signaling domain" refers to a protein portion that transduces an effector function signal and guides a cell to perform a specified function. The intracellular signaling domain is responsible for intracellular primary signaling after the antigen-binding region binds to the antigen, thus causing activation of immune cell and immune reaction. In other words, the intracellular signaling domain is responsible for activating at least one of the normal effector functions of the immune cells in which the CAR is expressed. For example, the effector functions of T cell can be cytolytic activity or auxiliary activity, including secretion of cytokines.

In an embodiment, the intracellular signaling domain contained in the chimeric antigen receptor of the present disclosure may be cytoplasmic sequences of a T cell receptor and a co-receptor, upon antigen receptor binding, which act together to initiate primary signaling, as well as any derivative or variant of these sequences and any synthetic sequence having the same or similar function. The intracellular signaling domain may comprise many immunoreceptor tyrosine-based activation motifs (ITAM). Non-limiting examples of intracellular signaling domain of the present disclosure include, but are not limited to, the intracellular regions of FcR γ, FcR β, CD3 γ, CD3 δ, CD3 ε, CD3 ζ, CD22, CD79a, CD79b, and CD66d. In a preferred embodiment, the signaling domain of the CAR of the present disclosure may comprise a CD3 ζ intracellular region, which has at least 70%, preferably at least 80%, more preferably at least 90%, at least 95%, at least 97%, or at least 99% or 100% sequence identity to an amino acid sequence as set forth in SEQ ID NO: 30 or 32, or the encoding sequence thereof has at least 70%, preferably at least 80%, more preferably at least 90%, at least 95%, at least 97%, or at least 99% or 100% sequence identity to a nucleotide sequence as set forth in SEQ ID NO: 31 or 33.

In an embodiment, the chimeric antigen receptor of the present disclosure comprises one or more co-stimulatory domains. The co-stimulatory domain may be an intracellular functional signaling domain from a co-stimulatory molecule, which comprises an entire intracellular portion of the co-stimulatory molecule, or a functional fragment thereof. "Co-stimulatory molecule" refers to a homologous binding partner that specifically binds to a co-stimulatory ligand on a T cell, thereby mediating a co-stimulatory response (e.g. proliferation) of the T cell. The co-stimulatory molecule includes, but is not limited to, MHC class 1 molecules, BTLA, and Toll ligand receptors. Non-limiting examples of the co-stimulatory domain of the present disclosure include, but are not limited to, intracellular regions of the following proteins: TLR1, TLR2, TLR3, TLR4, TLR5, TLR6, TLR7, TLR8, TLR9, TLR10, CARD11, CD2, CD7, CD8, CD18 (LFA-1), CD27, CD28, CD30, CD40, CD54 (ICAM1), CD83, CD134 (OX40), CD137 (4-1BB), CD270 (HVEM), CD272 (BTLA), CD276 (B7-H3), CD278 (ICOS), CD357 (GITR), DAP10, DAP12, LAT, NKG2C, SLP76, PD-1, LIGHT, TRIM, CD94, LTB and ZAP70, and combinations thereof.

In a preferred embodiment, the co-stimulatory domain comprises one or more intracellular regions of a protein selected from the group consisting of DAP10, DAP12, CD27, CD28, CD134, 4-1BB or CD278. For example, in an embodiment, the co-stimulatory domain comprises the intracellular region of 4-1BB. In an embodiment, the co-stimulatory domain comprises the intracellular region of CD28. In an embodiment, the co-stimulatory domain comprises the intracellular region of 4-1BB and the intracellular region of CD28.

In an embodiment, the intracellular region of 4-1BB has at least 70%, preferably at least 80%, more preferably at least 90%, at least 95%, at least 97%, or at least 99% or 100% sequence identity to an amino acid sequence as set forth in SEQ ID NO: 28, or the encoding sequence thereof has at least 70%, preferably at least 80%, more preferably at least 90%, at least 95%, at least 97%, or at least 99% or 100% sequence identity to a nucleotide sequence as set forth in SEQ ID NO: 29. In an embodiment, the intracellular region of CD28 has at least 70%, preferably at least 80%, more preferably at least 90%, at least 95%, at least 97%, or at least 99% or 100% sequence identity to an amino acid sequence as set forth in SEQ ID NO: 26, or the encoding sequence thereof has at least 70%, preferably at least 80%, more preferably at least 90%, at least 95%, at least 97%, or at least 99% or 100% sequence identity to a nucleotide sequence as set forth in SEQ ID NO: 27.

In an embodiment, the CAR of the present disclosure may further comprise a signal peptide such that when it is expressed in a cell such as a T cell, the nascent protein is directed to the endoplasmic reticulum and subsequently to the cell surface. The core of the signal peptide may comprise a long hydrophobic amino acid segment, which has a tendency to form a single α-helix. At the end of the signal peptide, there is usually an amino acid segment recognized and cleaved by signal peptidase. The signal peptidase can cleave during or after translocation, so as to generate free signal peptide and mature protein. Then, the free signal peptide is digested by a specific protease. Signal peptides that can be used in the present disclosure are well known to those skilled in the art, for example, signal peptides derived from CD8 α, IgG1, GM-CSFRα, B2M and so on. In an embodiment, the signal peptide that can be used in the present disclosure is from B2M or CD8α, which has at least 70%, preferably at least 80%, more preferably at least 90%, at least 95%, at least 97%, or at least 99% or 100% sequence identity to an amino acid sequence as set forth in SEQ ID NO: 34 or 36, or the encoding sequence thereof has at least 70%, preferably at least 80%, more preferably at least 90%, at least 95%, at least 97%, or at least 99% or 100% sequence identity to a nucleotide sequence as set forth in SEQ ID NO: 35 or 37.

In an embodiment, the CAR of the present disclosure may further comprise a switch structure to regulate the expression time of the CAR. For example, the switch structure may be in a form of dimerization domain, which causes a conformational change by binding to a corresponding ligand thereof, and exposes the extracellular antigen-binding region to enable its binding to a targeted antigen, thereby activating a signaling pathway. Alternatively, a switch structure also may be used to link the antigen-binding region and signaling domain, respectively, and only when the switch structures are bound to each other (for example, in the presence of an inducing compound), the antigen-binding region and the signaling domain can be linked together through a dimer, thereby activating signaling pathway. The switch structure also can be in the form of a masking peptide. The masking peptide can shield the extracellular antigen-binding region, and prevent it from binding to the targeted antigen. When the masking peptide is cleaved by, for example, a protease, the extracellular antigen-binding region is exposed, making it become a "normal" CAR structure. A variety of switch structures known to those skilled in the art can be used in the present disclosure.

In an embodiment, the CAR of the present disclosure may further comprise a suicide gene, to make it express a cell death signal that can be induced by an exogenous substance, so as to eliminate the CAR cell when needed (e.g., when serious toxic side effects are produced). For example, the suicide gene may be in the form of an inserted epitope, e.g., a CD20 epitope, an RQR8, etc., and when needed, the CAR cell can be eliminated by adding an antibody or reagent that targets these epitopes. The suicide gene also may be herpes simplex virus thymidine kinase (HSV-TK), which gene can induce the cell to die when receiving ganciclovir treatment. The suicide gene may further be iCaspase-9, and dimerization of iCaspase-9 can be induced by a chemical induction drug such as AP1903 and AP20187, so as to activate the downstream Caspase3 molecule, and cause apoptosis. A variety of suicide genes known to those of skill in the art can be used in the present disclosure.

Inhibition or Silencing of Endogenous Gene Expression

In an embodiment, the engineered immune cell provided by the present disclosure has suppressed or silenced expression of endogenous CD7, at least one TCR/CD3 gene, and at least one MHC-II related gene.

CD7 is not only expressed in tumor cells, such as T cell acute lymphoblastic leukemia/lymphoma, acute myelogenous leukemia and chronic myelogenous leukemia, but also expressed in most normal T cells and NK cells. Therefore, in order to avoid mutual recognition and killing between CAR cells targeting CD7, it is necessary to inhibit or silence the expression of the endogenous CD7 gene of the CAR cells.

T cell receptor (TCR) is a characteristic mark on the surface of all T cells. It binds to CD3 through a non-covalent bond to form a TCR/CD3 complex, and binds to the specific MHC-antigen peptide complex on the surface of antigen-presenting cells to generate specific antigen stimulation signals, to activate T cells to play a killing role. Therefore, inhibiting or silencing the expression of the endogenous TCR/CD3 gene in a CAR-T cell can avoid its attack on normal cells or tissues in patients, thereby avoiding or reducing the risk of graft-versus-host disease (GvHD). TCR is a heterodimer composed of two different peptide chains, and usually divided into two types: α/β type and γ/δ type. More than 95% of peripheral T lymphocytes express TCR α/β. The TCR alpha chain is encoded by the TRAC gene, and the beta chain is encoded by the TRBC gene. Each peptide chain of TCR includes a variable region (V region), a constant region (C region), a transmembrane region and a cytoplasmic region, wherein the cytoplasmic region is very short and does not have the ability to transmit antigen stimulation signals. The TCR molecule belong to the immunoglobulin superfamily, and its antigen specificity exists in the V region; the V region has three hypervariable regions, CDR1, CDR2, and CDR3, among which CDR3 is the most variable, and directly determines the antigen-binding specificity of TCR. When TCR recognizes the MHC-antigen peptide complex, CDR1 and CDR2 recognize and bind to MHC molecules, while CDR3 directly binds to the antigen peptide. CD3 includes four subunits: γ, δ, ε, ζ, usually in the form of dimers εγ, εδ, ζζ. These four subunits all comprise the conserved immunoreceptor tyrosine-based activation motif (ITAM), and after the 2 tyrosine residues are phosphorylated by tyrosine protein kinase, they transmit activation signals to T cells. Thus, in an embodiment, the at least one TCR/CD3 gene is selected from the group consisting of: TRAC, TRBC, CD3 γ, CD3 δ, CD3 ε, CD3 ζ.

By detecting the composition of peripheral blood lymphocytes in patients, the inventors found that CD4+CD7− T cells accounted for about 20% of the total CD3+ T cells (FIG. 1). Since CAR cells targeting CD7 cannot recognize the CD4+CD7− T population, they cannot effectively kill this population. Instead, CD4+CD7− T cells will kill exogenous CAR cells by recognizing MHC-II molecules. Therefore, in order to avoid the killing of exogenous CAR-T cells by CD4+CD7− T cells in patients, the inventors consider inhibiting or silencing the expression of endogenous MHC-II related genes in CAR-T cells.

In the present disclosure, MHC-II related genes include MHC-II genes themselves, and genes that interact with MHC-II genes or regulate their expression.

The major histocompatibility complex (MHC), originally characterized as a protein that plays a major role in the transplant response, is expressed on the surface of all higher vertebrates and is called H-2 in mice, called HLA in human cells. There are two main classes of MHC: class I and class II. The MHC class I protein is a heterodimer of two proteins: one is the alpha chain of a transmembrane protein encoded by the MHC I gene, and the other is the beta2 microglobulin chain of an extracellular protein encoded by a gene not located within the MHC gene cluster. The alpha chain comprises three domains and the foreign peptide binds to two domains α1, α2 which are also the most variable at the N-terminus. The MHC class II protein is also a heterodimer, comprising two transmembrane proteins encoded by genes within the MHC complex. Class I MHC/antigen complexes interact with cytotoxic T cells (e.g., CD8+ T cells), while class II MHC present antigens to helper T cells (e.g., CD4+ T cells). Furthermore, MHC class I proteins tend to be expressed in almost all nucleated cells and platelets (and red blood cells in mice), whereas MHC class II proteins are more selectively expressed. Typically, MHC class II proteins are expressed on B cells, some macrophages and monocytes, activated T cells, Langerhans cells and dendritic cells.

The human HLA class II cluster comprises three major loci DP, DQ and DR. The Class II molecule is a heterodimer consisting of an alpha chain and a beta chain, both anchored in the membrane, where the alpha chain is approximately 33-35 kDa and comprises 5 exons. Exon 1 encodes the leader peptide, exons 2 and 3 encode the two extracellular domains, exon 4 encodes the transmembrane domain, and exon 5 encodes the cytoplasmic tail. Thus, in an embodiment, the MHC class II related gene is selected from the group consisting of: HLA-DPA, HLA-DQ and HLA-DRA.

The expression of MHC-II genes also depends on a variety of important positive regulatory proteins, such as RFX complex, CIITA and so on. The RFX complex is composed of three subunits: RFXANK (also known as RFXB), RFX5 and RFX accessory protein (also known as RFXAP). The RFX complex promotes the expression of MHC class II molecules by facilitating the binding of other transcription factors to the promoters of MHC class II molecules and enhancing the specificity of promoter binding. CIITA is a master controller of MHC class II expression. CIITA includes an N-terminal rich in acidic amino acids, a PST region rich in Pro, Ser, and Thr, a GTP-binding region in the middle, and a C-terminal rich in Leu repeat sequence (LRR), where the N-terminal acidic region and PST region are transcriptional activation area. Thus, in an embodiment, the MHC class II related gene is selected from the group consisting of: RFX5, RFXAP, RFXANK and CIITA.

Therefore, in an embodiment, the MHC class II related gene is selected from the group consisting of HLA-DPA, HLA-DQ, HLA-DRA, RFX5, RFXAP, RFXANK and CIITA, preferably selected from the group consisting of RFX5, RFXAP, RFXANK and CIITA, more preferably RFX5.

In an embodiment, the endogenous MHC class I gene (e.g., HLA-A, HLA-B, HLA-C, B2M, etc.) in the CAR-T cell is functional. In another embodiment, the expression of endogenous MHC-class I gene in CAR-T cells is also suppressed or silenced.

In an embodiment, the engineered immune cell expressing a CD7-targeting chimeric antigen receptor according to the present disclosure has suppressed or silenced expression of endogenous CD7, at least one TCR/CD3 gene, and at least one MHC-II related gene, wherein the at least one TCR/CD3 gene is selected from the group consisting of TRAC, TRBC, CD3 γ, CD3 δ, CD3 ε, CD3 ζ and a combination thereof; and the at least one MHC-II related gene is selected from the group consisting of HLA-DPA, HLA-DQ, HLA-DRA, RFX5, RFXAP, RFXANK, and CIITA. In a preferred embodiment, the engineered immune cell expressing a CD7-targeting chimeric antigen receptor according to the present disclosure has suppressed or silenced expression of endogenous CD7, at least one TCR/CD3 gene selected from the group consisting of TRAC and TRBC and at least one MHC class II gene selected from the group consisting of RFX5, RFXAP, RFXANK and CIITA. More preferably, the engineered immune cell expressing a CD7-targeting chimeric antigen receptor according to the present disclosure has suppressed or silenced expression of endogenous CD7, at least one TCR/CD3 gene selected from the group consisting of TRAC and TRBC, and RFX5. In an embodiment, the expression of MHC class I genes such as HLA-A, HLA-B, HLA-C and B2M in the engineered immune cells is functional.

In an embodiment, in addition to CD7, MHC-II-related genes and TCR/CD3 genes, the engineered immune cell of the present disclosure may further has suppressed or silenced expression of at least one gene selected from the group consisting of: CD52, GR, dCK and an and immune checkpoint gene such as PD1, LAG3, TIM3, CTLA4, PPP2CA, PPP2CB, PTPN6, PTPN22, PDCD1, HAVCR2, BTLA, CD160, TIGIT, CD96, CRTAM, TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT, FOXP3, PRDM1, BATF, GUCY1A2, GUCY1A3, GUCY1B2, and GUCY1B3.

Methods for inhibiting gene expression or for gene silencing are well known to those skilled in the art, including but not limited to, for example, DNA fragmentation mediated by meganucleases, zinc finger nucleases, TALE nucleases, or Cas enzymes in the CRISPR system, or gene inactivation by antisense oligonucleotides, RNAi, shRNA, and other technologies.

NK Inhibitory Molecule

The inventors also found that there is a large proportion (about 20%) of CD7− NK cells in patients (FIG. 1), which cannot be targeted and killed by CD7 CAR. Moreover, when the expression of MHC-II gene is suppressed or silenced, these cells may kill CAR cells.

Therefore, in an embodiment, in order to inhibit the killing of CAR-T cells by NK cells in the patient, the engineered immune cell further express a NK inhibitory molecule, which comprises one or more NK inhibitory ligands, a transmembrane domain and a co-stimulatory domain. For example, the NK inhibitory molecule comprises one or two NK inhibitory ligands, a transmembrane domain and a co-stimulatory domain.

The transmembrane domain and co-stimulatory domain contained in the NK inhibitory molecule have the same definitions as those contained in the chimeric antigen receptor as described above.

In an embodiment, the NK inhibitory ligand is an antibody targeting a NK inhibitory receptor selected from the group consisting of a NKG2/CD94 component (e.g., NKG2A, NKG2B, CD94); a member of the killer cell Ig-like receptor (KIR) family (e.g., KIR2DL1, KIR2DL2/3, KIR2DL5A, KIR2DL5B, KIR3DL1, KIR3DL2, and KIR3DL3); a member of the leukocyte Ig-like receptor (LIR) family (e.g., LIR1, LIR2, LIR3, LIR5, and LIR8); a member of the NK cell receptor protein 1 (NKR-P1) family (e.g., NKR-P1B and NKR-P1D); an immune checkpoint receptor (e.g., PD-1, TIGIT, and CD96, TIM3, LAG3); carcinoembryonic antigen-related cell adhesion molecule 1 (CEACAM1); a member of the sialic acid-binding immunoglobulin-like lectin (SIGLEC) family (e.g., SIGLEC7 and SIGLEC9); leukocyte-associated immunoglobulin-like receptor 1 (LAIR1); a member of the Ly49 family (e.g., Ly49A, Ly49C, Ly49F, Ly49G1 and Ly49G4) and killer cell lectin-like receptor G1 (KLRG1). Preferably, the NK inhibitory receptor is preferably selected from the group consisting of NKG2A, NKG2B, CD94, LIR1, LIR2, LIR3, LIR5, LIR8, KIR2DL1, KIR2DL2/3, KIR2DL5A, KIR2DL5B, KIR3DL1, KIR3DL2, KIR3DL3, CEACAM1, LAIR1, NKR-P1B, NKR-P1D, PD-1, TIGIT, CD96, TIM3, LAG3, SIGLEC7, SIGLEC9, Ly49A, Ly49C, Ly49F, Ly49G1, Ly49G4 and KLRG1. More preferably, the NK inhibitory receptor is selected from the group consisting of NKG2A, NKG2B, CD94, LIR1, LIR2, LIR3, KIR2DL1, KIR2DL2/3, KIR3DL1, CEACAM1, LAIR1 and KLRG1. Still more preferably, the NK inhibitory receptor is selected from the group consisting of NKG2A, NKG2B, LIR1, KIR2DL1, KIR2DL2/3, KIR3DL1, CEACAM1, LAIR1 and KLRG1.

In an embodiment, the NK inhibitory ligand is an antibody targeting a NK inhibitory receptor, said antibody being a whole antibody, Fab, Fab', F(ab')2, a Fv fragment, a scFv antibody fragment, a linear antibody, a sdAb or a nanobody.

In a preferred embodiment, the NK inhibitory ligand is an antibody targeting NKG2A. More preferably, the antibody targeting NKG2A comprises a light chain variable region having at least 70%, preferably at least 80%, more preferably at least 90%, at least 95%, at least 97%, at least 99% or 100% sequence identity to an amino acid sequence as set forth in SEQ ID NO: 59, 62 or 77, and a heavy chain variable region having at least 70%, preferably at least 80%, more preferably at least 90%, at least 95%, at least 97%, at least 99% or 100% sequence identity to an amino acid sequence as set forth in SEQ ID NO: 58, 61 or 76. More preferably, the amino acid sequence of the antibody targeting NKG2A is set forth in SEQ ID NO: 60, 63 or 78. Other antibodies targeting NKG2A known in the art can also be used in the present disclosure, such as Z270 (available from Immunotech, France), Z199 (available from Beckman Coulter, USA), 20D5 (available from BD Biosciences Pharmingen, USA), P25 (available from Morettaetal, Univ. Genova, Italy) and the like.

In a preferred embodiment, the NK inhibitory ligand is an antibody targeting KIR, e.g. KIR2DL1, KIR2DL2/3 and KIR3DL1. More preferably, the antibody targeting KIR comprises a light chain variable region having at least 70%, preferably at least 80%, more preferably at least 90%, at least 95%, at least 97%, at least 99% or 100% sequence identity to an amino acid sequence as set forth in SEQ ID NO: 65 or 79, and a heavy chain variable region having at least 70%, preferably at least 80%, more preferably at least 90%, at least 95%, at least 97%, at least 99% or 100% sequence identity to an amino acid sequence as set forth in SEQ ID NO: 66 or 80. More preferably, the amino acid sequence of the antibody targeting KIR is set forth in SEQ ID NO: 67 or 81. Other antibodies targeting KIR known in the art can also be used in the present disclosure, such as GL183 (targeting KIR2DL2/L3, available from Immunotech, France and Beckton Dickinson, USA), EB6 (targeting KIR2DL1, available from Immunotech, France and Beckton Dickinson, USA), AZ138 (targeting KIR3DL1, available from Morettaetal, Univ. Genova, Italy), Q66 (targeting KIR3DL2, available from Immunotech, France), Z27 (targeting KIR3DL1, available from Immunotech, France and Beckton Dickinson, USA) and the like.

In a preferred embodiment, the NK inhibitory ligand is an antibody targeting LIR1. More preferably, the antibody targeting LIR1 comprises a light chain variable region having at least 70%, preferably at least 80%, more preferably at least 90%, at least 95%, at least 97%, at least 99% or 100% sequence identity to an amino acid sequence as set forth in SEQ ID NO: 68 or 71, and a heavy chain variable region having at least 70%, preferably at least 80%, more preferably at least 90%, at least 95%, at least 97%, at least 99% or 100% sequence identity to an amino acid sequence as set forth in SEQ ID NO: 69 or 72. More preferably, the amino acid sequence of the antibody targeting LIR1 is set forth in SEQ ID NO: 70 or 73.

In an embodiment, the NK inhibitory ligand is a natural ligand of a NK inhibitory receptor or a NK inhibitory receptor binding region comprised thereof. Preferably, the NK inhibitory ligand is selected from the group consisting of HLA-E, HLA-F, HLA-G, cadherin, collagen, OCIL, sialic acid, an immune checkpoint ligand (e.g., PD-L1/PD-L2, CD155, CD112, CD113, Gal-9, FGL1, etc.), and a NK inhibitory receptor binding region comprised thereof. More preferably, the NK inhibitory ligand is selected from the group consisting of HLA-E, HLA-F, HLA-G, cadherin, collagen, OCIL, sialic acid, PD-L1/PD-L2, CTLA-4, CD155, CD112, CD113, Gal-9, FGL1, and a NK inhibitory receptor binding region comprised thereof; more preferably selected from the group consisting of HLA-E, HLA-F, HLA-G, cadherin, and a NK inhibitory receptor binding region comprised thereof. More preferably, the NK inhibitory ligand is selected from the group consisting of a HLA-E extracellular region, a HLA-G extracellular region, an E-cadherin (E-Cadherin) extracellular region, a PD-L1 extracellular region and a PD-L2 extracellular region.

In a preferred embodiment, the NK inhibitory ligand is an E-cadherin extracellular region comprising domains EC1 and EC2, more preferably comprising domains EC1, EC2, EC3, EC4 and EC5. Preferably, the E-cadherin extracellular region has at least 70%, preferably at least 80%, more preferably at least 90%, at least 95%, at least 97%, at least 99% or 100% sequence identity to an amino acid sequence as set forth in SEQ ID NO: 44 (comprising domains EC1 and EC2) or SEQ ID NO: 48 (comprising domains EC1, EC2, EC3, EC4 and EC5).

In an embodiment, the NK inhibitory ligand is a PD-L1 or PD-L2 extracellular region. Preferably, the PD-L1 extracellular region has at least 70%, preferably at least 80%, more preferably at least 90%, at least 95%, at least 97%, at least 99% or 100% sequence identity to an amino acid sequence as set forth in SEQ ID NO: 45, and the PD-L2 extracellular region has at least 70%, preferably at least 80%, more preferably at least 90%, at least 95%, at least 97%, at least 99% or 100% sequence identity to an amino acid sequence as set forth in SEQ ID NO: 46.

In an embodiment, the NK inhibitory ligand is a HLA-E extracellular region or a HLA-G extracellular region. Preferably, the HLA-E extracellular region has at least 70%, preferably at least 80%, more preferably at least 90%, at least 95%, at least 97%, at least 99% or 100% sequence identity to an amino acid sequence as set forth in SEQ ID NO: 50 (wild type) or SEQ ID NO: 51 (a mutant comprising Y84C mutation), and the HLA-G extracellular region has at least 70%, preferably at least 80%, more preferably at least 90%, at least 95%, at least 97%, at least 99% or 100% sequence identity to an amino acid sequence as set forth in SEQ ID NO: 49. It is known in the art that non-classical HLA-class I molecules (such as HLA-E, HLA-G) need to form a complex with B2M to exert their functions. Therefore, when B2M needs to be knocked out, in order for non-classical HLA class I molecules to exert their inhibitory function normally, it is necessary to introduce B2M with synonymous mutations in the DNA sequence to avoid being knocked out by gene editing tools. In other words, in B2M-knockout cells, the NK inhibitory ligand is a fusion molecule of B2M and the extracellular region of HLA-E or the extracellular region of HLA-G.

In yet another embodiment, the NK inhibitory molecule comprises at least two NK inhibitory ligands selected from the group consisting of anti-NKG2A scFv, anti-KIR scFv, anti-LIR1 scFv, HLA-E extracellular region, HLA-G extracellular region, E-cadherin extracellular region, PD-L1 extracellular region and PD-L2 extracellular region, more preferably PD-L1 extracellular region and HLA-E extracellular region.

In an embodiment, the NK inhibitory molecule further comprises an intracellular signaling domain. In an embodiment, the intracellular signaling domain is an intracellular region of a protein selected from the group consisting of: FcR γ, FcR β, CD3 γ, CD3 δ, CD3 ε, CD3 ζ, CD22, CD79a, CD79b, and CD66d. Preferably, the intracellular signaling domain comprises a CD3 ζ intracellular region.

In an embodiment, the NK inhibitory molecule may further comprise a signal peptide, such as a signal peptide from PDL1 or B2M. In an embodiment, the NK inhibitory molecule comprises a PD-L1 signal peptide, which has at least 70%, preferably at least 80%, more preferably at least 90%, at least 95%, at least 97%, at least 99% or 100% sequence identity to an amino acid sequence as set forth in SEQ ID NO: 44. Those skilled in the art can also select other suitable signal peptides as needed.

Engineered Immune Cell

The present disclosure further provides an engineered immune cell, wherein the cell: (1) expresses a chimeric antigen receptor comprising an antigen-binding region, the antigen-binding region comprising an anti-CD7 antibody and an optional second antigen region; and (2) has suppressed or silenced expression of endogenous CD7, at least one TCR/CD3 gene, and at least one MHC-II related gene. In an embodiment, the engineered immune cell of the present disclosure further expresses a NK inhibitory molecule comprising one or more NK inhibitory ligands, a transmembrane domain and a co-stimulatory domain.

As used herein, the term "immune cell" refers to any cell of the immune system that has one or more effector functions (e.g., cytotoxic cell killing activity, secretion of cytokines, induction of ADCC and/or CDC). For example, the immune cell may be a T cell, a macrophage, a dendritic cell, a monocyte, a NK cell, and/or a NKT cell, an immune cell derived from a stem cell, such as an adult stem cell, an embryonic stem cell, a cord blood stem cell, a progenitor cell, a bone marrow stem cell, an induced pluripotent stem cell, a totipotent stem cell, or a hematopoietic stem cell, and so on. Preferably, the immune cell is a T cell. The T cell may be any T cell, such as in vitro cultured T cell, for example, primary T cell, or T cell from in vitro cultured T cell line, e.g., Jurkat, SupT1, etc., or T cell obtained from a subject. Examples of subject include humans, dogs, cats, mice, rats, and transgenic species thereof. The T cell can be obtained from a variety of sources, including peripheral blood monocytes, bone marrow, lymph node tissue, umbilical blood, thymus tissue, tissue from sites of infection, ascites, pleural effusion, spleen tissue, and tumors. The T cell also may be concentrated or purified. The T cell may be at any stage of development including, but not limited to, a CD4+/CD8+ T cell, a CD4+ helper T cell (e.g., Th1 and Th2 cells), CD8+ T cell (e.g., cytotoxic T cell), tumor infiltrating cell, memory T cell, naive T cell, γδ-T cell, αβ-T cell. In a preferred embodiment, the immune cell is a human T cell. The T cell can be isolated from the blood of a subject using a variety of techniques known to those of skill in the art, such as Ficoll. In the present disclosure, the immune cell is engineered to express a chimeric antigen receptor and to suppress or silence the expression of endogenous CD7, at least one TCR/CD3 gene, and at least one MHC class II related gene.

The nucleic acid sequence encoding the chimeric antigen receptor polypeptide and an optional nucleic acid sequence encoding the NK inhibitory molecule can be introduced into the immune cell by conventional methods known in the art (e.g., by transduction, transfection, transformation). "Transfection" is a process of introducing a nucleic acid molecule or polynucleotide (including a vector) into a target cell. An example is RNA transfection, i.e., the process of introducing RNA (e.g., in vitro transcribed RNA, ivtRNA) into a host cell. This term is mainly used for a non-viral method in eukaryotic cells. The term "transduction" is generally used to describe virus-mediated transfer of nucleic acid molecules or polynucleotides. Transfection of animal cells typically involves opening transient pores or "holes" in the cell membrane, so as to allow uptake of material. Transfection may be carried out using calcium phosphate, by electroporation, by extrusion of cells, or by mixing cationic lipids with the material so as to produce liposomes which fuse with the cell membrane and deposit their cargo into the interior. Exemplary techniques for transfecting eukaryotic host cells include lipid vesicle-mediated uptake, heat shock-mediated uptake, calcium phosphate-mediated transfection (calcium phosphate/DNA co-precipitation), microinjection, and electroporation. The term "transformation" is used to describe the non-virus transfer of a nucleic acid molecule or polynucleotide (including a vector) to bacteria, and also to non-animal eukaryotic cells (including plant cells). Thus, the transformation is a genetic alteration of bacterial or non-animal eukaryotic cells, which is produced by direct uptake through a cell membrane from its surroundings and subsequent incorporation of exogenous genetic material (nucleic acid molecule). The transformation can be achieved by artificial means. In order for transformation to occur, the cell or bacterium must be in a competent state. For prokaryotic transformation, the techniques may include heat shock-mediated uptake, fusion to bacterial protoplasts of intact cells, microinjection, and electroporation.

After the nucleic acid or vector is introduced into the immune cells, those skilled in the art can amplify and activate the obtained immune cells by conventional techniques.

Pharmaceutical Composition

The present disclosure further provides a pharmaceutical composition, comprising the engineered immune cell described in the present disclosure as an active agent, and one or more pharmaceutically acceptable excipients.

As used herein, the term "pharmaceutically acceptable excipient" refers to a carrier and/or excipient that is pharmacologically and/or physiologically compatible (i.e., capable of triggering a desired therapeutic effect without causing any undesired local or systemic effects) with the subject and active ingredient, and it is well known in the art (see, e.g., Remington's Pharmaceutical Sciences. Edited by Gennaro A R, 19th ed. Pennsylvania: Mack Publishing Company, 1995). Examples of pharmaceutically acceptable excipient include, but are not limited to, filler, binder, disintegrant, coating agent, adsorbent, anti-adherent, glidant, antioxidant, flavoring agent, colorant, sweetener, solvent, co-solvent, buffer agent, chelating agent, surfactant, diluent, wetting agent, preservative, emulsifier, cladding agent, isotonic agent, absorption delaying agent, stabilizer, and tension regulator. It is known to those skilled in the art to select a suitable excipient to prepare the desired pharmaceutical composition of the present disclosure. Exemplary excipients for use in the pharmaceutical composition of the present disclosure include saline, buffered saline, dextrose, and water. Generally, the selection of a suitable excipient depends, in particular, on the active agent used, the disease to be treated, and the desired dosage form of the pharmaceutical composition.

The pharmaceutical composition according to the present disclosure is suitable for multiple routes of administration. Generally, the application is parenterally accomplished. Parenteral delivery methods include topical, intraarterial, intramuscular, subcutaneous, intramedullary, intrathecal, intraventricular, intravenous, intraperitoneal, intrauterine, intravaginal, sublingual, or intranasal administration.

The pharmaceutical composition according to the present disclosure also can be prepared in various forms, such as solid, liquid, gaseous or lyophilized forms, particularly the pharmaceutical composition can be prepared in the form of ointment, cream, transdermal patch, gel, powder, tablet, solution, aerosol, granule, pill, suspension, emulsion, capsule, syrup, elixir, extract, tincture or liquid extract, or in a form particularly suitable for the desired method of administration. Processes known in the present disclosure for producing a medicine may include, for example, conventional mixing, dissolving, granulating, dragee-making, grinding, emulsifying, encapsulating, embedding or lyophilizing process. The pharmaceutical composition comprising, for example, the immune cell as described herein is generally provided in a form of solution, and preferably comprises a pharmaceutically acceptable buffer agent.

The pharmaceutical composition according to the present disclosure may further be administered in combination with one or more other agents suitable for the treatment and/or prophylaxis of diseases to be treated. Preferred examples of agent suitable for the combination include known anti-cancer medicines such as cisplatin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate glucuronate, auristatin E, vincristine and doxorubicin; peptide cytotoxins, such as ricin, diphtheria toxin, pseudomonas exotoxin A, DNase and RNase; radionuclides such as iodine 131, rhenium 186, indium 111, iridium 90, bismuth 210, bismuth 213, actinides 225 and astatine 213; prodrugs such as antibody-directed enzyme prodrugs; immunostimulatory agents such as platelet factor 4, and melanoma growth stimulating protein and so on; antibodies or fragments thereof, such as anti-CD3 antibodies or fragments thereof, complement activators, heterologous protein domains, homologous protein domains, viral/bacterial protein domains and viral/bacterial peptides. In addition, the pharmaceutical composition of the present disclosure also can be used in combination with one or more other treatment methods, such as chemotherapy and radiotherapy.

Therapeutic Use

The present disclosure further provides a method of treating a subject with a disease associated with CD7 expression, comprising administering to the subject an effective amount of the immune cell or the pharmaceutical composition according to the present disclosure. Therefore, the present disclosure also encompasses use of the engineered immune cell and the pharmaceutical composition in the preparation of a medicine for treating diseases associated with CD7 expression.

In an embodiment, an effective amount of the immune cell and/or the pharmaceutical composition of the present disclosure is directly administered to the subject.

In another embodiment, the treatment method of the present disclosure is ex vivo treatment. Specifically, the method includes the steps of: (a) providing a sample, the sample containing an immune cell; (b) introducing the chimeric antigen receptor of the present disclosure and an exogenous gene (such as for a NK inhibitory molecule) into the immune cell in vitro, and suppressing or silencing the expression of specific genes (such as endogenous CD7, TCR/CD3 genes and MHC-II related genes) in the immune cell to obtain a modified immune cell, and (c) administering the modified immune cell to a subject in need thereof. Preferably, the immune cell provided in step (a) is selected from the group consisting of a macrophage, a dendritic cell, a monocyte, a T cell, a NK cell, and/or a NKT cell; and the immune cell can be obtained from a sample (particularly a blood sample) of the subject by conventional methods known in the art. However, other immune cells capable of expressing the chimeric antigen receptor of the present disclosure and exerting the desired biological effect function as described herein also can be used. Besides, the immune cells generally selected are compatible with the subject's immune system, i.e., it is preferred that the immune cells do not trigger an immunogenic response. For example, a "universal recipient cell", i.e., a universally compatible lymphocyte exerting a desired biological effect function and being capable of growing and amplifying in vitro, can be used. The use of such cells will not require obtaining and/or providing the subject's own lymphocyte. The ex vivo introduction of step (c) may be carried out by introducing the nucleic acid or vector described herein into the immune cell via electroporation or by infecting the immune cell with a viral vector, wherein the viral vector is a lentiviral vector, adenoviral vector, adeno-associated viral vector or retroviral vector as previously described. Other conceivable methods include using a transfection reagent (such as a liposome) or transient RNA transfection.

In an embodiment, the immune cell is an autologous or allogeneic cell, preferably T cell, macrophage, dendritic cell, monocyte, NK cell and/or NKT cell, more preferably T cell, NK cell or NKT cell.

As used herein, the term "autologous" means that any material derived from an individual will be later re-introduced into the same individual.

As used herein, the term "allogeneic" means that the material is derived from a different animal or different patient of the same species as the individual into which the material is introduced. When the genes at one or more loci are different, two or more individuals are considered allogeneic to each other. In some cases, genetic differences in allogeneic material from various individuals of the same species may be sufficient for antigen interactions to occur.

As used herein, the term "subject" refers to a mammal. The mammal may be, but is not limited to, a human, a non-human primate, a mouse, a rat, a dog, a cat, a horse, or a cow. Mammals other than human can be advantageously used as subjects representing cancer animal models. Preferably, the subject is a human.

In an embodiment, diseases associated with CD7 expression include non-solid tumors (such as hematological tumors, e.g., leukemias and lymphomas) and solid tumors. Hematological neoplasms are cancers of the blood or bone marrow, including but not limited to acute leukemias (such as acute lymphoblastic leukemia (ALL), acute myeloid leukemia (AML), acute myelogenous leukemia, and myeloblastic, promyelocytic, myelomonocytic, monocytic and erythroleukemia), chronic leukemia (such as chronic myeloid (granulocytic) leukemia, chronic myelogenous leukemia, and chronic lymphocytic leukemia), polycythemia vera, lymphoma, Hodgkin's lymphoma, non-Hodgkin's lymphoma (indolent and high-grade forms), multiple myeloma, Waldenstrom's macroglobulinemia, myelodysplastic syndrome, hairy cell leukemia, Burkitt's lymphoma, diffuse large cell lymphoma, mantle cell lymphoma, T-lymphoblastic lymphoma (T-LBL), early pro-T-lymphoblastic leukemia (ETP-ALL), extranodal NK/T-cell lymphoma, small lymphocytic lymphoma (SLL) and myelodysplasia. Solid tumors are abnormal masses of tissue that usually do not comprise cysts or areas of fluid, and can be benign or malignant. The different types of solid tumors are named according to the type of cells that form them (such as sarcomas, carcinomas, and lymphomas). Examples of solid tumors include, but are not limited to, fibrosarcoma, myxosarcoma, liposarcoma, mesothelioma, pancreatic cancer, ovarian cancer, peritoneal, omental, and mesenteric cancer, pharyngeal cancer, prostate cancer, rectal cancer, renal cancer, skin cancer, small intestine cancer, melanoma, kidney cancer, laryngeal cancer, soft tissue cancer, stomach cancer, testicular cancer, colon cancer, esophagus cancer, cervical cancer, alveolar rhabdomyosarcoma, bladder cancer, bone cancer, brain cancer, breast cancer, anal cancer, eye cancer, intrahepatic cholangiocarcinoma, joint cancer, neck cancer, gallbladder cancer, pleural cancer, nasal cancer, middle ear cancer, oral cancer, vulvar cancer, thyroid cancer and ureter cancer.

In an embodiment, the disease associated with CD7 expression is preferably selected from the group consisting of acute lymphoblastic leukemia (ALL), acute myeloid leukemia (AML), T-lymphoblastic lymphoma (T-LBL), early pro-T lymphoblastic Leukemia (ETP-ALL) and extranodal NK/T cell lymphoma.

The present disclosure will be described in detail below with reference to the accompanying drawings and examples. It should be noted that those skilled in the art should understand that the drawings and the embodiments of the present disclosure are only for the purpose of illustration, and shall not constitute any limitation to the present disclosure. In the case of no contradiction, the embodiments in the present application and the features in the embodiments can be combined with each other.

EXAMPLE

Example 1. Preparation of Universal CAR T Cells Against CD7

Sequences encoding the following proteins were synthesized and cloned sequentially into the pLVX vector (Public Protein/Plasmid Library (PPL), Cat. No.: PPL00157-4a): CD8α signal peptide (SEQ ID NO: 36), anti-CD7 scFv (SEQ ID NO: 21), CD8α hinge region (SEQ ID NO: 38), CD8α transmembrane region (SEQ ID NO: 24), 4-1BB intracellular region (SEQ ID NO: 28), CD3 ζ intracellular signaling domain (SEQ ID NO: 30), and the correct insertion of the target sequences was confirmed by sequencing.

Three ml Opti-MEM (Gibco, Cat. No. 31985-070) was added to a sterile tube to dilute the above plasmid, and then packaging vector psPAX2 (Addgene, Cat. No. 12260) and envelope vector pMD2.G (Addgene, Cat. No. 12259) were added according to the ratio of plasmid:viral packaging vector:viral envelope vector=4:2:1. Then, 120 μl X-treme GENE HP DNA transfection reagent (Roche, Cat. No. 06366236001) was added, mixed immediately, and incubated at room temperature for 15 min, and then the plasmid/vector/transfection reagent mixture was added dropwise to the culture flask of 293T cells. Viruses were collected at 24 hours and 48 hours, pooled, and ultracentrifuged (25000 g, 4° C., 2.5 hours) to obtain concentrated lentiviruses.

Wild-type T cells were activated with DynaBeads CD3/CD28 CTS™ (Gibco, Cat. No. 40203D) and cultured at 37° C. and 5% $CO_2$ for 1 day. Then the TCR/CD3 component (specifically TRAC gene), CD7 gene and optional MHC-II related gene (specifically RFX5) in the wild-type T cells were knocked out using the CRISPR system to obtain TCR/CD7 double knockout dKO-T cells and TCR/CD7/RFX5 triple knockout tKO-T cells. Wild-type T cells without gene knockout (i.e., NT cells) were used as controls.

Using FITC Mouse Anti-Human CD3 ζ BD Pharmingen, Cat. No. 555916) antibody, PE mouse anti-human CD7 (biolegend Cat. No. 395604) and APC anti-human DR, DP, DQ (biolegend, Cat. No. 361714) antibodies, the gene editing efficiency of TCR/CD7/RFX5 in T cells was detected by flow cytometry, and the results are shown in Table 1.

TABLE 1

Gene expression efficiency in T cells

| Name | TCR/CD3 | CD7 | RFX5/MHC-II |
|---|---|---|---|
| dKO-T | 2.2% | 5.3% | 92% |
| tKO-T | 3% | 8.9% | 11.2% |
| NT | 98% | 94% | 92% |

It can be seen from Table 1 that the expression of related genes in dKO-T cells and tKO-T cells prepared in the present disclosure is effectively suppressed or silenced.

Figure 1:
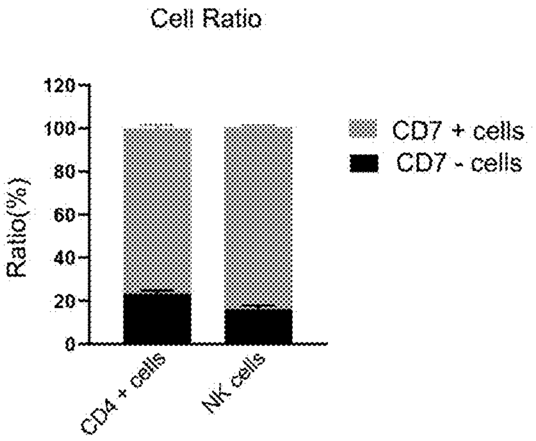
FIG. 1 shows the ratio of CD7+ cells and CD7−cells in peripheral blood lymphocytes of patients.
Figure 2:
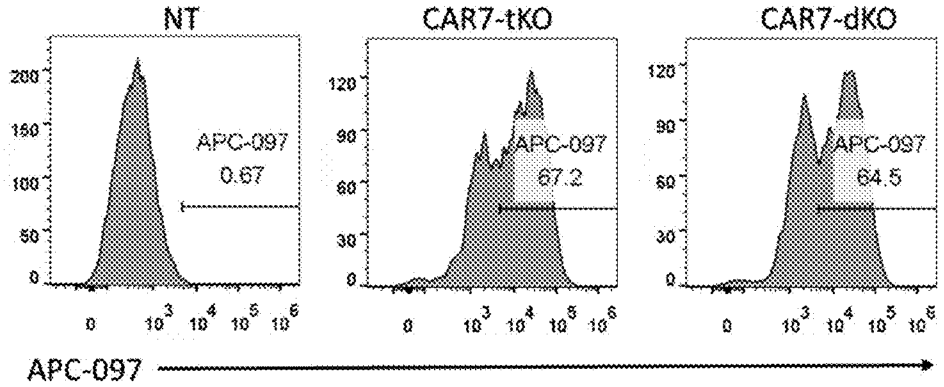
FIG. 2 shows the expression levels of scFv on the CAR7-dKO T cells and CAR7-tKO T cells.

The concentrated lentivirus was added to the dKO-T cells and tKO-T cells to obtain CAR7-dKO T cells and CAR7-tKO T cells. Using Biotin-SP (long spacer) AffiniPure Goat Anti-human IgG, $F(ab')_2$ Fragment Specific (min X Hu, Bov, Hrs Sr Prot) (jackson immunoresearch, Cat. No. 109-065-097) as the primary antibody, APC Streptavidin (BD Pharmingen, Cat. No. 554067) or PE Streptavidin (BD Pharmingen, Cat. No. 554061) as the secondary antibody, the expression levels of scFv on the CAR7-dKO T cells and CAR7-tKO T cells were detected by flow cytometry, and the results are shown in FIG. 2.

It can be seen that the scFv in the CAR T cells prepared by the present disclosure can be effectively expressed.

Figure 3:
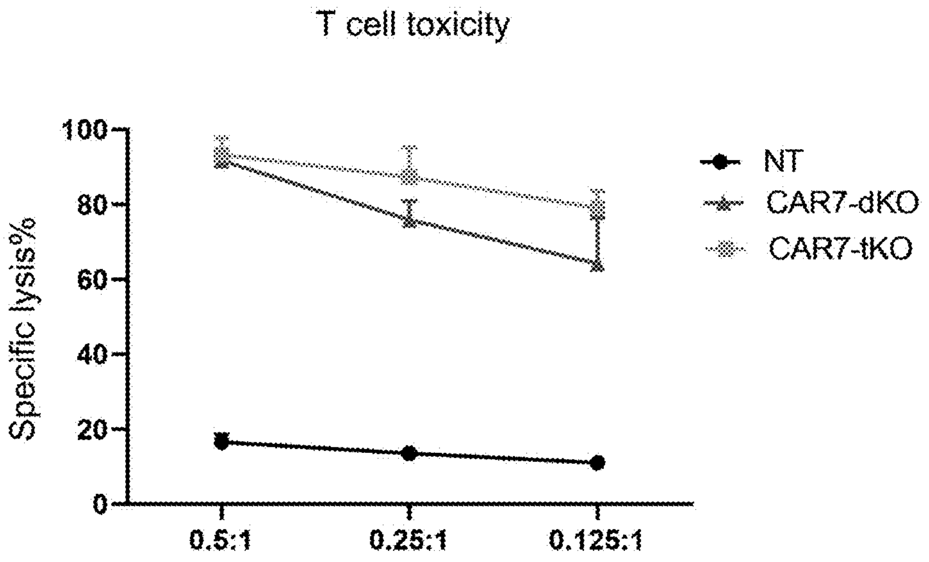
FIG. 3 shows the killing ability of CAR7-dKO T cells and CAR7-tKO T cells on target cells.

Example 2. Killing Effect of CAR T Cells on Target Cells and Release of Cytokines Thereof 2.1 Killing Effect of CAR-T Cells on Target Cells In order to detect the killing ability of CAR-T cells on target cells, firstly Jurkat target cells carrying the fluorescein gene were plated into a 96-well plate at $1\times10^4$/well, and then CAR T cells and NT cells were plated into the 96-well plate with effector-target ratios (i.e., the ratio of effector T cells to target cells) of 0.5:1, 0.25:1 and 0.125:1 for co-culture, and the fluorescence value was measured with a microplate reader after 16-18 hours. According to the calculation formula: (average fluorescence value of target cells−average fluorescence value of samples)/average fluorescence value of target cells×100%, the killing efficiency was calculated, and the results are shown in FIG. 3.

It can be seen that compared with NT, both CAR7-dKO T cells and CAR7-tKO T cells have specific killing ability on target cells, and the killing ability of CAR7-tKO T cells is higher than that of CAR7-dKO T cells.

2.2 Cytokine Release of CAR-T Cells

When T cells kill target cells, cytokines are released while the number of target cells is reduced. According to the following steps, enzyme-linked immunosorbent assay (ELISA) was used to measure the release level of cytokine IFNγ when the CAR T cells of the present disclosure kill target cells.

(1) Collection of Cell Co-Culture Supernatant

Jurkat target cells were plated in a 96-well plate at $1\times10^5$/well, and then CAR T and NT cells (negative control) were co-cultured with the target cells at a ratio of 0.125:1, and the cell co-culture supernatant was collected after 18-24 hours.

(2) Detection of the Secretion of IFN γ in the Supernatant by ELISA

Figure 4:
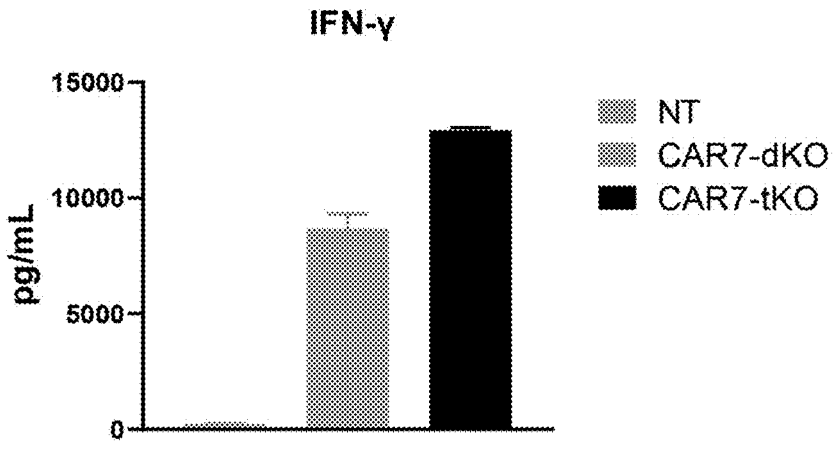
FIG. 4 shows the cytokine release levels after CAR7-dKO T cells and CAR7-tKO T cells were co-cultured with target cells.

A 96-well plate was coated with Purified anti-human IFN-γ Antibody (Biolegend, Cat. No. 506502) as capture antibody and incubated overnight at 4° C., and then the antibody solution was removed. 250 μL of PBST (1×PBS comprising 0.1% Tween) solution comprising 2% BSA (sigma, Cat. No. V900933-1 kg) was added, and incubated at 37° C. for 2 hours. The plate was then washed 3 times with 250 μL of PBST (1×PBS comprising 0.1% Tween). 50 μL of cell co-culture supernatant or standard per well was added and incubated at 37° C. for 1 hour, then the plate was washed 3 times with 250 μL of PBST (1×PBS comprising 0.1% Tween). Then 50 μL of Anti-Interferon gamma antibody [MD-1] (Biotin) (abcam, Cat. No. ab25017) as detection antibody, was added to each well, incubated at 37° C. for 1 hour, and the plate was washed 3 times with 250 μL of PBST (1×PBS comprising 0.1% Tween). Then HRP Streptavidin (Biolegend, Cat. No. 405210) was added, incubated at 37° C. for 30 minutes, and the supernatant was discarded. 250 μL of PBST (1×PBS comprising 0.1% Tween) was added for washing 5 times. 50 μL of TMB substrate solution was added to each well. Reactions were allowed to occur at room temperature in the dark for 30 minutes, after which 50 μL of 1 mol/L $H_2SO_4$ was added to each well to terminate the reaction. Within 30 minutes after the reaction termination, a microplate reader was used to detect the absorbance at 450 nm, and the content of cytokines was calculated according to the standard curve (drawn according to the reading value and concentration of the standard), the results are shown in FIG. 4.

It can be seen that the cytokine release of CAR7-dKO T cells and CAR7-tKO T cells to target cells was significantly higher than that of the control NT group, and the release level of CAR7-tKO T cells was higher than that of CAR7-dKO T cells.

From the above results, it can be seen that the killing ability of CAR7-tKO T cells on target cells and the release level of cytokines are higher than those of CAR7-dKO T cells, indicating that knockout of MHC-II genes enhances CAR-T cell killing activity. This is unexpected, because existing reports generally believe that the expression of MHC-II genes is related to immune rejection, and there has not been any report on the relationship between MHC-II genes and the activity of CAR-T cells themselves.

Example 3. Inhibitory Effect of NK Inhibitory Molecules on NK Cell Killing Activity The coding sequences of the following proteins were synthesized and cloned sequentially into the pLVX vector (Public Protein/Plasmid Library (PPL), Cat. No.: PPL00157-4a): B2m signal peptide (SEQ ID NO: 34), NK inhibitory ligand, CD28 hinge region (SEQ ID NO: 40), CD28 transmembrane region (SEQ ID NO: 24), wherein the NK inhibitory ligand is an extracellular region of E-cadherin (SEQ ID NO: 47, corresponding to the ECad0 plasmid), a fusion molecule of B2M and HLA-E extracellular region (comprising presenting peptide SEQ ID NO: 75, B2M SEQ ID NO: 74 and HLA-E extracellular region mutant SEQ ID NO: 51, wherein the coding sequence of B2M, SEQ ID NO: 82, comprises a synonymous mutation, corresponding to the E0 plasmid) or a fusion molecule of B2M and HLA-G extracellular region (comprising B2M SEQ ID NO: 74 and HLA-G extracellular region SEQ ID NO: 49, wherein the coding sequence of B2M, SEQ ID NO: 82, comprises a synonymous mutation, corresponding to the G0 plasmid). The CD28 co-stimulatory domain (SEQ ID NO: 26) was further included in the ECad0, E0 and G0 plasmids to obtain the ECad28, E28 and G28 plasmids, respectively. The correct insertion of the target sequences in the plasmid was confirmed by sequencing.

The coding sequences of the following proteins were synthesized and cloned sequentially into the pLVX vector (Public Protein/Plasmid Library (PPL), Cat. No.: PPL00157-4a): B2m signal peptide (SEQ ID NO: 34), NK inhibitory ligand, IgG4 hinge region (SEQ ID NO: 42), CD8α transmembrane region (SEQ ID NO: 22), CD28 co-stimulatory domain (SEQ ID NO: 26), wherein the NK inhibitory ligand is anti-NKG2A scFv (SEQ ID NO: 63, corresponding to A28 plasmid), anti-KIR scFv (SEQ ID NO: 67, corresponding to KIRG4 plasmid) or anti-LIR1 scFv (SEQ ID NO: 70, corresponding to LIR1-1 plasmid). The correct insertion of the target sequences in the plasmid was confirmed by sequencing.

The coding sequences of the following proteins were synthesized and cloned sequentially into the pLVX vector (Public Protein/Plasmid Library (PPL), Cat. No.: PPL00157-4a): CD8α signal peptide (SEQ ID NO: 36), anti-LIR1 scFv (SEQ ID NO: 73), CD28 hinge region (SEQ ID NO: 40), CD28 transmembrane region (SEQ ID NO: 24), 4-1BB co-stimulatory domain (SEQ ID NO: 28), to obtain a LIR1-2 plasmid. The correct insertion of the target sequences in the plasmid was confirmed by sequencing.

Three ml Opti-MEM (Gibco, Cat. No. 31985-070) was added to a sterile tube to dilute the above plasmid, and then packaging vector psPAX2 (Addgene, Cat. No. 12260) and envelope vector pMD2.G (Addgene, Cat. No. 12259) were added according to the ratio of plasmid:viral packaging vector:viral envelope vector=4:2:1. Then, 120 μl X-treme GENE HP DNA transfection reagent (Roche, Cat. No. 06366236001) was added, mixed immediately, and incubated at room temperature for 15 min, and then the plasmid/vector/transfection reagent mixture was added dropwise to the culture flask of 293T cells. Viruses were collected at 24 hours and 48 hours, pooled, and ultracentrifuged (25000 g, 4° C., 2.5 hours) to obtain concentrated lentiviruses.

T cells were activated with DynaBeads CD3/CD28 CTS™ (Gibco, Cat. No. 40203D) and cultured at 37° C. and 5% $CO_2$ for 1 day. Then, the concentrated lentivirus was added, and after continuous culture for 3 days, T cells expressing NK inhibitory molecules, i.e., UNKi-T cells, were obtained.

Then the TCR/CD3 component (specifically TRAC gene) and MHC-related genes (specifically B2M and RFX5) in wild-type T cells (Mock T cells, used as a control) and the UNKi-T cells were knocked out using the CRISPR system, and it is confirmed that each gene was effectively knocked out by flow cytometry.

Then, the inhibitory effect of the UNKi-T cells prepared in the present disclosure on the killing effect of NK cells was detected according to the following method: the UNKi-T cells and Mock-T cells prepared in the present disclosure were labeled with Far-Red (invitrogen, Cat. No. C34564). Then the labeled UNKi-T cells and Mock T cells were plated into 96-well plates at a concentration of $1\times10^4$ cells/well, and NK92 cells (for UNKi-T cells expressing HLA-E extracellular region, HLA-G extracellular region, anti-NKG2A scFv, anti-KIR scFv or anti-LIR1 scFv and Mock T cells) or NK92-KLRG1 cells (for UNKi-T cells expressing E-cadherin extracellular region, prepared by introducing the KLRG1 gene into NK92 cells) were added at an effector-target ratio of 2:1 for co-culture. After 16-18 hours, the proportion of T cells in the culture was detected by flow cytometry, and then the killing effect of NK cells on T cells was calculated. The results are shown in FIG. 5.

Figure 5:
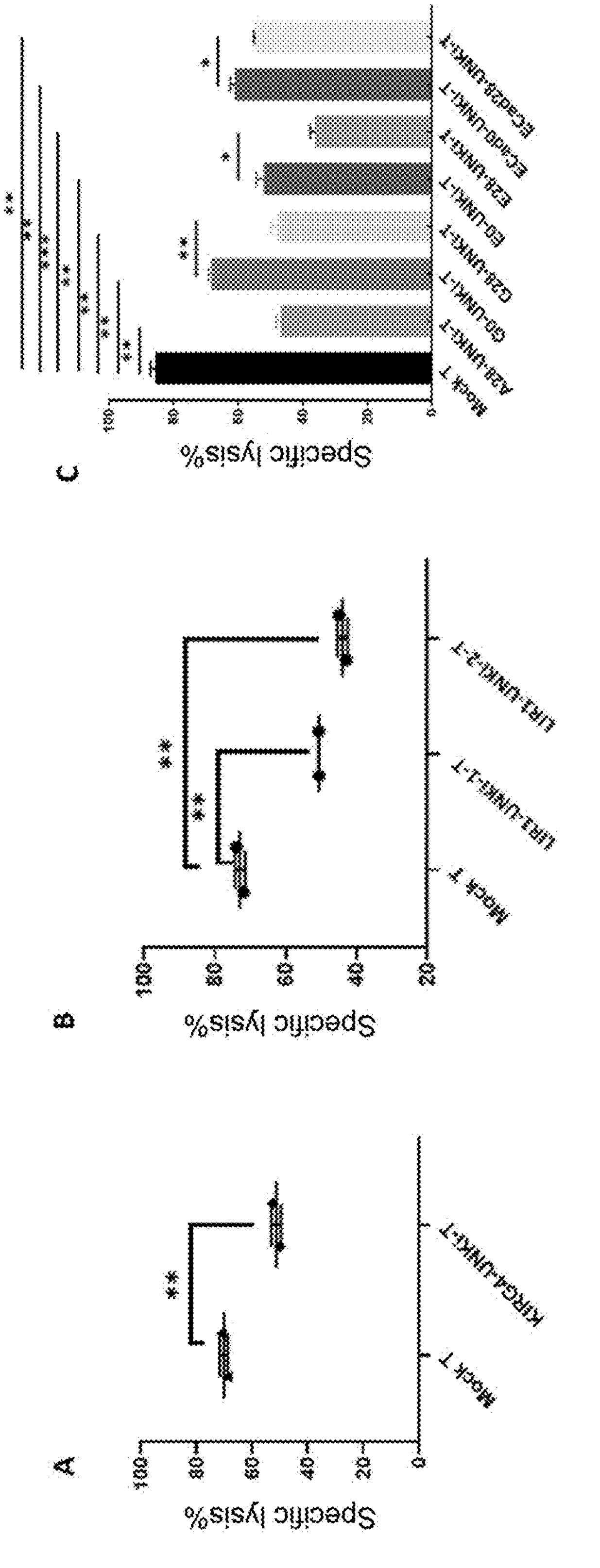
FIG. 5 shows the inhibitory effect of NK inhibitory molecules on NK cell killing ability. A: a NK inhibitory molecule comprises anti-KIR scFv; B: a NK inhibitory molecule comprises anti-LIR scFv; C: a NK inhibitory molecule comprises anti-NKG2A scFv, a HLA-G extracellular region, a HLA-E extracellular region or an E-Cad extracellular region.

It can be seen from FIG. 5 that compared with Mock T cells that do not express NK inhibitory molecules, UNKi-T cells expressing inhibitory ligands such as anti-KIR scFv, anti-LIR1 scFv, anti-NKG2A scFv, HLA-G extracellular region, HLA-E extracellular region and E-cadherin extracellular region can significantly reduce the killing effect of NK cells on T cells. In addition, compared with T cells (G0, E0, Ecad0) expressing only an inhibitory ligand and a transmembrane domain (i.e., not comprising a co-stimulatory domain), the addition of the co-stimulatory domain can further significantly enhance the inhibition of killing effect of NK cell on T cells (G28, E28, ECad28). Therefore, the NK inhibitory molecules comprising an inhibitory ligand, a transmembrane domain and a co-stimulatory domain of the present disclosure can significantly reduce the killing effect of NK cells on UNKi-T cells, thereby effectively reducing the risk of HvGD.

In addition, in some cases, it is not only necessary to inhibit the killing effect of NK cells on CAR-T cells, but even further requires T cells to kill NK cells. Therefore, the inventors further included the CD3 ζ intracellular signaling domain (SEQ ID NO: 30) on the basis of the E28 plasmid and A28 plasmid cells, and packaged them as lentivirus according to the above method, and infected T cells in which TCR/CD3 components (specifically TRAC gene) and MHC-related genes (specifically B2M and RFX5) were effectively knocked out, to obtain E28z-UNKi-T cells and A28z-UNKi-T cells.

Figure 6:
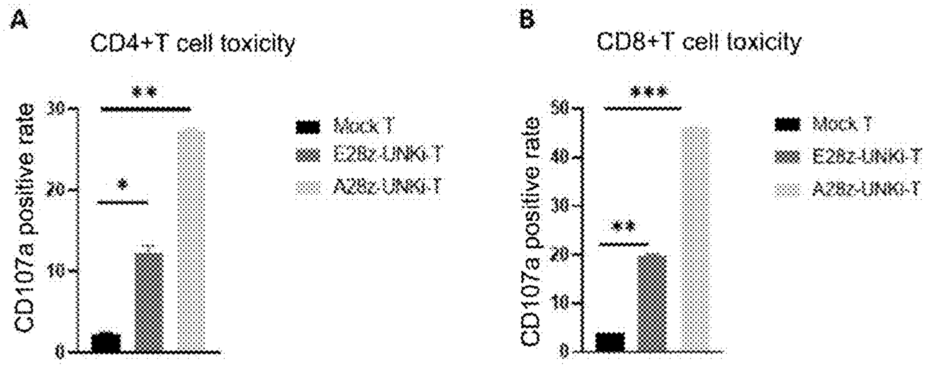
FIG. 6 shows the killing effect of CD4+ T cells (A) and CD8+ T cells (B) expressing NK inhibitory molecules comprising CD3 ζ on NK cells.

The killing of NK cells by UNKi-T cells was detected by the following method: the target cells (NK92 cells) were plated in a 96-well plate at a concentration of $1\times10^5$ cells/well, and then Mock T cells, E28z-UNKi-T cells and A28z-UNKi-T cells were added to each well at a ratio of 1:1, and at the same time, 10 µl of PE-anti-human CD107a (BD Pharmingen, Cat. No. 555801) was added for co-culturing at 37° C. and 5% $CO_2$. After 1 hour, Goigstop (BD Pharmingen, Cat. No. 51-2092KZ) was added to continue incubation for 2.5 hours. Then 5 µl APC-anti human CD8 (BD Pharmingen, Cat. No.: 555369) and 5 µl FITC-anti human CD4 (BD Pharmingen, Cat. No.: 561005) were added to each well, and incubated at 37° C. for 30 minutes. The expression of CD107a was detected by flow cytometry, and the results are shown in FIG. 6A (CD4+ T cell toxicity) and FIG. 6B (CD8+ T cell toxicity).

It can be seen that Mock T cells that do not express NK inhibitory molecules hardly kill target cells. On the contrary, after the E28z-UNKi-T cells and A28z-UNKi-T cells prepared by the present disclosure were co-cultured with the target cells, the expression rate of CD107a was significantly increased, indicating that the UNKi-T cells of the present disclosure can significantly kill NK cells.

Example 4. Preparation of Universal CAR T Cells Expressing NK Inhibitory Molecules Sequences encoding the following proteins were synthesized and cloned into the MSCV vector: CD8α signal peptide (SEQ ID NO: 36), anti-CD7 scFv (SEQ ID NO: 21), CD8α hinge region (SEQ ID NO: 38), CD8α transmembrane region (SEQ ID NO: 22), 4-1BB intracellular region (SEQ ID NO: 28), CD3 ζ intracellular signaling domain (SEQ ID NO: 30), F2A, E-cadherin extracellular region (SEQ ID NO: 48), CD28 hinge region (SEQ ID NO: 40), CD28 transmembrane region (SEQ ID NO: 24) and CD28 intracellular region (SEQ ID NO: 26), and the correct insertion of the target sequences was confirmed by sequencing.

Three ml Opti-MEM (Gibco, Cat. No. 31985-070) was added to a sterile tube to dilute the above plasmid, and then packaging vector pCL-Eco (Shanghai Hewu Biotechnology Co., Ltd., Cat. No. P3029) was added according to the ratio of plasmid:viral packaging vector=3:1. Then, 120 µl X-treme GENE HP DNA transfection reagent (Roche, Cat. No. 06366236001) was added, mixed immediately, and incubated at room temperature for 15 min, and then the plasmid/vector/transfection reagent mixture was added dropwise to the culture flask of 293 GP cells. Viruses were collected at 72 hours and 96 hours, pooled, centrifuged (2000 rpm, 4° C., 10 min) to remove fragments and obtain retroviral supernatant.

TCR/CD7 double-knockout dKO T cells and TCR/CD7/RFX5 triple-knockout tKO T cells were prepared according to the knockout method in Example 1. Wild-type T cells without gene knockout (i.e., NT cells) were used as controls.

A 24-well plate was coated with Retronectin and incubated overnight at 4° C. Then the solution was removed, and 300 µL of PBS solution comprising 5% FBS (Gibco, Cat. No.) was added and left at room temperature for 30 min. The supernatant was then removed and the plate was washed 2 times with 1 mL of PBS. 2 mL retrovirus supernatant and 0.5M dKO-T cells or tKO-T cells were added to each well, centrifuged at 2000 g and 32° C. for 2h and cultured in a carbon dioxide incubator to obtain CAR7-NKi-dKO T cells and CAR7-NKi-tKO T cells.

Figure 7:
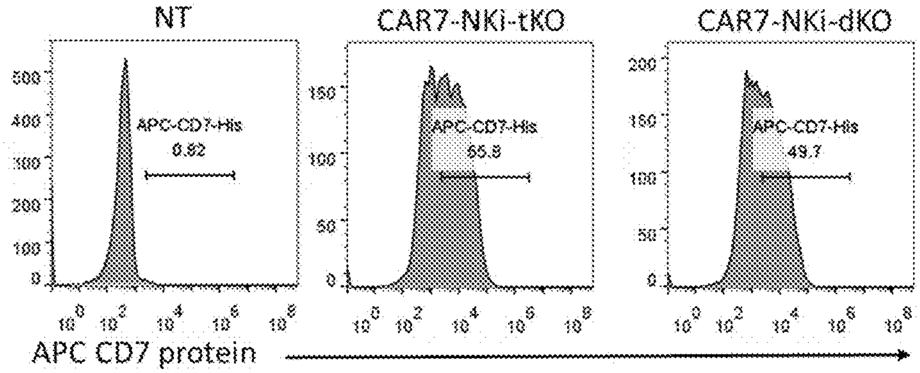
FIG. 7 shows the expression levels of scFv on CAR7-NKi-dKO T cells and CAR7-NKi-tKO T cells.

After 7 days of culture, using Biotin-SP (long spacer) AffiniPure Goat Anti-Mouse IgG, F(ab')$_2$ Fragment Specific (min X Hu, Bov, Hrs Sr Prot) (jackson immunoresearch, Cat. No. 115-065-072) as the primary antibody, APC Streptavidin (BD Pharmingen, Cat. No. 554067) or PE Streptavidin (BD Pharmingen, Cat. No. 554061) as the secondary antibody, the expression levels of CD7 scFv in the CAR7-NKi-dKO T cells and CAR7-NKi-tKO T cells were detected by flow cytometry, and the results are shown in FIG. 7. The expression of E-Cadherin in CAR T cells was detected using E-cadherin monoclonal antibody (Invitrogen, Cat. No.

Figure 8:
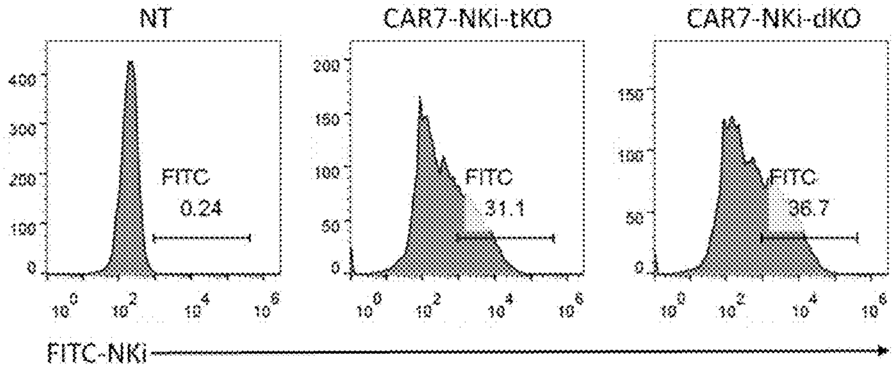
FIG. 8 shows the expression levels of NK inhibitory molecules of CAR7-NKi-dKO T cells and CAR7-NKi-tKO T cells.

13-5700) and Goat anti-Mouse IgG (H+L) Cross-Adsorbed Secondary Antibody, Alexa Fluor 488 (Invitrogen, Cat. No. A-11001), and the results are shown in FIG. 8.

It can be seen that both anti-CD7 scFv and NKi inhibitory molecules can be effectively expressed in the CAR T cells prepared in the present disclosure.

Figure 9:
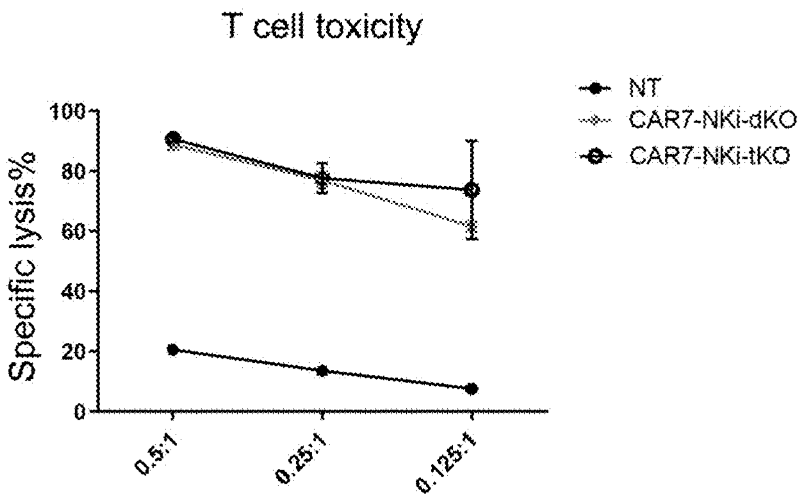
FIG. 9 shows the killing ability of CAR7-NKi-dKO T cells and CAR7-NKi-tKO T cells on target cells.

The killing effect of CAR7-NKi-dKO T cells and CAR7-NKi-tKO T cells on Jurkat target cells was detected according to the method described in 2.1 of Example 2, and the results are shown in FIG. 9. It can be seen that the two CAR-T cells can significantly kill target cells at various effector-target ratios, and at the effector-target ratio of 0.125:1, the killing effect of CAR7-NKi-tKO T cells is better than that of CAR7-NKi-dKO T cells.

Figure 10:
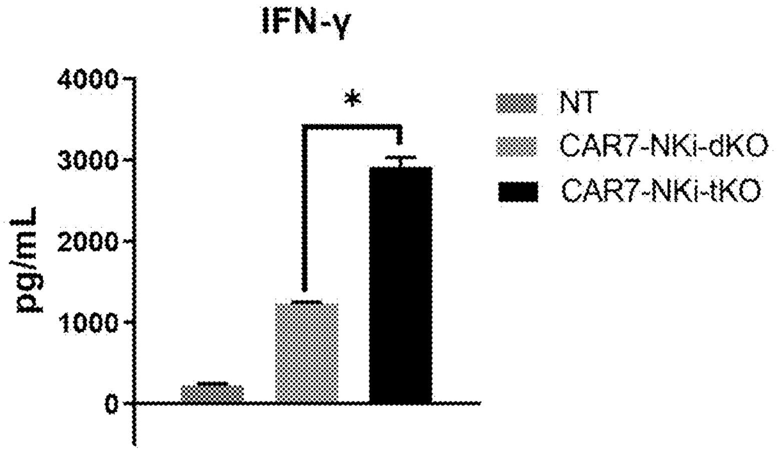
FIG. 10 shows the cytokine release levels after CAR7-NKi-dKO T cells and CAR7-NKi-tKO T cells were co-cultured with target cells.

The cytokine release levels after CAR7-NKi-dKO T cells and CAR7-NKi-tKO T cells were co-cultured with Jurkat target cells were detected according to the method described in 2.2 of Example 2, and the results are shown in FIG. 10. It can be seen that the cytokine release levels of the CAR7-NKi-dKO T cells and CAR7-NKi-tKO T cells of the present disclosure were significantly higher than those of the control NT cells, and the release level of CAR7-NKi-tKO T cell group was significantly higher than that of CAR7-NKi-dKO T cell group.

Example 5. Preparation of Universal CAR T Cells Expressing NK Inhibitory Molecules and Verification of their Functions Sequences encoding the following proteins were synthesized and cloned into the MSCV vector: CD8α signal peptide (SEQ ID NO: 36), anti-CD7 scFv (SEQ ID NO: 21), CD28 hinge region (SEQ ID NO: 40), CD8α transmembrane region (SEQ ID NO: 22), CD28 intracellular region (SEQ ID NO: 26), CD3 ζ intracellular signaling domain (SEQ ID NO: 32), F2A, PD-L1 signal peptide (SEQ ID NO: 44), PD-L1 extracellular region (SEQ ID NO: 45), CD28 transmembrane region (SEQ ID NO: 24), 4-1BB intracellular region (SEQ ID NO: 28), and the correct insertion of the target sequences was confirmed by sequencing (plasmid designation: CAR7-PDL1).

Sequences encoding the following proteins were synthesized and cloned into the MSCV vector: CD8α signal peptide (SEQ ID NO: 36), anti-CD7 scFv (SEQ ID NO: 21), CD8α hinge region (SEQ ID NO: 38), CD28 transmembrane region (SEQ ID NO: 24), 4-1BB intracellular region (SEQ ID NO: 28), CD3 ζ intracellular signaling domain (SEQ ID NO: 32), F2A, B2M signal peptide (SEQ ID NO: 34), HLA-E extracellular region (SEQ ID NO: 50), CD28 transmembrane region (SEQ ID NO: 24), CD28 intracellular region (SEQ ID NO: 26), and the correct insertion of the target sequences was confirmed by sequencing (Plasmid designation: CAR7-E).

Sequences encoding the following proteins were synthesized and cloned into the MSCV vector: CD8α signal peptide (SEQ ID NO: 36), anti-CD7 scFv (SEQ ID NO: 21), CD8α hinge region (SEQ ID NO: 38), CD8α transmembrane region (SEQ ID NO: 22), 4-1BB intracellular region (SEQ ID NO: 28), CD3 ζ intracellular signaling domain (SEQ ID NO: 32), F2A, B2M signal peptide (SEQ ID NO: 34), HLA-E extracellular region (SEQ ID NO: 50), linker peptide (SEQ ID NO: 64), PD-L1 extracellular region (SEQ ID NO: 45), CD28 transmembrane region (SEQ ID NO: 24), CD28 intracellular region (SEQ ID NO: 26), and the correct insertion of the target sequences was confirmed by sequencing (plasmid designation: CAR7-EPDL1).

According to the method described in Example 3, the above plasmids were packaged into retroviruses and infected into tKO-T cells to obtain CAR7-E T cells, CAR7-PDL1 T cells and CAR7-EPDL1 T cells, respectively.

Figure 11:
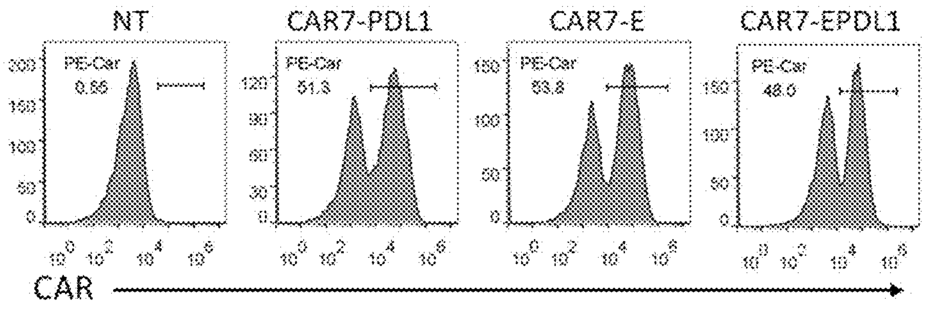
FIG. 11 shows the expression levels of scFv on CAR7-E T cells, CAR7-PDL1 T cells and CAR7-EPDL1 T cells.
Figure 12:
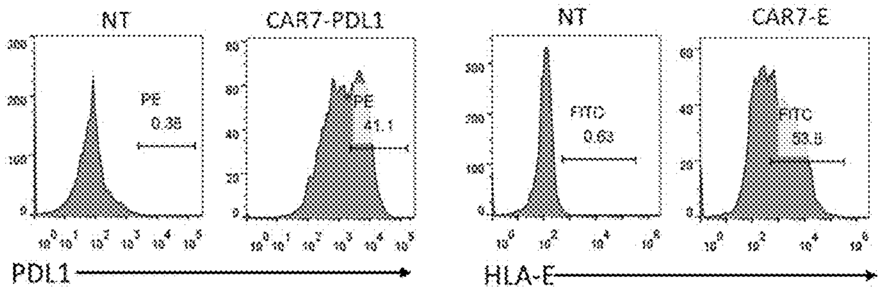
FIG. 12 shows the expression level of HLA-E in CAR7-E T cells and the expression level of PDL1 in CAR7-PDL1 T cells.
Figure 13:
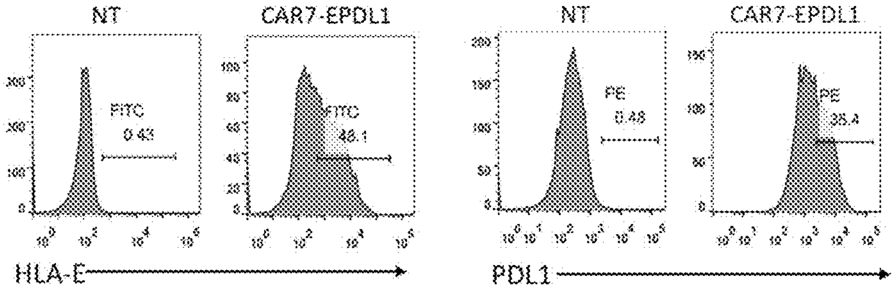
FIG. 13 shows the expression levels of HLA-E and PDL1 in CAR7-EPDL1 T cells.

After 7 days of culture, using Biotin-SP (long spacer) AffiniPure Goat Anti-human IgG, F(ab')$_2$ Fragment Specific (min X Hu, Bov, Hrs Sr Prot) (jackson immunoresearch, Cat. No. 109-065-097) as the primary antibody, APC Streptavidin (BD Pharmingen, Cat. No. 554067) or PE Streptavidin (BD Pharmingen, Cat. No. 554061) as the secondary antibody, the expression levels of scFv in the three cells were detected by flow cytometry, and the results are shown in FIG. 11. The expression of HLA-E and PDL1 in CAR T cells was detected using PE mouse anti-human HLA-E (biolegend, Cat. No. 342604) and PE anti-human PDL1 (biolegend, Cat. No. 329706), respectively, and the results are shown in FIG. 12 and FIG. 13.

It can be seen that both anti-CD7 scFv and NK inhibitory molecules (HLA-E and PD-L1) can be effectively expressed in the CAR T cells prepared in the present disclosure.

Figure 14:
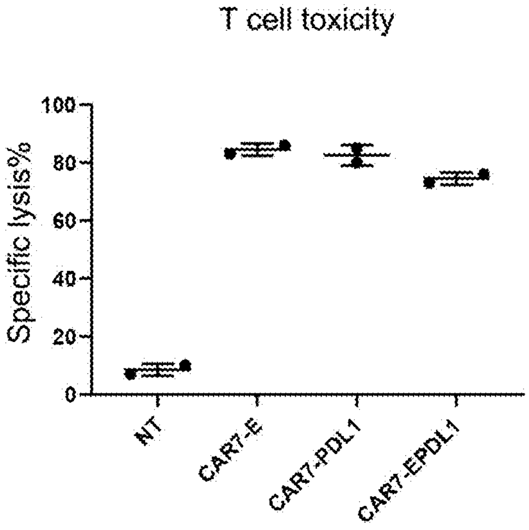
FIG. 14 shows the killing ability of CAR7-E T cells, CAR7-PDL1 T cells and CAR7-EPDL1 T cells on target cells.

According to the method described in 2.1 of Example 2, the killing effect of three CAR-T cells on Jurkat target cells was detected, and the results are shown in FIG. 14. It can be seen that all three CAR-T cells can significantly kill target cells.

Figure 15:
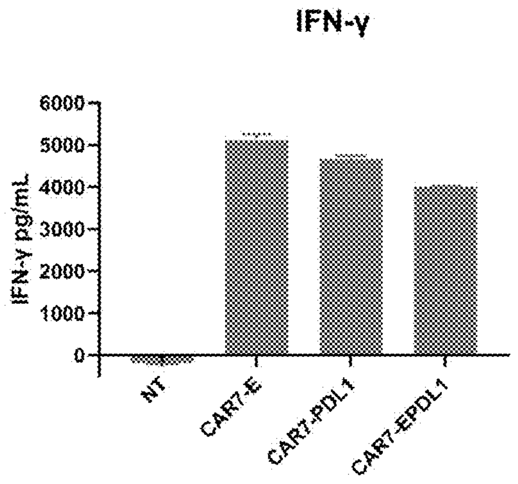
FIG. 15 shows the cytokine release levels after CAR7-E T cells, CAR7-PDL1 T cells and CAR7-EPDL1 T cells were co-cultured with target cells.

According to the method described in 2.2 of Example 2, the cytokine release levels after the three CAR-T cells were co-cultured with Jurkat target cells were detected, and the results are shown in FIG. 15. Compared with the NT group, the cytokine release levels of the three CAR-T cells were significantly increased.

Example 6. Preparation of Dual-Target CAR-T Cells and Verification of their Functions Sequences encoding the following proteins were synthesized and cloned into the pLVX vector (Public Protein/Plasmid Library (PPL), Cat. No.: PPL00157-4a): CD8α signal peptide (SEQ ID NO: 36), anti-CD7 scFv (SEQ ID NO: 20), linker peptide (SEQ ID NO: 64), anti-CD19 scFv (SEQ ID NO: 54), CD8α hinge region (SEQ ID NO: 38), CD8α transmembrane region (SEQ ID NO: 22), 4-1BB intracellular region (SEQ ID NO: 28), CD3 ζ intracellular signaling domain (SEQ ID NO: 32), and the correct insertion of the target sequences was confirmed by sequencing.

According to the method of Example 1, the above plasmid vectors were packaged into lentivirus, and infected into tkO-T cells to obtain CAR7-19 T cells. Unmodified wild-type T cells were used as negative controls (NT).

Figure 16:
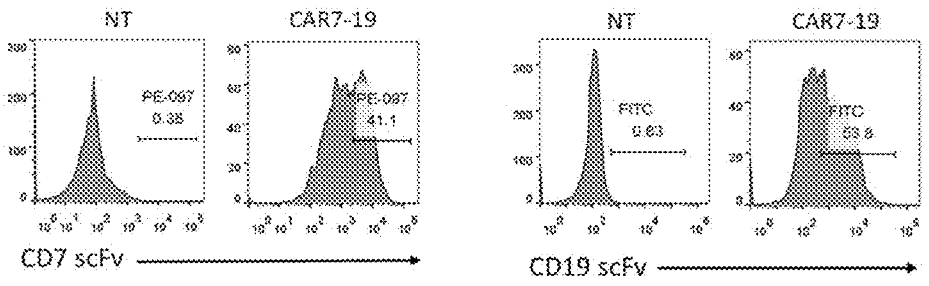
FIG. 16 shows the expression levels of CD7 scFv and CD19 scFv in CAR7-19 T cells.

Using Biotin-SP (long spacer) AffiniPure Goat Anti-Mouse IgG, F(ab')$_2$ Fragment Specific (min X Hu, Bov, Hrs Sr Prot) (jackson immunoresearch, Cat. No. 115-065-072) or Biotin-SP (long spacer) AffiniPure Goat Anti-human IgG, F(ab')$_2$ Fragment Specific (min X Hu, Bov, Hrs Sr Prot) (jackson immunoresearch, Cat. No. 109-065-097) as the primary antibody, FITC Streptavidin (BD Pharmingen, Cat. No. 554060) or PE Streptavidin (BD Pharmingen, Cat. No. 554061) as the secondary antibody, the expression level of scFv in CAR7-19 T cells was detected by flow cytometry, and the results are shown in FIG. 16.

It can be seen that both CD7 scFv and CD19 scFv can be effectively expressed in the CAR T cells prepared in the present disclosure.

Figure 17:
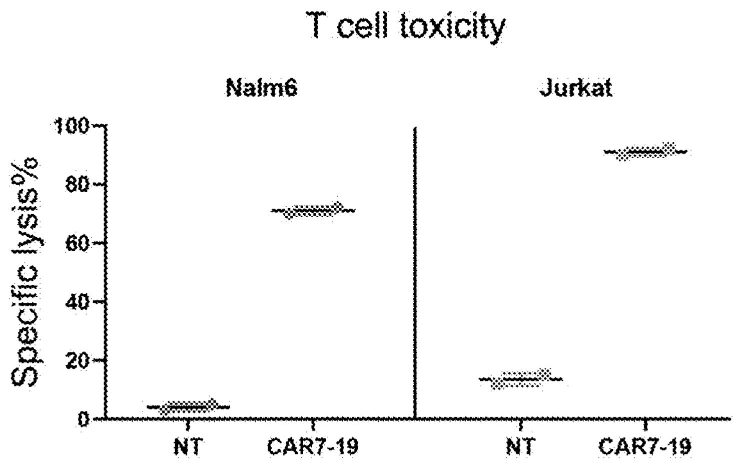
FIG. 17 shows the killing ability of CAR7-19 T cells on two target cells.
Figure 18:
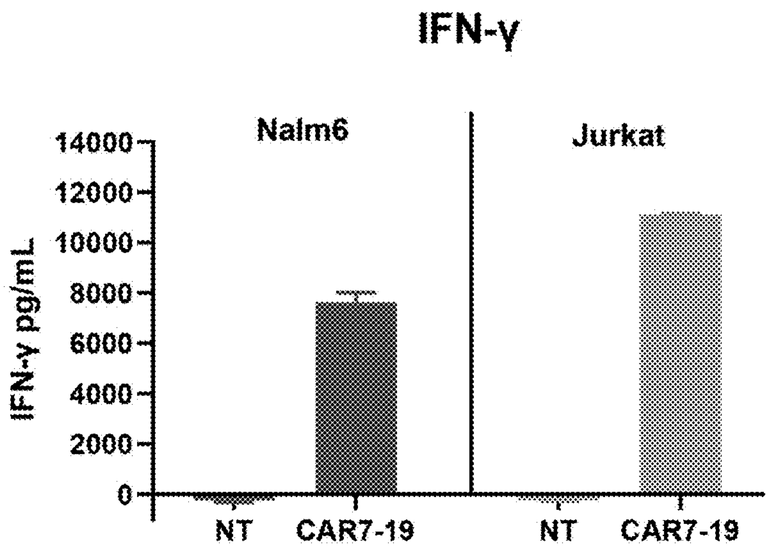
FIG. 18 shows the cytokine release levels after CAR7-19 T cells were co-cultured with two kinds of target cells.

According to the method in Example 2, the killing function and cytokine release level of CAR7-19 T cells were detected, and the results are shown in FIG. 17 and FIG. 18, respectively. It can be seen that CAR7-19 T cells have specific killing effect on both Nalm6 and Jurkat target cells and significantly increased cytokine release.

It should be noted that the above-mentioned are merely for preferred examples of the present disclosure and not used to limit the present disclosure. For one skilled in the art, various modifications and changes may be made to the present disclosure. Those skilled in the art should understand that any amendments, equivalent replacements, improvements, and so on, made within the spirit and principle of the present disclosure, should be covered within the scope of protection of the present disclosure.

What is claimed is:

1. An engineered immune cell, (1) expressing a chimeric antigen receptor comprising an antigen-binding region, the antigen-binding region comprising an anti-CD7 antibody; and (2) having suppressed or silenced expression of endogenous CD7, at least one TCR/CD3 gene, and at least one MHC-II-related gene; wherein the engineered immune cell further expresses a NK inhibitory molecule, and the NK inhibitory molecule comprises one or more NK inhibitory ligands, a transmembrane domain and at least one co-stimulatory domain.

2. The engineered immune cell according to claim 1, wherein the chimeric antigen receptor comprises the anti-CD7 antibody, a transmembrane domain, and an intracellular signaling domain.

3. The engineered immune cell according to claim 1, wherein the anti-CD7 antibody comprises CDR-L1, CDR-L2 and CDR-L3 as set forth in SEQ ID NOs: 1, 2 and 3 respectively, and CDR-H1, CDR-H2 and CDR-H3 as set forth in SEQ ID NOs: 4, 5 and 6 respectively.

4. The engineered immune cell according to claim 1, wherein the antigen-binding region of the chimeric antigen receptor further comprises an antibody targeting a second antigen, or a functional fragment thereof, wherein the second antigen is CD19.

5. The engineered immune cell according to claim 1, wherein the chimeric antigen receptor comprises an anti-CD7 antibody and an anti-CD19 antibody.

6. The engineered immune cell according to claim 1, wherein the transmembrane domain is a transmembrane domain of a protein selected from the group consisting of: TCR α chain, TCR β chain, TCR γ chain, TCR δ chain, CD3 ζ subunit, CD3 ε subunit, CD3 γ subunit, CD3 δ subunit, CD45, CD4, CD5, CD8α, CD9, CD16, CD22, CD33, CD28, CD37, CD64, CD80, CD86, CD134, CD137 and CD154.

7. The engineered immune cell according to claim 1, wherein the intracellular signaling domain is an intracellular region of a protein selected from the group consisting of: FcR γ, FcR β, CD3 γ, CD3 δ, CD3 ε, CD3 ζ, CD22, CD79a, CD79b, and CD66d.

8. The engineered immune cell according to claim 1, wherein the chimeric antigen receptor further comprises at least one co-stimulatory domain, which is an intracellular region of a protein selected from the group consisting of: TLR1, TLR2, TLR3, TLR4, TLR5, TLR6, TLR7, TLR8, TLR9, TLR10, CARD11, CD2, CD7, CD8, CD18 (LFA-1), CD27, CD28, CD30, CD40, CD54 (ICAM), CD83, CD134 (OX40), CD137 (4-1BB), CD270 (HVEM), CD272 (BTLA), CD276 (B7-H3), CD278 (ICOS), CD357 (GITR), DAP10, DAP12, LAT, NKG2C, SLP76, PD-1, LIGHT, TRIM, ZAP70 and a combination thereof.

9. The engineered immune cell according to claim 1, wherein the TCR/CD3 gene is TRAC.

10. The engineered immune cell according to claim 1, wherein the MHC-II-related gene is RFX5.

11. The engineered immune cell according to claim 1, wherein the engineered immune cell has suppressed or silenced expression of endogenous CD7, at least one TCR/CD3 gene selected from the group consisting of TRAC and TRBC and at least one MHC class II gene selected from the group consisting of RFX5, RFXAP, RFXANK and CIITA.

12. The engineered immune cell according to claim 1, wherein the NK inhibitory ligand is an antibody targeting a NK inhibitory receptor or a functional fragment thereof.

13. The engineered immune cell according to claim 1, wherein the NK inhibitory ligand is HLA-E.

14. The engineered immune cell according to claim 1, wherein the NK inhibitory molecule further comprises a CD3 ζ intracellular region as the intracellular signaling domain.

15. The engineered immune cell according to claim 1, wherein the engineered immune cell is a T cell, a macrophage, a dendritic cell, a monocyte, a NK cell or a NKT cell.

16. A pharmaceutical composition comprising the engineered immune cell according to claim 1, and one or more pharmaceutically acceptable excipients.

17. A method for treating a subject with a disease associated with CD7 expression, comprising administering to the subject an effective amount of the engineered immune cell according to claim 1.

18. The method according to claim 17, the disease associated with CD7 expression is selected from the group consisting of acute lymphoblastic leukemia (ALL), acute myeloid leukemia (AML), T-lymphoblastic lymphoma (T-LBL), early pro-T lymphoblastic Leukemia (ETP-ALL) and extranodal NK/T cell lymphoma.

19. The engineered immune cell according to claim 12, wherein the NK inhibitory receptor is selected from the group consisting of NKG2A, NKG2B, CD94, LIR1, LIR2, LIR3, LIR5, LIR8, KIR2DL1, KIR2DL2/3, KIR2DL5A, KIR2DL5B, KIR3DL1, KIR3DL2, KIR3DL3, CEACAM1, LAIR1, NKR-P1B, NKR-P1D, PD-1, TIGIT, CD96, TIM3, LAG3, SIGLEC7, SIGLEC9, Ly49A, Ly49C, Ly49F, Ly49G1, Ly49G4 and KLRG1.

* * * * *

SEQUENCE LISTING

```
<160> NUMBER OF SEQ ID NOS: 82

<210> SEQ ID NO 1
<211> LENGTH: 11
<212> TYPE: PRT
<213> ORGANISM: Artificial Sequence
<220> FEATURE:
<223> OTHER INFORMATION: CDR-L1

<400> SEQUENCE: 1

Arg Ala Ser Gln Ser Ile Ser Asn Asn Leu His
1               5                   10


<210> SEQ ID NO 2
<211> LENGTH: 7
<212> TYPE: PRT
<213> ORGANISM: Artificial Sequence
<220> FEATURE:
<223> OTHER INFORMATION: CDR-L2

<400> SEQUENCE: 2

Ser Ala Ser Gln Ser Ile Ser
1               5


<210> SEQ ID NO 3
<211> LENGTH: 9
<212> TYPE: PRT
<213> ORGANISM: Artificial Sequence
<220> FEATURE:
<223> OTHER INFORMATION: CDR-L3

<400> SEQUENCE: 3

Gln Gln Ser Asn Ser Trp Pro Tyr Thr
1               5


<210> SEQ ID NO 4
<211> LENGTH: 7
<212> TYPE: PRT
<213> ORGANISM: Artificial Sequence
<220> FEATURE:
<223> OTHER INFORMATION: CDR-H1

<400> SEQUENCE: 4

Gly Tyr Thr Phe Thr Ser Tyr
1               5


<210> SEQ ID NO 5
<211> LENGTH: 6
<212> TYPE: PRT
<213> ORGANISM: Artificial Sequence
<220> FEATURE:
<223> OTHER INFORMATION: CDR-H2

<400> SEQUENCE: 5

Asn Pro Ser Asn Gly Arg
1               5


<210> SEQ ID NO 6
<211> LENGTH: 14
<212> TYPE: PRT
```

<213> ORGANISM: Artificial Sequence
<220> FEATURE:
<223> OTHER INFORMATION: CDR-H3

<400> SEQUENCE: 6

Gly Gly Val Tyr Tyr Asp Leu Tyr Tyr Tyr Ala Leu Asp Tyr
1 5 10

<210> SEQ ID NO 7
<211> LENGTH: 108
<212> TYPE: PRT
<213> ORGANISM: Artificial Sequence
<220> FEATURE:
<223> OTHER INFORMATION: m189 VL

<400> SEQUENCE: 7

Asp Ile Glu Leu Thr Gln Ser Pro Ala Thr Leu Ser Val Thr Pro Gly
1 5 10 15

Asp Ser Val Ser Leu Ser Cys Arg Ala Ser Gln Ser Ile Ser Asn Asn
20 25 30

Leu His Trp Tyr Gln Gln Lys Ser His Glu Ser Pro Arg Leu Leu Ile
35 40 45

Lys Ser Ala Ser Gln Ser Ile Ser Gly Ile Pro Ser Arg Phe Ser Gly
50 55 60

Ser Gly Ser Gly Thr Asp Phe Thr Leu Ser Ile Asn Ser Val Glu Thr
65 70 75 80

Glu Asp Phe Gly Met Tyr Phe Cys Gln Gln Ser Asn Ser Trp Pro Tyr
85 90 95

Thr Phe Gly Gly Gly Thr Lys Leu Glu Ile Lys Arg
100 105

<210> SEQ ID NO 8
<211> LENGTH: 123
<212> TYPE: PRT
<213> ORGANISM: Artificial Sequence
<220> FEATURE:
<223> OTHER INFORMATION: m189 VH

<400> SEQUENCE: 8

Gln Val Gln Leu Gln Glu Ser Gly Ala Glu Leu Val Lys Pro Gly Ala
1 5 10 15

Ser Val Lys Leu Ser Cys Lys Ala Ser Gly Tyr Thr Phe Thr Ser Tyr
20 25 30

Trp Met His Trp Val Lys Gln Arg Pro Gly Gln Gly Leu Glu Trp Ile
35 40 45

Gly Lys Ile Asn Pro Ser Asn Gly Arg Thr Asn Tyr Asn Glu Lys Phe
50 55 60

Lys Ser Lys Ala Thr Leu Thr Val Asp Lys Ser Ser Ser Thr Ala Tyr
65 70 75 80

Met Gln Leu Ser Ser Leu Thr Ser Glu Asp Ser Ala Val Tyr Tyr Cys
85 90 95

Ala Arg Gly Gly Val Tyr Tyr Asp Leu Tyr Tyr Tyr Ala Leu Asp Tyr
100 105 110

Trp Gly Gln Gly Thr Thr Val Thr Val Ser Ser
115 120

<210> SEQ ID NO 9
<211> LENGTH: 249
<212> TYPE: PRT
<213> ORGANISM: Artificial Sequence
<220> FEATURE:
<223> OTHER INFORMATION: m189 scFv

<400> SEQUENCE: 9

Asp Ile Glu Leu Thr Gln Ser Pro Ala Thr Leu Ser Val Thr Pro Gly
1 5 10 15

Asp Ser Val Ser Leu Ser Cys Arg Ala Ser Gln Ser Ile Ser Asn Asn
20 25 30

Leu His Trp Tyr Gln Gln Lys Ser His Glu Ser Pro Arg Leu Leu Ile
35 40 45

Lys Ser Ala Ser Gln Ser Ile Ser Gly Ile Pro Ser Arg Phe Ser Gly
50 55 60

Ser Gly Ser Gly Thr Asp Phe Thr Leu Ser Ile Asn Ser Val Glu Thr
65 70 75 80

Glu Asp Phe Gly Met Tyr Phe Cys Gln Gln Ser Asn Ser Trp Pro Tyr
85 90 95

Thr Phe Gly Gly Gly Thr Lys Leu Glu Ile Lys Arg Gly Ser Thr Ser
100 105 110

Gly Ser Gly Lys Pro Gly Ser Gly Glu Gly Ser Thr Lys Gly Gln Val
115 120 125

Gln Leu Gln Glu Ser Gly Ala Glu Leu Val Lys Pro Gly Ala Ser Val
130 135 140

Lys Leu Ser Cys Lys Ala Ser Gly Tyr Thr Phe Thr Ser Tyr Trp Met
145 150 155 160

His Trp Val Lys Gln Arg Pro Gly Gln Gly Leu Glu Trp Ile Gly Lys
165 170 175

Ile Asn Pro Ser Asn Gly Arg Thr Asn Tyr Asn Glu Lys Phe Lys Ser
180 185 190

Lys Ala Thr Leu Thr Val Asp Lys Ser Ser Ser Thr Ala Tyr Met Gln
195 200 205

Leu Ser Ser Leu Thr Ser Glu Asp Ser Ala Val Tyr Tyr Cys Ala Arg
210 215 220

Gly Gly Val Tyr Tyr Asp Leu Tyr Tyr Tyr Ala Leu Asp Tyr Trp Gly
225 230 235 240

Gln Gly Thr Thr Val Thr Val Ser Ser
245

<210> SEQ ID NO 10
<211> LENGTH: 108
<212> TYPE: PRT
<213> ORGANISM: Artificial Sequence
<220> FEATURE:
<223> OTHER INFORMATION: h189-1 VL

<400> SEQUENCE: 10

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Ile Ser Asn Asn
20 25 30

Leu His Trp Tyr Gln Gln Lys Pro Gly Gln Ala Pro Arg Leu Leu Ile
35 40 45

Tyr Ser Ala Ser Gln Ser Ile Ser Gly Ile Pro Ala Arg Phe Ser Gly
50 55 60

Ser Gly Pro Gly Thr Asp Phe Thr Leu Thr Ile Ser Ser Leu Glu Pro
65 70 75 80

Glu Asp Phe Ala Val Tyr Tyr Cys Gln Gln Ser Asn Ser Trp Pro Tyr

```
                85                  90                  95

Thr Phe Gly Gln Gly Thr Lys Val Glu Ile Lys Arg
            100                 105


<210> SEQ ID NO 11
<211> LENGTH: 123
<212> TYPE: PRT
<213> ORGANISM: Artificial Sequence
<220> FEATURE:
<223> OTHER INFORMATION: h189-1 VH

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Ser Asn Gly Arg Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Val Tyr Tyr Asp Leu Tyr Tyr Tyr Ala Leu Asp Tyr
            100                 105                 110

Trp Gly Gln Gly Thr Leu Val Thr Val Ser Ser
        115                 120


<210> SEQ ID NO 12
<211> LENGTH: 249
<212> TYPE: PRT
<213> ORGANISM: Artificial Sequence
<220> FEATURE:
<223> OTHER INFORMATION: h189-1 scFv

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Tyr Ser Ala Ser Gln Ser Ile Ser Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Ser Asn Ser Trp Pro Tyr
                85                  90                  95

Thr Phe Gly Gln Gly Thr Lys Val Glu Ile Lys Arg Gly Ser Thr Ser
            100                 105                 110

Gly Ser Gly Lys Pro Gly Ser Gly Glu Gly Ser Thr Lys Gly Gln Val
        115                 120                 125

Gln Leu Val Gln Ser Gly Ala Glu Val Lys Lys Pro Gly Ala Ser Val
    130                 135                 140

Lys Val Ser Cys Lys Ala Ser Gly Tyr Thr Phe Thr Ser Tyr Tyr Met
145                 150                 155                 160
```

```
His Trp Val Arg Gln Ala Pro Gly Gln Gly Leu Glu Trp Met Gly Trp
                165                 170                 175

Ile Asn Pro Ser Asn Gly Arg Thr Asn Tyr Ala Gln Lys Phe Gln Gly
            180                 185                 190

Arg Val Thr Met Thr Arg Asp Thr Ser Ile Ser Thr Ala Tyr Met Glu
        195                 200                 205

Leu Ser Arg Leu Arg Ser Asp Asp Thr Ala Val Tyr Tyr Cys Ala Arg
    210                 215                 220

Gly Gly Val Tyr Tyr Asp Leu Tyr Tyr Tyr Ala Leu Asp Tyr Trp Gly
225                 230                 235                 240

Gln Gly Thr Leu Val Thr Val Ser Ser
                245


<210> SEQ ID NO 13
<211> LENGTH: 108
<212> TYPE: PRT
<213> ORGANISM: Artificial Sequence
<220> FEATURE:
<223> OTHER INFORMATION: h189-2 VL

<400> SEQUENCE: 13

Asp Val Val Met Thr Gln Ser Pro Ala Phe Leu Ser Val Thr Pro Gly
1               5                   10                  15

Glu Lys Val Thr Ile Thr Cys Arg Ala Ser Gln Ser Ile Ser Asn Asn
            20                  25                  30

Leu His Trp Tyr Gln Gln Lys Pro Asp Gln Ala Pro Lys Leu Leu Ile
        35                  40                  45

Lys Ser Ala Ser Gln Ser Ile Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Ser Asn Ser Trp Pro Tyr
                85                  90                  95

Thr Phe Gly Gln Gly Thr Lys Val Glu Ile Lys Arg
            100                 105


<210> SEQ ID NO 14
<211> LENGTH: 123
<212> TYPE: PRT
<213> ORGANISM: Artificial Sequence
<220> FEATURE:
<223> OTHER INFORMATION: h189-2 VH

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Ser Asn Gly Arg Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Val Tyr Tyr Asp Leu Tyr Tyr Tyr Ala Leu Asp Tyr
            100                 105                 110
```

```
Trp Gly Gln Gly Thr Leu Val Thr Val Ser Ser
        115                 120


<210> SEQ ID NO 15
<211> LENGTH: 249
<212> TYPE: PRT
<213> ORGANISM: Artificial Sequence
<220> FEATURE:
<223> OTHER INFORMATION: h189-2 scFv

<400> SEQUENCE: 15

Asp Val Val Met Thr Gln Ser Pro Ala Phe Leu Ser Val Thr Pro Gly
1               5                   10                  15

Glu Lys Val Thr Ile Thr Cys Arg Ala Ser Gln Ser Ile Ser Asn Asn
            20                  25                  30

Leu His Trp Tyr Gln Gln Lys Pro Asp Gln Ala Pro Lys Leu Leu Ile
        35                  40                  45

Lys Ser Ala Ser Gln Ser Ile Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Ser Asn Ser Trp Pro Tyr
                85                  90                  95

Thr Phe Gly Gln Gly Thr Lys Val Glu Ile Lys Arg Gly Ser Thr Ser
            100                 105                 110

Gly Ser Gly Lys Pro Gly Ser Gly Glu Gly Ser Thr Lys Gly Gln Val
        115                 120                 125

Gln Leu Val Gln Ser Gly Ala Glu Val Lys Lys Pro Gly Ala Ser Val
    130                 135                 140

Lys Val Ser Cys Lys Ala Ser Gly Tyr Thr Phe Thr Ser Tyr Tyr Met
145                 150                 155                 160

His Trp Val Arg Gln Ala Pro Gly Gln Gly Leu Glu Trp Met Gly Trp
                165                 170                 175

Ile Asn Pro Ser Asn Gly Arg Thr Asn Tyr Ala Gln Lys Phe Gln Gly
            180                 185                 190

Arg Val Thr Met Thr Arg Asp Thr Ser Ile Ser Thr Ala Tyr Met Glu
        195                 200                 205

Leu Ser Arg Leu Arg Ser Asp Asp Thr Ala Val Tyr Tyr Cys Ala Arg
    210                 215                 220

Gly Gly Val Tyr Tyr Asp Leu Tyr Tyr Tyr Ala Leu Asp Tyr Trp Gly
225                 230                 235                 240

Gln Gly Thr Leu Val Thr Val Ser Ser
                245


<210> SEQ ID NO 16
<211> LENGTH: 108
<212> TYPE: PRT
<213> ORGANISM: Artificial Sequence
<220> FEATURE:
<223> OTHER INFORMATION: h189-3 VL

<400> SEQUENCE: 16

Asp Val Val Met Thr Gln Ser Pro Ala Phe Leu Ser Val Thr Pro Gly
1               5                   10                  15

Glu Lys Val Thr Ile Thr Cys Arg Ala Ser Gln Ser Ile Ser Asn Asn
            20                  25                  30

Leu His Trp Tyr Gln Gln Lys Pro Asp Gln Ala Pro Lys Leu Leu Ile
```

```
        35                  40                  45

Lys Ser Ala Ser Gln Ser Ile Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Met Tyr Phe Cys Gln Gln Ser Asn Ser Trp Pro Tyr
                85                  90                  95

Thr Phe Gly Gln Gly Thr Lys Val Glu Ile Lys Arg
            100                 105


<210> SEQ ID NO 17
<211> LENGTH: 123
<212> TYPE: PRT
<213> ORGANISM: Artificial Sequence
<220> FEATURE:
<223> OTHER INFORMATION: h189-3 VH

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Lys Ile Asn Pro Ser Asn Gly Arg Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Val Tyr Tyr Asp Leu Tyr Tyr Tyr Ala Leu Asp Tyr
            100                 105                 110

Trp Gly Gln Gly Thr Leu Val Thr Val Ser Ser
        115                 120


<210> SEQ ID NO 18
<211> LENGTH: 249
<212> TYPE: PRT
<213> ORGANISM: Artificial Sequence
<220> FEATURE:
<223> OTHER INFORMATION: h189-3 scFv

<400> SEQUENCE: 18

Asp Val Val Met Thr Gln Ser Pro Ala Phe Leu Ser Val Thr Pro Gly
1               5                   10                  15

Glu Lys Val Thr Ile Thr Cys Arg Ala Ser Gln Ser Ile Ser Asn Asn
            20                  25                  30

Leu His Trp Tyr Gln Gln Lys Pro Asp Gln Ala Pro Lys Leu Leu Ile
        35                  40                  45

Lys Ser Ala Ser Gln Ser Ile Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Met Tyr Phe Cys Gln Gln Ser Asn Ser Trp Pro Tyr
                85                  90                  95

Thr Phe Gly Gln Gly Thr Lys Val Glu Ile Lys Arg Gly Ser Thr Ser
            100                 105                 110
```

```
Gly Ser Gly Lys Pro Gly Ser Gly Glu Gly Ser Thr Lys Gly Gln Val
        115                 120                 125

Gln Leu Val Gln Ser Gly Ala Glu Val Lys Lys Pro Gly Ala Ser Val
    130                 135                 140

Lys Val Ser Cys Lys Ala Ser Gly Tyr Thr Phe Thr Ser Tyr Trp Met
145                 150                 155                 160

His Trp Val Arg Gln Ala Pro Gly Gln Gly Leu Glu Trp Met Gly Lys
                165                 170                 175

Ile Asn Pro Ser Asn Gly Arg Thr Asn Tyr Ala Gln Lys Phe Gln Gly
            180                 185                 190

Arg Val Thr Met Thr Arg Asp Thr Ser Ile Ser Thr Ala Tyr Met Glu
        195                 200                 205

Leu Ser Arg Leu Arg Ser Asp Asp Thr Ala Val Tyr Tyr Cys Ala Arg
    210                 215                 220

Gly Gly Val Tyr Tyr Asp Leu Tyr Tyr Tyr Ala Leu Asp Tyr Trp Gly
225                 230                 235                 240

Gln Gly Thr Leu Val Thr Val Ser Ser
                245


<210> SEQ ID NO 19
<211> LENGTH: 108
<212> TYPE: PRT
<213> ORGANISM: Artificial Sequence
<220> FEATURE:
<223> OTHER INFORMATION: h189-4 VL

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Ser Ala Ser Gln Ser Ile Ser Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Phe Cys Gln Gln Ser Asn Ser Trp Pro Tyr
                85                  90                  95

Thr Phe Gly Gln Gly Thr Lys Val Glu Ile Lys Arg
            100                 105


<210> SEQ ID NO 20
<211> LENGTH: 123
<212> TYPE: PRT
<213> ORGANISM: Artificial Sequence
<220> FEATURE:
<223> OTHER INFORMATION: h189-4 VH

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Lys Ile Asn Pro Ser Asn Gly Arg Thr Asn Tyr Ala Gln Lys Phe
    50                  55                  60
```

```
Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Val Tyr Tyr Asp Leu Tyr Tyr Tyr Ala Leu Asp Tyr
            100                 105                 110

Trp Gly Gln Gly Thr Leu Val Thr Val Ser Ser
        115                 120


<210> SEQ ID NO 21
<211> LENGTH: 249
<212> TYPE: PRT
<213> ORGANISM: Artificial Sequence
<220> FEATURE:
<223> OTHER INFORMATION: h189-4 scFv

<400> SEQUENCE: 21

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Ser Ala Ser Gln Ser Ile Ser Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Phe Cys Gln Gln Ser Asn Ser Trp Pro Tyr
                85                  90                  95

Thr Phe Gly Gln Gly Thr Lys Val Glu Ile Lys Arg Gly Ser Thr Ser
            100                 105                 110

Gly Ser Gly Lys Pro Gly Ser Gly Glu Gly Ser Thr Lys Gly Gln Val
        115                 120                 125

Gln Leu Val Gln Ser Gly Ala Glu Val Lys Lys Pro Gly Ala Ser Val
    130                 135                 140

Lys Val Ser Cys Lys Ala Ser Gly Tyr Thr Phe Thr Ser Tyr Trp Met
145                 150                 155                 160

His Trp Val Arg Gln Ala Pro Gly Gln Gly Leu Glu Trp Met Gly Lys
                165                 170                 175

Ile Asn Pro Ser Asn Gly Arg Thr Asn Tyr Ala Gln Lys Phe Gln Gly
            180                 185                 190

Arg Val Thr Met Thr Arg Asp Thr Ser Ile Ser Thr Ala Tyr Met Glu
        195                 200                 205

Leu Ser Arg Leu Arg Ser Asp Asp Thr Ala Val Tyr Tyr Cys Ala Arg
    210                 215                 220

Gly Gly Val Tyr Tyr Asp Leu Tyr Tyr Tyr Ala Leu Asp Tyr Trp Gly
225                 230                 235                 240

Gln Gly Thr Leu Val Thr Val Ser Ser
                245


<210> SEQ ID NO 22
<211> LENGTH: 25
<212> TYPE: PRT
<213> ORGANISM: Artificial Sequence
<220> FEATURE:
<223> OTHER INFORMATION: CD8alpha transmembrane domain
```

<400> SEQUENCE: 22

Ile Tyr Ile Trp Ala Pro Leu Ala Gly Thr Cys Gly Val Leu Leu Leu
1               5                   10                  15

Ser Leu Val Ile Thr Leu Tyr Cys Lys
            20                  25

<210> SEQ ID NO 23
<211> LENGTH: 75
<212> TYPE: DNA
<213> ORGANISM: Artificial Sequence
<220> FEATURE:
<223> OTHER INFORMATION: CD8alpha transmembrane domain

<400> SEQUENCE: 23
atctacatct gggcgccctt ggccgggact tgtggggtcc ttctcctgtc actggttatc 60
accctttact gcaaa 75

<210> SEQ ID NO 24
<211> LENGTH: 27
<212> TYPE: PRT
<213> ORGANISM: Artificial Sequence
<220> FEATURE:
<223> OTHER INFORMATION: CD28 transmembrane domain

<400> SEQUENCE: 24

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 25
<211> LENGTH: 81
<212> TYPE: DNA
<213> ORGANISM: Artificial Sequence
<220> FEATURE:
<223> OTHER INFORMATION: CD28 transmembrane domain

<400> SEQUENCE: 25
ttttgggtcc tcgtcgtagt tggaggggta cttgcctgtt atagcctcct ggttaccgta 60
gcatttatta tattctgggt g 81

<210> SEQ ID NO 26
<211> LENGTH: 41
<212> TYPE: PRT
<213> ORGANISM: Artificial Sequence
<220> FEATURE:
<223> OTHER INFORMATION: CD28 costimulatory domain

<400> SEQUENCE: 26

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 27
<211> LENGTH: 123
<212> TYPE: DNA
<213> ORGANISM: Artificial Sequence
<220> FEATURE:
<223> OTHER INFORMATION: CD28 costimulatory domain

<400> SEQUENCE: 27
aggagtaaga ggagcaggct cctgcacagt gactacatga acatgactcc ccgccgcccc 60
gggcccaccc gcaagcatta ccagccctat gccccaccac gcgacttcgc agcctatcgc 120
tcc 123

<210> SEQ ID NO 28
<211> LENGTH: 40
<212> TYPE: PRT
<213> ORGANISM: Artificial Sequence
<220> FEATURE:
<223> OTHER INFORMATION: 4-1BB costimulatory domain

<400> SEQUENCE: 28

Arg Gly Arg Lys Lys Leu Leu Tyr Ile Phe Lys Gln Pro Phe Met Arg
1 5 10 15

Pro Val Gln Thr Thr Gln Glu Glu Asp Gly Cys Ser Cys Arg Phe Pro
20 25 30

Glu Glu Glu Glu Gly Gly Cys Glu
35 40

<210> SEQ ID NO 29
<211> LENGTH: 120
<212> TYPE: DNA
<213> ORGANISM: Artificial Sequence
<220> FEATURE:
<223> OTHER INFORMATION: 4-1BB costimulatory domain

<400> SEQUENCE: 29
cggggcagaa agaaactcct gtatatattc aaacaaccat ttatgagacc agtacaaact 60
actcaagagg aagatggctg tagctgccga tttccagaag aagaagaagg aggatgtgaa 120

<210> SEQ ID NO 30
<211> LENGTH: 113
<212> TYPE: PRT
<213> ORGANISM: Artificial Sequence
<220> FEATURE:
<223> OTHER INFORMATION: CD3zeta signaling domain

<400> SEQUENCE: 30

Leu Arg Val Lys Phe Ser Arg Ser Ala Asp Ala Pro Ala Tyr Gln Gln
1 5 10 15

Gly Gln Asn Gln Leu Tyr Asn Glu Leu Asn Leu Gly Arg Arg Glu Glu
20 25 30

Tyr Asp Val Leu Asp Lys Arg Arg Gly Arg Asp Pro Glu Met Gly Gly
35 40 45

Lys Pro Arg Arg Lys Asn Pro Gln Glu Gly Leu Tyr Asn Glu Leu Gln
50 55 60

Lys Asp Lys Met Ala Glu Ala Tyr Ser Glu Ile Gly Met Lys Gly Glu
65 70 75 80

Arg Arg Arg Gly Lys Gly His Asp Gly Leu Tyr Gln Gly Leu Ser Thr
85 90 95

Ala Thr Lys Asp Thr Tyr Asp Ala Leu His Met Gln Ala Leu Pro Pro
100 105 110

Arg

<210> SEQ ID NO 31
<211> LENGTH: 339
<212> TYPE: DNA
<213> ORGANISM: Artificial Sequence
<220> FEATURE:
<223> OTHER INFORMATION: CD3zeta signaling domain

<400> SEQUENCE: 31
ctgagagtga agttcagcag gagcgcagac gcccccgcgt accagcaggg ccagaaccag 60
ctctataacg agctcaatct aggacgaaga gaggagtacg atgttttgga caagagacgt 120
ggccgggacc ctgagatggg gggaaagccg agaaggaaga accctcagga aggcctgtac 180
aatgaactgc agaaagataa gatggcggag gcctacagtg agattgggat gaaaggcgag 240
cgccggaggg gcaaggggca cgatggcctt taccagggtc tcagtacagc caccaaggac 300
acctacgacg cccttcacat gcaggccctg ccccctcgc 339

<210> SEQ ID NO 32
<211> LENGTH: 114
<212> TYPE: PRT
<213> ORGANISM: Artificial Sequence
<220> FEATURE:
<223> OTHER INFORMATION: CD3zeta signaling domain

<400> SEQUENCE: 32

Leu Arg Val Lys Phe Ser Arg Ser Ala Asp Ala Pro Ala Tyr Gln Gln
1               5                   10                  15

Gly Gln Asn Gln Leu Phe Asn Glu Leu Asn Leu Gly Arg Arg Glu Glu
            20                  25                  30

Phe Asp Val Leu Asp Lys Arg Arg Gly Arg Asp Pro Glu Met Gly Gly
        35                  40                  45

Lys Pro Gln Arg Arg Lys Asn Pro Gln Glu Gly Leu Tyr Asn Glu Leu
    50                  55                  60

Gln Lys Asp Lys Met Ala Glu Ala Tyr Ser Glu Ile Gly Met Lys Gly
65                  70                  75                  80

Glu Arg Arg Arg Gly Lys Gly His Asp Gly Leu Phe Gln Gly Leu Ser
                85                  90                  95

Thr Ala Thr Lys Asp Thr Phe Asp Ala Leu His Met Gln Ala Leu Pro
            100                 105                 110

Pro Arg

<210> SEQ ID NO 33
<211> LENGTH: 342
<212> TYPE: DNA
<213> ORGANISM: Artificial Sequence
<220> FEATURE:
<223> OTHER INFORMATION: CD3zeta signaling domain

<400> SEQUENCE: 33
ctgagagtga agttcagcag gagcgcagac gcccccgcgt accagcaggg ccagaaccag 60
ctctttaacg agctcaatct aggacgaaga gaggagttcg atgttttgga caagagacgt 120
ggccgggacc ctgagatggg gggaaagccg cagagaagga agaaccctca ggaaggcctg 180
tacaatgaac tgcagaaaga taagatggcg gaggcctaca gtgagattgg gatgaaaggc 240
gagcgccgga ggggcaaggg gcacgatggc cttttccagg gtctcagtac agccaccaag 300
gacacctttg acgcccttca catgcaggcc ctgccccctc gc 342

<210> SEQ ID NO 34
<211> LENGTH: 20
<212> TYPE: PRT
<213> ORGANISM: Artificial Sequence
<220> FEATURE:
<223> OTHER INFORMATION: B2M signal peptide

<400> SEQUENCE: 34

Met Ser Arg Ser Val Ala Leu Ala Val Leu Ala Leu Leu Ser Leu Ser
1 5 10 15

Gly Leu Glu Ala
20

<210> SEQ ID NO 35
<211> LENGTH: 60
<212> TYPE: DNA
<213> ORGANISM: Artificial Sequence
<220> FEATURE:
<223> OTHER INFORMATION: B2M signal peptide

<400> SEQUENCE: 35
atgtcccgct ctgttgcttt ggctgtgctg gccctttgt cccttagcgg actggaggcc 60

<210> SEQ ID NO 36
<211> LENGTH: 21
<212> TYPE: PRT
<213> ORGANISM: Artificial Sequence
<220> FEATURE:
<223> OTHER INFORMATION: CD8alpha signal peptide

<400> SEQUENCE: 36

Met Ala Leu Pro Val Thr Ala Leu Leu Leu Pro Leu Ala Leu Leu Leu
1 5 10 15

His Ala Ala Arg Pro
20

<210> SEQ ID NO 37
<211> LENGTH: 63
<212> TYPE: DNA
<213> ORGANISM: Artificial Sequence
<220> FEATURE:
<223> OTHER INFORMATION: CD8alpha signal peptide

<400> SEQUENCE: 37
atggccttac cagtgaccgc cttgctcctg ccgctggcct tgctgctcca cgccgccagg 60
ccg 63

<210> SEQ ID NO 38
<211> LENGTH: 45
<212> TYPE: PRT
<213> ORGANISM: Artificial Sequence
<220> FEATURE:
<223> OTHER INFORMATION: CD8alpha hinge region

<400> SEQUENCE: 38

Thr Thr Thr Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly
20 25 30

Gly Ala Val His Thr Arg Gly Leu Asp Phe Ala Cys Asp
35 40 45

<210> SEQ ID NO 39
<211> LENGTH: 135
<212> TYPE: DNA
<213> ORGANISM: Artificial Sequence
<220> FEATURE:
<223> OTHER INFORMATION: CD8alpha hinge region

<400> SEQUENCE: 39
accacgacgc cagcgccgcg accaccaaca ccggcgccca ccatcgcgtc gcagcccctg 60
tccctgcgcc cagaggcgtg ccggccagcg gcgggggggcg cagtgcacac gagggggctg 120
gacttcgcct gtgat 135

<210> SEQ ID NO 40
<211> LENGTH: 39
<212> TYPE: PRT
<213> ORGANISM: Artificial Sequence
<220> FEATURE:
<223> OTHER INFORMATION: CD28 hinge region

<400> SEQUENCE: 40

Ile Glu Val Met Tyr Pro Pro Pro Tyr Leu Asp Asn Glu Lys Ser Asn
1 5 10 15

Gly Thr Ile Ile His Val Lys Gly Lys His Leu Cys Pro Ser Pro Leu
20 25 30

Phe Pro Gly Pro Ser Lys Pro
35

<210> SEQ ID NO 41
<211> LENGTH: 117
<212> TYPE: DNA
<213> ORGANISM: Artificial Sequence
<220> FEATURE:
<223> OTHER INFORMATION: CD28 hinge region

<400> SEQUENCE: 41
attgaagtta tgtatcctcc tccttaccta gacaatgaga agagcaatgg aaccattatc 60
catgtgaaag ggaaacacct ttgtccaagt cccctatttc ccggaccttc taagccc 117

<210> SEQ ID NO 42
<211> LENGTH: 12
<212> TYPE: PRT
<213> ORGANISM: Artificial Sequence
<220> FEATURE:
<223> OTHER INFORMATION: IgG4 hinge region

<400> SEQUENCE: 42

Glu Ser Lys Tyr Gly Pro Pro Cys Pro Pro Cys Pro
1 5 10

<210> SEQ ID NO 43
<211> LENGTH: 36
<212> TYPE: DNA
<213> ORGANISM: Artificial Sequence
<220> FEATURE:
<223> OTHER INFORMATION: IgG4 hinge region

<400> SEQUENCE: 43
gaaagcaaat acgggccgcc gtgtccaccc tgtccg 36

<210> SEQ ID NO 44
<211> LENGTH: 18
<212> TYPE: PRT
<213> ORGANISM: Artificial Sequence
<220> FEATURE:
<223> OTHER INFORMATION: PD-L1 signal peptide

<400> SEQUENCE: 44

Met Arg Ile Phe Ala Val Phe Ile Phe Met Thr Tyr Trp His Leu Leu
1 5 10 15

Asn Ala

<210> SEQ ID NO 45
<211> LENGTH: 223
<212> TYPE: PRT
<213> ORGANISM: Artificial sequence
<220> FEATURE:
<223> OTHER INFORMATION: PDL1 extracellular domain

<400> SEQUENCE: 45

Phe Thr Val Thr Val Pro Lys Asp Leu Tyr Val Val Glu Tyr Gly Ser
1 5 10 15

Asn Met Thr Ile Glu Cys Lys Phe Pro Val Glu Lys Gln Leu Asp Leu
20 25 30

Ala Ala Leu Ile Val Tyr Trp Glu Met Glu Asp Lys Asn Ile Ile Gln
35 40 45

Phe Val His Gly Glu Glu Asp Leu Lys Val Gln His Ser Ser Tyr Arg
50 55 60

Gln Arg Ala Arg Leu Leu Lys Asp Gln Leu Ser Leu Gly Asn Ala Ala
65 70 75 80

Leu Gln Ile Thr Asp Val Lys Leu Gln Asp Ala Gly Val Tyr Arg Cys
85 90 95

Met Ile Ser Tyr Gly Gly Ala Asp Tyr Lys Arg Ile Thr Val Lys Val
100 105 110

Asn Ala Pro Tyr Asn Lys Ile Asn Gln Arg Ile Leu Val Val Asp Pro
115 120 125

Val Thr Ser Glu His Glu Leu Thr Cys Gln Ala Glu Gly Tyr Pro Lys
130 135 140

Ala Glu Val Ile Trp Thr Ser Ser Asp His Gln Val Leu Ser Gly Lys
145 150 155 160

Thr Thr Thr Thr Asn Ser Lys Arg Glu Glu Lys Leu Phe Asn Val Thr
165 170 175

Ser Thr Leu Arg Ile Asn Thr Thr Thr Asn Glu Ile Phe Tyr Cys Thr
180 185 190

Phe Arg Arg Leu Asp Pro Glu Glu Asn His Thr Ala Glu Leu Val Ile
195 200 205

Pro Glu Leu Pro Leu Ala His Pro Pro Asn Glu Arg Thr His Leu
210 215 220

<210> SEQ ID NO 46
<211> LENGTH: 201
<212> TYPE: PRT
<213> ORGANISM: Artificial sequence
<220> FEATURE:
<223> OTHER INFORMATION: PDL2 extracellular domain

<400> SEQUENCE: 46

Leu Phe Thr Val Thr Val Pro Lys Glu Leu Tyr Ile Ile Glu His Gly
1 5 10 15

Ser Asn Val Thr Leu Glu Cys Asn Phe Asp Thr Gly Ser His Val Asn
20 25 30

Leu Gly Ala Ile Thr Ala Ser Leu Gln Lys Val Glu Asn Asp Thr Ser
35 40 45

Pro His Arg Glu Arg Ala Thr Leu Leu Glu Glu Gln Leu Pro Leu Gly
50 55 60

Lys Ala Ser Phe His Ile Pro Gln Val Gln Val Arg Asp Glu Gly Gln
65 70 75 80

Tyr Gln Cys Ile Ile Ile Tyr Gly Val Ala Trp Asp Tyr Lys Tyr Leu

```
                85                  90                  95

Thr Leu Lys Val Lys Ala Ser Tyr Arg Lys Ile Asn Thr His Ile Leu
            100                 105                 110

Lys Val Pro Glu Thr Asp Glu Val Glu Leu Thr Cys Gln Ala Thr Gly
        115                 120                 125

Tyr Pro Leu Ala Glu Val Ser Trp Pro Asn Val Ser Val Pro Ala Asn
    130                 135                 140

Thr Ser His Ser Arg Thr Pro Glu Gly Leu Tyr Gln Val Thr Ser Val
145                 150                 155                 160

Leu Arg Leu Lys Pro Pro Pro Gly Arg Asn Phe Ser Cys Val Phe Trp
                165                 170                 175

Asn Thr His Val Arg Glu Leu Thr Leu Ala Ser Ile Asp Leu Gln Ser
            180                 185                 190

Gln Met Glu Pro Arg Thr His Pro Thr
        195                 200


<210> SEQ ID NO 47
<211> LENGTH: 356
<212> TYPE: PRT
<213> ORGANISM: Artificial sequence
<220> FEATURE:
<223> OTHER INFORMATION: E- cadherin EC1-EC2

<400> SEQUENCE: 47

Trp Leu Cys Gln Glu Pro Glu Pro Cys His Pro Gly Phe Asp Ala Glu
1               5                   10                  15

Ser Tyr Thr Phe Thr Val Pro Arg Arg His Leu Glu Arg Gly Arg Val
            20                  25                  30

Leu Gly Arg Val Asn Phe Glu Asp Cys Thr Gly Arg Gln Arg Thr Ala
        35                  40                  45

Tyr Phe Ser Leu Asp Thr Arg Phe Lys Val Gly Thr Asp Gly Val Ile
    50                  55                  60

Thr Val Lys Arg Pro Leu Arg Phe His Asn Pro Gln Ile His Phe Leu
65                  70                  75                  80

Val Tyr Ala Trp Asp Ser Thr Tyr Arg Lys Phe Ser Thr Lys Val Thr
                85                  90                  95

Leu Asn Thr Val Gly His His His Arg Pro Pro Pro His Gln Ala Ser
            100                 105                 110

Val Ser Gly Ile Gln Ala Glu Leu Leu Thr Phe Pro Asn Ser Ser Pro
        115                 120                 125

Gly Leu Arg Arg Gln Lys Arg Asp Trp Val Ile Pro Pro Ile Ser Cys
    130                 135                 140

Pro Glu Asn Glu Lys Gly Pro Phe Pro Lys Asn Leu Val Gln Ile Lys
145                 150                 155                 160

Ser Asn Lys Asp Lys Glu Gly Lys Val Phe Tyr Ser Ile Thr Gly Gln
                165                 170                 175

Gly Ala Asp Thr Pro Pro Val Gly Val Phe Ile Ile Glu Arg Glu Thr
            180                 185                 190

Gly Trp Leu Lys Val Thr Glu Pro Leu Asp Arg Glu Arg Ile Ala Thr
        195                 200                 205

Tyr Thr Leu Phe Ser His Ala Val Ser Ser Asn Gly Asn Ala Val Glu
    210                 215                 220

Asp Pro Met Glu Ile Leu Ile Thr Val Thr Asp Gln Asn Asp Asn Lys
225                 230                 235                 240

Pro Glu Phe Thr Gln Glu Val Phe Lys Gly Ser Val Met Glu Gly Ala
```

```
                245                 250                 255

Leu Pro Gly Thr Ser Val Met Glu Val Thr Ala Thr Asp Ala Asp Asp
            260                 265                 270

Asp Val Asn Thr Tyr Asn Ala Ala Ile Ala Tyr Thr Ile Leu Ser Gln
        275                 280                 285

Asp Pro Glu Leu Pro Asp Lys Asn Met Phe Thr Ile Asn Arg Asn Thr
    290                 295                 300

Gly Val Ile Ser Val Val Thr Thr Gly Leu Asp Arg Glu Ser Phe Pro
305                 310                 315                 320

Thr Tyr Thr Leu Val Val Gln Ala Ala Asp Leu Gln Gly Glu Gly Leu
                325                 330                 335

Ser Thr Thr Ala Thr Ala Val Ile Thr Val Thr Asp Thr Asn Asp Asn
            340                 345                 350

Pro Pro Ile Phe
        355


<210> SEQ ID NO 48
<211> LENGTH: 689
<212> TYPE: PRT
<213> ORGANISM: Artificial sequence
<220> FEATURE:
<223> OTHER INFORMATION: E- cadherin EC1-EC5

<400> SEQUENCE: 48

Trp Leu Cys Gln Glu Pro Glu Pro Cys His Pro Gly Phe Asp Ala Glu
1               5                   10                  15

Ser Tyr Thr Phe Thr Val Pro Arg Arg His Leu Glu Arg Gly Arg Val
            20                  25                  30

Leu Gly Arg Val Asn Phe Glu Asp Cys Thr Gly Arg Gln Arg Thr Ala
        35                  40                  45

Tyr Phe Ser Leu Asp Thr Arg Phe Lys Val Gly Thr Asp Gly Val Ile
    50                  55                  60

Thr Val Lys Arg Pro Leu Arg Phe His Asn Pro Gln Ile His Phe Leu
65                  70                  75                  80

Val Tyr Ala Trp Asp Ser Thr Tyr Arg Lys Phe Ser Thr Lys Val Thr
                85                  90                  95

Leu Asn Thr Val Gly His His His Arg Pro Pro Pro His Gln Ala Ser
            100                 105                 110

Val Ser Gly Ile Gln Ala Glu Leu Leu Thr Phe Pro Asn Ser Ser Pro
        115                 120                 125

Gly Leu Arg Arg Gln Lys Arg Asp Trp Val Ile Pro Pro Ile Ser Cys
    130                 135                 140

Pro Glu Asn Glu Lys Gly Pro Phe Pro Lys Asn Leu Val Gln Ile Lys
145                 150                 155                 160

Ser Asn Lys Asp Lys Glu Gly Lys Val Phe Tyr Ser Ile Thr Gly Gln
                165                 170                 175

Gly Ala Asp Thr Pro Pro Val Gly Val Phe Ile Ile Glu Arg Glu Thr
            180                 185                 190

Gly Trp Leu Lys Val Thr Glu Pro Leu Asp Arg Glu Arg Ile Ala Thr
        195                 200                 205

Tyr Thr Leu Phe Ser His Ala Val Ser Ser Asn Gly Asn Ala Val Glu
    210                 215                 220

Asp Pro Met Glu Ile Leu Ile Thr Val Thr Asp Gln Asn Asp Asn Lys
225                 230                 235                 240

Pro Glu Phe Thr Gln Glu Val Phe Lys Gly Ser Val Met Glu Gly Ala
```

-continued

```
                245                 250                 255

Leu Pro Gly Thr Ser Val Met Glu Val Thr Ala Thr Asp Ala Asp Asp
            260                 265                 270

Asp Val Asn Thr Tyr Asn Ala Ala Ile Ala Tyr Thr Ile Leu Ser Gln
        275                 280                 285

Asp Pro Glu Leu Pro Asp Lys Asn Met Phe Thr Ile Asn Arg Asn Thr
    290                 295                 300

Gly Val Ile Ser Val Val Thr Thr Gly Leu Asp Arg Glu Ser Phe Pro
305                 310                 315                 320

Thr Tyr Thr Leu Val Val Gln Ala Ala Asp Leu Gln Gly Glu Gly Leu
                325                 330                 335

Ser Thr Thr Ala Thr Ala Val Ile Thr Val Thr Asp Thr Asn Asp Asn
            340                 345                 350

Pro Pro Ile Phe Asn Pro Thr Thr Tyr Lys Gly Gln Val Pro Glu Asn
        355                 360                 365

Glu Ala Asn Val Val Ile Thr Thr Leu Lys Val Thr Asp Ala Asp Ala
    370                 375                 380

Pro Asn Thr Pro Ala Trp Glu Ala Val Tyr Thr Ile Leu Asn Asp Asp
385                 390                 395                 400

Gly Gly Gln Phe Val Val Thr Thr Asn Pro Val Asn Asn Asp Gly Ile
                405                 410                 415

Leu Lys Thr Ala Lys Gly Leu Asp Phe Glu Ala Lys Gln Gln Tyr Ile
            420                 425                 430

Leu His Val Ala Val Thr Asn Val Val Pro Phe Glu Val Ser Leu Thr
        435                 440                 445

Thr Ser Thr Ala Thr Val Thr Val Asp Val Leu Asp Val Asn Glu Ala
    450                 455                 460

Pro Ile Phe Val Pro Pro Glu Lys Arg Val Glu Val Ser Glu Asp Phe
465                 470                 475                 480

Gly Val Gly Gln Glu Ile Thr Ser Tyr Thr Ala Gln Glu Pro Asp Thr
                485                 490                 495

Phe Met Glu Gln Lys Ile Thr Tyr Arg Ile Trp Arg Asp Thr Ala Asn
            500                 505                 510

Trp Leu Glu Ile Asn Pro Asp Thr Gly Ala Ile Ser Thr Arg Ala Glu
        515                 520                 525

Leu Asp Arg Glu Asp Phe Glu His Val Lys Asn Ser Thr Tyr Thr Ala
    530                 535                 540

Leu Ile Ile Ala Thr Asp Asn Gly Ser Pro Val Ala Thr Gly Thr Gly
545                 550                 555                 560

Thr Leu Leu Leu Ile Leu Ser Asp Val Asn Asp Asn Ala Pro Ile Pro
                565                 570                 575

Glu Pro Arg Thr Ile Phe Phe Cys Glu Arg Asn Pro Lys Pro Gln Val
            580                 585                 590

Ile Asn Ile Ile Asp Ala Asp Leu Pro Pro Asn Thr Ser Pro Phe Thr
        595                 600                 605

Ala Glu Leu Thr His Gly Ala Ser Ala Asn Trp Thr Ile Gln Tyr Asn
    610                 615                 620

Asp Pro Thr Gln Glu Ser Ile Ile Leu Lys Pro Lys Met Ala Leu Glu
625                 630                 635                 640

Val Gly Asp Tyr Lys Ile Asn Leu Lys Leu Met Asp Asn Gln Asn Lys
                645                 650                 655

Asp Gln Val Thr Thr Leu Glu Val Ser Val Cys Asp Cys Glu Gly Ala
            660                 665                 670
```

Ala Gly Val Cys Arg Lys Ala Gln Pro Val Glu Ala Gly Leu Gln Ile
675 680 685

Pro

<210> SEQ ID NO 49
<211> LENGTH: 283
<212> TYPE: PRT
<213> ORGANISM: Artificial sequence
<220> FEATURE:
<223> OTHER INFORMATION: HLA-G extracellular domain

<400> SEQUENCE: 49

Gly Ser His Ser Met Arg Tyr Phe Ser Ala Ala Val Ser Arg Pro Gly
1 5 10 15

Arg Gly Glu Pro Arg Phe Ile Ala Met Gly Tyr Val Asp Asp Thr Gln
20 25 30

Phe Val Arg Phe Asp Ser Asp Ser Ala Cys Pro Arg Met Glu Pro Arg
35 40 45

Ala Pro Trp Val Glu Gln Glu Gly Pro Glu Tyr Trp Glu Glu Glu Thr
50 55 60

Arg Asn Thr Lys Ala His Ala Gln Thr Asp Arg Met Asn Leu Gln Thr
65 70 75 80

Leu Arg Gly Tyr Tyr Asn Gln Ser Glu Ala Ser Ser His Thr Leu Gln
85 90 95

Trp Met Ile Gly Cys Asp Leu Gly Ser Asp Gly Arg Leu Leu Arg Gly
100 105 110

Tyr Glu Gln Tyr Ala Tyr Asp Gly Lys Asp Tyr Leu Ala Leu Asn Glu
115 120 125

Asp Leu Arg Ser Trp Thr Ala Ala Asp Thr Ala Ala Gln Ile Ser Lys
130 135 140

Arg Lys Cys Glu Ala Ala Asn Val Ala Glu Gln Arg Arg Ala Tyr Leu
145 150 155 160

Glu Gly Thr Cys Val Glu Trp Leu His Arg Tyr Leu Glu Asn Gly Lys
165 170 175

Glu Met Leu Gln Arg Ala Asp Pro Pro Lys Thr His Val Thr His His
180 185 190

Pro Val Phe Asp Tyr Glu Ala Thr Leu Arg Cys Trp Ala Leu Gly Phe
195 200 205

Tyr Pro Ala Glu Ile Ile Leu Thr Trp Gln Arg Asp Gly Glu Asp Gln
210 215 220

Thr Gln Asp Val Glu Leu Val Glu Thr Arg Pro Ala Gly Asp Gly Thr
225 230 235 240

Phe Gln Lys Trp Ala Ala Val Val Val Pro Ser Gly Glu Glu Gln Arg
245 250 255

Tyr Thr Cys His Val Gln His Glu Gly Leu Pro Glu Pro Leu Met Leu
260 265 270

Arg Trp Lys Gln Ser Ser Leu Pro Thr Ile Pro
275 280

<210> SEQ ID NO 50
<211> LENGTH: 284
<212> TYPE: PRT
<213> ORGANISM: Artificial Sequence
<220> FEATURE:
<223> OTHER INFORMATION: HLA-E extracellular domain

<400> SEQUENCE: 50

Gly Ser His Ser Leu Lys Tyr Phe His Thr Ser Val Ser Arg Pro Gly
1 5 10 15

Arg Gly Glu Pro Arg Phe Ile Ser Val Gly Tyr Val Asp Asp Thr Gln
20 25 30

Phe Val Arg Phe Asp Asn Asp Ala Ala Ser Pro Arg Met Val Pro Arg
35 40 45

Ala Pro Trp Met Glu Gln Glu Gly Ser Glu Tyr Trp Asp Arg Glu Thr
50 55 60

Arg Ser Ala Arg Asp Thr Ala Gln Ile Phe Arg Val Asn Leu Arg Thr
65 70 75 80

Leu Arg Gly Tyr Tyr Asn Gln Ser Glu Ala Gly Ser His Thr Leu Gln
85 90 95

Trp Met His Gly Cys Glu Leu Gly Pro Asp Gly Arg Phe Leu Arg Gly
100 105 110

Tyr Glu Gln Phe Ala Tyr Asp Gly Lys Asp Tyr Leu Thr Leu Asn Glu
115 120 125

Asp Leu Arg Ser Trp Thr Ala Val Asp Thr Ala Ala Gln Ile Ser Glu
130 135 140

Gln Lys Ser Asn Asp Ala Ser Glu Ala Glu His Gln Arg Ala Tyr Leu
145 150 155 160

Glu Asp Thr Cys Val Glu Trp Leu His Lys Tyr Leu Glu Lys Gly Lys
165 170 175

Glu Thr Leu Leu His Leu Glu Pro Pro Lys Thr His Val Thr His His
180 185 190

Pro Ile Ser Asp His Glu Ala Thr Leu Arg Cys Trp Ala Leu Gly Phe
195 200 205

Tyr Pro Ala Glu Ile Thr Leu Thr Trp Gln Gln Asp Gly Glu Gly His
210 215 220

Thr Gln Asp Thr Glu Leu Val Glu Thr Arg Pro Ala Gly Asp Gly Thr
225 230 235 240

Phe Gln Lys Trp Ala Ala Val Val Val Pro Ser Gly Glu Glu Gln Arg
245 250 255

Tyr Thr Cys His Val Gln His Glu Gly Leu Pro Glu Pro Val Thr Leu
260 265 270

Arg Trp Lys Pro Ala Ser Gln Pro Thr Ile Pro Ile
275 280

<210> SEQ ID NO 51
<211> LENGTH: 284
<212> TYPE: PRT
<213> ORGANISM: Artificial Sequence
<220> FEATURE:
<223> OTHER INFORMATION: HLA-G extracellular domain mutant

<400> SEQUENCE: 51

Gly Ser His Ser Leu Lys Tyr Phe His Thr Ser Val Ser Arg Pro Gly
1 5 10 15

Arg Gly Glu Pro Arg Phe Ile Ser Val Gly Tyr Val Asp Asp Thr Gln
20 25 30

Phe Val Arg Phe Asp Asn Asp Ala Ala Ser Pro Arg Met Val Pro Arg
35 40 45

Ala Pro Trp Met Glu Gln Glu Gly Ser Glu Tyr Trp Asp Arg Glu Thr
50 55 60

Arg Ser Ala Arg Asp Thr Ala Gln Ile Phe Arg Val Asn Leu Arg Thr
65 70 75 80

-continued

Leu Arg Gly Cys Tyr Asn Gln Ser Glu Ala Gly Ser His Thr Leu Gln
85 90 95

Trp Met His Gly Cys Glu Leu Gly Pro Asp Gly Arg Phe Leu Arg Gly
100 105 110

Tyr Glu Gln Phe Ala Tyr Asp Gly Lys Asp Tyr Leu Thr Leu Asn Glu
115 120 125

Asp Leu Arg Ser Trp Thr Ala Val Asp Thr Ala Ala Gln Ile Ser Glu
130 135 140

Gln Lys Ser Asn Asp Ala Ser Glu Ala Glu His Gln Arg Ala Tyr Leu
145 150 155 160

Glu Asp Thr Cys Val Glu Trp Leu His Lys Tyr Leu Glu Lys Gly Lys
165 170 175

Glu Thr Leu Leu His Leu Glu Pro Pro Lys Thr His Val Thr His His
180 185 190

Pro Ile Ser Asp His Glu Ala Thr Leu Arg Cys Trp Ala Leu Gly Phe
195 200 205

Tyr Pro Ala Glu Ile Thr Leu Thr Trp Gln Gln Asp Gly Glu Gly His
210 215 220

Thr Gln Asp Thr Glu Leu Val Glu Thr Arg Pro Ala Gly Asp Gly Thr
225 230 235 240

Phe Gln Lys Trp Ala Ala Val Val Val Pro Ser Gly Glu Glu Gln Arg
245 250 255

Tyr Thr Cys His Val Gln His Glu Gly Leu Pro Glu Pro Val Thr Leu
260 265 270

Arg Trp Lys Pro Ala Ser Gln Pro Thr Ile Pro Ile
275 280

<210> SEQ ID NO 52
<211> LENGTH: 107
<212> TYPE: PRT
<213> ORGANISM: Artificial Sequence
<220> FEATURE:
<223> OTHER INFORMATION: CD19 scFv-1 VL

<400> SEQUENCE: 52

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Thr
100 105

<210> SEQ ID NO 53
<211> LENGTH: 120
<212> TYPE: PRT
<213> ORGANISM: Artificial Sequence
<220> FEATURE:
<223> OTHER INFORMATION: CD19 scFv-1 VH

<400> SEQUENCE: 53

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Cys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 54
<211> LENGTH: 242
<212> TYPE: PRT
<213> ORGANISM: Artificial Sequence
<220> FEATURE:
<223> OTHER INFORMATION: CD19 scFv-1

<400> SEQUENCE: 54

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val

```
225                 230                 235                 240

Ser Ser


<210> SEQ ID NO 55
<211> LENGTH: 107
<212> TYPE: PRT
<213> ORGANISM: Artificial Sequence
<220> FEATURE:
<223> OTHER INFORMATION: CD19 scFv-2 VL

<400> SEQUENCE: 55

Asp Ile Gln Met Thr Gln Ser Pro Ala Ser Leu Ser Thr Ser Leu Gly
1               5                   10                  15

Glu Thr Val Thr Ile Gln Cys Gln Ala Ser Glu Asp Ile Tyr Ser Gly
            20                  25                  30

Leu Ala Trp Tyr Gln Gln Lys Pro Gly Lys Ser Pro Gln Leu Leu Ile
        35                  40                  45

Tyr Gly Ala Ser Asp Leu Gln Asp Gly Val Pro Ser Arg Phe Ser Gly
    50                  55                  60

Ser Gly Ser Gly Thr Gln Tyr Ser Leu Lys Ile Thr Ser Met Gln Thr
65                  70                  75                  80

Glu Asp Glu Gly Val Tyr Phe Cys Gln Gln Gly Leu Thr Tyr Pro Arg
                85                  90                  95

Thr Phe Gly Gly Gly Thr Lys Leu Glu Leu Lys
            100                 105


<210> SEQ ID NO 56
<211> LENGTH: 116
<212> TYPE: PRT
<213> ORGANISM: Artificial Sequence
<220> FEATURE:
<223> OTHER INFORMATION: CD19 scFv-2 VH

<400> SEQUENCE: 56

Glu Val Gln Leu Gln Gln Ser Gly Ala Glu Leu Val Arg Pro Gly Thr
1               5                   10                  15

Ser Val Lys Leu Ser Cys Lys Val Ser Gly Asp Thr Ile Thr Phe Tyr
            20                  25                  30

Tyr Met His Phe Val Lys Gln Arg Pro Gly Gln Gly Leu Glu Trp Ile
        35                  40                  45

Gly Arg Ile Asp Pro Glu Asp Glu Ser Thr Lys Tyr Ser Glu Lys Phe
    50                  55                  60

Lys Asn Lys Ala Thr Leu Thr Ala Asp Thr Ser Ser Asn Thr Ala Tyr
65                  70                  75                  80

Leu Lys Leu Ser Ser Leu Thr Ser Glu Asp Thr Ala Thr Tyr Phe Cys
                85                  90                  95

Ile Tyr Gly Gly Tyr Tyr Phe Asp Tyr Trp Gly Gln Gly Val Met Val
            100                 105                 110

Thr Val Ser Ser
        115


<210> SEQ ID NO 57
<211> LENGTH: 238
<212> TYPE: PRT
<213> ORGANISM: Artificial Sequence
<220> FEATURE:
<223> OTHER INFORMATION: CD19 scFv-2

<400> SEQUENCE: 57
```

```
Asp Ile Gln Met Thr Gln Ser Pro Ala Ser Leu Ser Thr Ser Leu Gly
1               5                   10                  15

Glu Thr Val Thr Ile Gln Cys Gln Ala Ser Glu Asp Ile Tyr Ser Gly
            20                  25                  30

Leu Ala Trp Tyr Gln Gln Lys Pro Gly Lys Ser Pro Gln Leu Leu Ile
        35                  40                  45

Tyr Gly Ala Ser Asp Leu Gln Asp Gly Val Pro Ser Arg Phe Ser Gly
    50                  55                  60

Ser Gly Ser Gly Thr Gln Tyr Ser Leu Lys Ile Thr Ser Met Gln Thr
65                  70                  75                  80

Glu Asp Glu Gly Val Tyr Phe Cys Gln Gln Gly Leu Thr Tyr Pro Arg
                85                  90                  95

Thr Phe Gly Gly Gly Thr Lys Leu Glu Leu Lys Gly Gly Gly Gly Ser
            100                 105                 110

Gly Gly Gly Gly Ser Gly Gly Gly Gly Ser Glu Val Gln Leu Gln Gln
        115                 120                 125

Ser Gly Ala Glu Leu Val Arg Pro Gly Thr Ser Val Lys Leu Ser Cys
    130                 135                 140

Lys Val Ser Gly Asp Thr Ile Thr Phe Tyr Tyr Met His Phe Val Lys
145                 150                 155                 160

Gln Arg Pro Gly Gln Gly Leu Glu Trp Ile Gly Arg Ile Asp Pro Glu
                165                 170                 175

Asp Glu Ser Thr Lys Tyr Ser Glu Lys Phe Lys Asn Lys Ala Thr Leu
            180                 185                 190

Thr Ala Asp Thr Ser Ser Asn Thr Ala Tyr Leu Lys Leu Ser Ser Leu
        195                 200                 205

Thr Ser Glu Asp Thr Ala Thr Tyr Phe Cys Ile Tyr Gly Gly Tyr Tyr
    210                 215                 220

Phe Asp Tyr Trp Gly Gln Gly Val Met Val Thr Val Ser Ser
225                 230                 235


<210> SEQ ID NO 58
<211> LENGTH: 119
<212> TYPE: PRT
<213> ORGANISM: Artificial sequence
<220> FEATURE:
<223> OTHER INFORMATION: mNKG2A scFv-VH

<400> SEQUENCE: 58

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ser Pro Glu Lys Arg Leu Glu Trp Val
        35                  40                  45

Ala Glu Ile Ser Ser Gly Gly Ser Tyr Thr Tyr Tyr Pro Asp Thr Val
    50                  55                  60

Thr Gly Arg Phe Thr Ile Ser Arg Asp Asn Ala Lys Asn Thr Leu Tyr
65                  70                  75                  80

Leu Glu Ile Ser Ser Leu Arg Ser Glu Asp Thr Ala Met Tyr Tyr Cys
                85                  90                  95

Thr Arg His Gly Asp Tyr Pro Arg Phe Phe Asp Val Trp Gly Ala Gly
            100                 105                 110

Thr Thr Val Thr Val Ser Ser
        115
```

<210> SEQ ID NO 59
<211> LENGTH: 107
<212> TYPE: PRT
<213> ORGANISM: Artificial sequence
<220> FEATURE:
<223> OTHER INFORMATION: mNKG2A scFv-VL

<400> SEQUENCE: 59

```
Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Ile
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Gly Asn Pro Tyr Thr
                85                  90                  95

Phe Gly Gly Gly Thr Lys Leu Glu Ile Lys Arg
            100                 105
```

<210> SEQ ID NO 60
<211> LENGTH: 244
<212> TYPE: PRT
<213> ORGANISM: Artificial sequence
<220> FEATURE:
<223> OTHER INFORMATION: mNKG2A scFv

<400> SEQUENCE: 60

```
Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Ile
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Gly Asn Pro Tyr Thr
                85                  90                  95

Phe Gly Gly Gly Thr Lys Leu Glu Ile Lys Arg Gly Ser Thr Ser Gly
            100                 105                 110

Ser Gly Lys Pro Gly Ser Gly Glu Gly Ser Thr Lys Gly Glu Val Gln
        115                 120                 125

Leu Val Glu Ser Gly Gly Gly Leu Val Lys Pro Gly Gly Ser Leu Lys
    130                 135                 140

Leu Ser Cys Ala Ala Ser Gly Phe Thr Phe Ser Ser Tyr Ala Met Ser
145                 150                 155                 160

Trp Val Arg Gln Ser Pro Glu Lys Arg Leu Glu Trp Val Ala Glu Ile
                165                 170                 175

Ser Ser Gly Gly Ser Tyr Thr Tyr Tyr Pro Asp Thr Val Thr Gly Arg
            180                 185                 190

Phe Thr Ile Ser Arg Asp Asn Ala Lys Asn Thr Leu Tyr Leu Glu Ile
        195                 200                 205
```

Ser Ser Leu Arg Ser Glu Asp Thr Ala Met Tyr Tyr Cys Thr Arg His
210 215 220

Gly Asp Tyr Pro Arg Phe Phe Asp Val Trp Gly Ala Gly Thr Thr Val
225 230 235 240

Thr Val Ser Ser

<210> SEQ ID NO 61
<211> LENGTH: 119
<212> TYPE: PRT
<213> ORGANISM: Artificial sequence
<220> FEATURE:
<223> OTHER INFORMATION: hNKG2A scFv-VH

<400> SEQUENCE: 61

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ala Lys Ser Trp Val Arg Gln Ala Pro Gly Lys Gly Leu Glu Trp Val
35 40 45

Ser Glu Ile Ser Ser Gly Gly Ser Tyr Thr Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg His Gly Asp Tyr Pro Arg Phe Phe Asp Val Trp Gly Gln Gly
100 105 110

Thr Thr Val Thr Val Ser Ser
115

<210> SEQ ID NO 62
<211> LENGTH: 107
<212> TYPE: PRT
<213> ORGANISM: Artificial sequence
<220> FEATURE:
<223> OTHER INFORMATION: hNKG2A scFv-VL

<400> SEQUENCE: 62

Glu Ile Val Leu Thr Gln Ser Pro Ala Thr Leu Ser Leu Ser Pro Gly
1 5 10 15

Glu Arg Ala Thr Leu Ser Cys Ser Ala Ser Ser Ser Val Ser Ser Tyr
20 25 30

Ile Tyr Trp Tyr Gln Gln Lys Pro Gly Gln Ala Pro Arg Leu Leu Ile
35 40 45

Tyr Leu Thr Ser Asn Leu Ala Ser Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Trp Ser Gly Asn Pro Tyr
85 90 95

Thr Phe Gly Gln Gly Thr Lys Leu Glu Ile Lys
100 105

<210> SEQ ID NO 63
<211> LENGTH: 244
<212> TYPE: PRT
<213> ORGANISM: Artificial sequence
<220> FEATURE:
<223> OTHER INFORMATION: hNKG2A scFv

<400> SEQUENCE: 63

Glu Ile Val Leu Thr Gln Ser Pro Ala Thr Leu Ser Leu Ser Pro Gly
1 5 10 15

Glu Arg Ala Thr Leu Ser Cys Ser Ala Ser Ser Ser Val Ser Ser Tyr
20 25 30

Ile Tyr Trp Tyr Gln Gln Lys Pro Gly Gln Ala Pro Arg Leu Leu Ile
35 40 45

Tyr Leu Thr Ser Asn Leu Ala Ser Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Trp Ser Gly Asn Pro Tyr
85 90 95

Thr Phe Gly Gln Gly Thr Lys Leu Glu Ile Lys Gly Ser Thr Ser Gly
100 105 110

Ser Gly Lys Pro Gly Ser Gly Glu Gly Ser Thr Lys Gly Glu Val Gln
115 120 125

Leu Val Glu Ser Gly Gly Gly Leu Val Lys Pro Gly Gly Ser Leu Arg
130 135 140

Leu Ser Cys Ala Ala Ser Gly Phe Thr Phe Ser Ser Tyr Ala Lys Ser
145 150 155 160

Trp Val Arg Gln Ala Pro Gly Lys Gly Leu Glu Trp Val Ser Glu Ile
165 170 175

Ser Ser Gly Gly Ser Tyr Thr Tyr Tyr Ala Asp Ser Val Lys Gly Arg
180 185 190

Phe Thr Ile Ser Arg Asp Asn Ala Lys Asn Ser Leu Tyr Leu Gln Met
195 200 205

Asn Ser Leu Arg Ala Glu Asp Thr Ala Val Tyr Tyr Cys Ala Arg His
210 215 220

Gly Asp Tyr Pro Arg Phe Phe Asp Val Trp Gly Gln Gly Thr Thr Val
225 230 235 240

Thr Val Ser Ser

<210> SEQ ID NO 64
<211> LENGTH: 15
<212> TYPE: PRT
<213> ORGANISM: Artificial sequence
<220> FEATURE:
<223> OTHER INFORMATION: linker

<400> SEQUENCE: 64

Gly Gly Gly Gly Ser Gly Gly Gly Gly Ser Gly Gly Gly Gly Ser
1 5 10 15

<210> SEQ ID NO 65
<211> LENGTH: 108
<212> TYPE: PRT
<213> ORGANISM: Artificial sequence
<220> FEATURE:
<223> OTHER INFORMATION: KIR scFv VL

<400> SEQUENCE: 65

Glu Ile Val Leu Thr Gln Ser Pro Val Thr Leu Ser Leu Ser Pro Gly
1 5 10 15

Glu Arg Ala Thr Leu Ser Cys Arg Ala Ser Gln Ser Val Ser Ser Tyr

```
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Met Tyr
                85                  90                  95

Thr Phe Gly Gln Gly Thr Lys Leu Glu Ile Lys Arg
            100                 105


<210> SEQ ID NO 66
<211> LENGTH: 123
<212> TYPE: PRT
<213> ORGANISM: Artificial sequence
<220> FEATURE:
<223> OTHER INFORMATION: KIR scFv VH

<400> SEQUENCE: 66

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Phe Tyr
            20                  25                  30

Ala Ile Ser Trp Val Arg Gln Ala Pro Gly Gln Gly Leu Glu Trp Met
        35                  40                  45

Gly Gly Phe Ile Pro Ile Phe Gly Ala Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Ile Pro Ser Gly Ser Tyr Tyr Tyr Asp Tyr Asp Met Asp Val
            100                 105                 110

Trp Gly Gln Gly Thr Thr Val Thr Val Ser Ser
        115                 120


<210> SEQ ID NO 67
<211> LENGTH: 246
<212> TYPE: PRT
<213> ORGANISM: Artificial sequence
<220> FEATURE:
<223> OTHER INFORMATION: KIR scFv

<400> SEQUENCE: 67

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Phe Tyr
            20                  25                  30

Ala Ile Ser Trp Val Arg Gln Ala Pro Gly Gln Gly Leu Glu Trp Met
        35                  40                  45

Gly Gly Phe Ile Pro Ile Phe Gly Ala Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Tyr Cys
                85                  90                  95
```

Ala Arg Ile Pro Ser Gly Ser Tyr Tyr Tyr Asp Tyr Asp Met Asp Val
100 105 110

Trp Gly Gln Gly Thr Thr Val Thr Val Ser Ser Gly Gly Gly Gly Ser
115 120 125

Gly Gly Gly Gly Ser Gly Gly Gly Gly Ser Glu Ile Val Leu Thr Gln
130 135 140

Ser Pro Val Thr Leu Ser Leu Ser Pro Gly Glu Arg Ala Thr Leu Ser
145 150 155 160

Cys Arg Ala Ser Gln Ser Val Ser Ser Tyr Leu Ala Trp Tyr Gln Gln
165 170 175

Lys Pro Gly Gln Ala Pro Arg Leu Leu Ile Tyr Asp Ala Ser Asn Arg
180 185 190

Ala Thr Gly Ile Pro Ala Arg Phe Ser Gly Ser Gly Ser Gly Thr Asp
195 200 205

Phe Thr Leu Thr Ile Ser Ser Leu Glu Pro Glu Asp Phe Ala Val Tyr
210 215 220

Tyr Cys Gln Gln Arg Ser Asn Trp Met Tyr Thr Phe Gly Gln Gly Thr
225 230 235 240

Lys Leu Glu Ile Lys Arg
245

<210> SEQ ID NO 68
<211> LENGTH: 107
<212> TYPE: PRT
<213> ORGANISM: Artificial sequence
<220> FEATURE:
<223> OTHER INFORMATION: LIR1 scFv-1 VL

<400> SEQUENCE: 68

Asp Ile Leu Leu Thr Gln Ser Pro Ala Ile Leu Ser Val Ser Pro Gly
1 5 10 15

Glu Arg Val Ser Phe Ser Cys Arg Ala Ser Gln Ser Ile Gly Thr Asn
20 25 30

Ile His Trp Tyr Gln Gln Arg Thr Asn Gly Ser Pro Arg Leu Leu Ile
35 40 45

Lys Tyr Ala Ser Glu Ser Ile Ser Gly Ile Pro Ser Arg Phe Ser Gly
50 55 60

Ser Gly Ser Gly Thr Asp Phe Thr Leu Thr Ile Asn Ser Val Glu Ser
65 70 75 80

Glu Asp Ile Ala Asp Tyr Tyr Cys Gln Gln Ser Tyr Ser Trp Pro Tyr
85 90 95

Thr Phe Gly Gly Gly Thr Lys Leu Glu Ile Lys
100 105

<210> SEQ ID NO 69
<211> LENGTH: 118
<212> TYPE: PRT
<213> ORGANISM: Artificial sequence
<220> FEATURE:
<223> OTHER INFORMATION: LIR1 scFv-1 VH

<400> SEQUENCE: 69

Gln Val Thr Leu Lys Glu Ser Gly Pro Gly Ile Leu Lys Pro Ser Gln
1 5 10 15

Thr Leu Ser Leu Thr Cys Ser Phe Ser Gly Phe Ser Leu Ser Thr Ser
20 25 30

Gly Leu Gly Val Gly Trp Ile Arg Gln Pro Ser Gly Lys Gly Leu Glu
35 40 45

```
Trp Leu Ala His Ile Trp Trp Asp Asp Asp Lys Tyr Tyr Leu Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Thr Glu Leu Gly Arg Gly Asp Tyr Trp Gly Gln Gly Thr
            100                 105                 110

Ser Val Ala Val Ser Ser
        115
```

<210> SEQ ID NO 70
<211> LENGTH: 243
<212> TYPE: PRT
<213> ORGANISM: Artificial sequence
<220> FEATURE:
<223> OTHER INFORMATION: LIR1 scFv-2

<400> SEQUENCE: 70

```
Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Asn Ser Val Glu Ser
65                  70                  75                  80

Glu Asp Ile Ala Asp Tyr Tyr Cys Gln Gln Ser Tyr Ser Trp Pro Tyr
                85                  90                  95

Thr Phe Gly Gly Gly Thr Lys Leu Glu Ile Lys Gly Ser Thr Ser Gly
            100                 105                 110

Ser Gly Lys Pro Gly Ser Gly Glu Gly Ser Thr Lys Gly Gln Val Thr
        115                 120                 125

Leu Lys Glu Ser Gly Pro Gly Ile Leu Lys Pro Ser Gln Thr Leu Ser
    130                 135                 140

Leu Thr Cys Ser Phe Ser Gly Phe Ser Leu Ser Thr Ser Gly Leu Gly
145                 150                 155                 160

Val Gly Trp Ile Arg Gln Pro Ser Gly Lys Gly Leu Glu Trp Leu Ala
                165                 170                 175

His Ile Trp Trp Asp Asp Asp Lys Tyr Tyr Leu Pro Ser Leu Lys Ser
            180                 185                 190

Gln Leu Thr Ile Ser Lys Asp Thr Ser Arg Asn Gln Val Phe Leu Lys
        195                 200                 205

Ile Thr Ser Val Asp Thr Ala Asp Thr Ala Thr Tyr Tyr Cys Ala Arg
    210                 215                 220

Thr Glu Leu Gly Arg Gly Asp Tyr Trp Gly Gln Gly Thr Ser Val Ala
225                 230                 235                 240

Val Ser Ser
```

<210> SEQ ID NO 71
<211> LENGTH: 121
<212> TYPE: PRT
<213> ORGANISM: Artificial sequence
<220> FEATURE:

<223> OTHER INFORMATION: LIR1 scFv-2 VL

<400> SEQUENCE: 71

Glu Val Gln Leu Gln Gln Ser Gly Thr Val Leu Pro Arg Pro Gly Ala
1               5                   10                  15

Ser Val Lys Met Ser Cys Lys Ala Ser Gly Tyr Ser Phe Thr Asn Tyr
            20                  25                  30

Trp Met His Trp Val Lys Gln Arg Pro Gly Gln Gly Leu Glu Trp Ile
        35                  40                  45

Gly Ala Ile Tyr Pro Gly Asn Ser Asp Thr Ser Tyr Asn Gln Lys Phe
    50                  55                  60

Glu Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Thr Tyr Asp Gly Tyr Tyr Ser Ala Trp Phe Ala Tyr Trp Gly Gln
            100                 105                 110

Gly Thr Leu Val Thr Val Ser Ala Ala
        115                 120

<210> SEQ ID NO 72
<211> LENGTH: 108
<212> TYPE: PRT
<213> ORGANISM: Artificial sequence
<220> FEATURE:
<223> OTHER INFORMATION: LIR1 scFv-2 VH

<400> SEQUENCE: 72

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Leu Tyr Tyr Cys Gln Gln His Tyr Ser Pro Pro Trp
                85                  90                  95

Thr Phe Gly Gly Gly Thr Lys Leu Glu Ile Lys Arg
            100                 105

<210> SEQ ID NO 73
<211> LENGTH: 244
<212> TYPE: PRT
<213> ORGANISM: Artificial sequence
<220> FEATURE:
<223> OTHER INFORMATION: LIR1 scFv-2

<400> SEQUENCE: 73

Glu Val Gln Leu Gln Gln Ser Gly Thr Val Leu Pro Arg Pro Gly Ala
1               5                   10                  15

Ser Val Lys Met Ser Cys Lys Ala Ser Gly Tyr Ser Phe Thr Asn Tyr
            20                  25                  30

Trp Met His Trp Val Lys Gln Arg Pro Gly Gln Gly Leu Glu Trp Ile
        35                  40                  45

Gly Ala Ile Tyr Pro Gly Asn Ser Asp Thr Ser Tyr Asn Gln Lys Phe

```
    50                  55                  60

Glu Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Thr Tyr Asp Gly Tyr Tyr Ser Ala Trp Phe Ala Tyr Trp Gly Gln
            100                 105                 110

Gly Thr Leu Val Thr Val Ser Ala Ala Gly Gly Gly Gly Ser Gly Gly
        115                 120                 125

Gly Gly Ser Gly Gly Gly Gly Ser Asp Ile Val Met Thr Gln Ser His
    130                 135                 140

Lys Phe Met Ser Thr Ser Val Gly Asp Arg Val Ser Ile Thr Cys Lys
145                 150                 155                 160

Ala Ser Gln Asp Val Ser Thr Ala Val Ala Trp Tyr Gln Gln Lys Pro
                165                 170                 175

Gly Gln Ser Pro Lys Leu Leu Ile Tyr Ser Ala Ser Tyr Arg Tyr Thr
            180                 185                 190

Gly Val Pro Asp Arg Phe Thr Gly Ser Gly Ser Gly Thr Asp Phe Thr
        195                 200                 205

Phe Thr Ile Ser Ser Val Gln Ala Glu Asp Leu Ala Leu Tyr Tyr Cys
    210                 215                 220

Gln Gln His Tyr Ser Pro Pro Trp Thr Phe Gly Gly Gly Thr Lys Leu
225                 230                 235                 240

Glu Ile Lys Arg


<210> SEQ ID NO 74
<211> LENGTH: 99
<212> TYPE: PRT
<213> ORGANISM: Artificial sequence
<220> FEATURE:
<223> OTHER INFORMATION: B2M

<400> SEQUENCE: 74

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met


<210> SEQ ID NO 75
<211> LENGTH: 9
<212> TYPE: PRT
<213> ORGANISM: Artificial sequence
<220> FEATURE:
<223> OTHER INFORMATION: presenting peptide

<400> SEQUENCE: 75

Val Met Ala Pro Arg Thr Leu Ile Leu
1               5
```

<210> SEQ ID NO 76
<211> LENGTH: 124
<212> TYPE: PRT
<213> ORGANISM: Artificial sequence
<220> FEATURE:
<223> OTHER INFORMATION: NKG2A scFv VH

<400> SEQUENCE: 76

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Met Asn Trp Val Arg Gln Ala Pro Gly Gln Gly Leu Glu Trp Met
35 40 45

Gly Arg Ile Asp Pro Tyr Asp Ser Glu Thr His Tyr Ala Gln Lys Leu
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Gly Gly Tyr Asp Phe Asp Val Gly Thr Leu Tyr Trp Phe Phe
100 105 110

Asp Val Trp Gly Gln Gly Thr Thr Val Thr Val Ser
115 120

<210> SEQ ID NO 77
<211> LENGTH: 107
<212> TYPE: PRT
<213> ORGANISM: Artificial sequence
<220> FEATURE:
<223> OTHER INFORMATION: NKG2A scFv VL

<400> SEQUENCE: 77

Asp Ile Gln Met Thr Gln Ser Pro Ser Ser Leu Ser Ala Ser Val Gly
1 5 10 15

Asp Arg Val Thr Ile Thr Cys Arg Ala Ser Glu Asn Ile Tyr Ser Tyr
20 25 30

Leu Ala Trp Tyr Gln Gln Lys Pro Gly Lys Ala Pro Lys Leu Leu Ile
35 40 45

Tyr Asn Ala Lys Thr Leu Ala Glu Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln His His Tyr Gly Thr Pro Arg
85 90 95

Thr Phe Gly Gly Gly Thr Lys Val Glu Ile Lys
100 105

<210> SEQ ID NO 78
<211> LENGTH: 246
<212> TYPE: PRT
<213> ORGANISM: Artificial sequence
<220> FEATURE:
<223> OTHER INFORMATION: NKG2A scFv

<400> SEQUENCE: 78

Asp Ile Gln Met Thr Gln Ser Pro Ser Ser Leu Ser Ala Ser Val Gly
1 5 10 15

Asp Arg Val Thr Ile Thr Cys Arg Ala Ser Glu Asn Ile Tyr Ser Tyr
20 25 30

Leu Ala Trp Tyr Gln Gln Lys Pro Gly Lys Ala Pro Lys Leu Leu Ile
35 40 45

Tyr Asn Ala Lys Thr Leu Ala Glu Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln His His Tyr Gly Thr Pro Arg
85 90 95

Thr Phe Gly Gly Gly Thr Lys Val Glu Ile Lys Gly Gly Gly Gly Ser
100 105 110

Gly Gly Gly Gly Ser Gly Gly Gly Gly Ser Gln Val Gln Leu Val Gln
115 120 125

Ser Gly Ala Glu Val Lys Lys Pro Gly Ala Ser Val Lys Val Ser Cys
130 135 140

Lys Ala Ser Gly Tyr Thr Phe Thr Ser Tyr Trp Met Asn Trp Val Arg
145 150 155 160

Gln Ala Pro Gly Gln Gly Leu Glu Trp Met Gly Arg Ile Asp Pro Tyr
165 170 175

Asp Ser Glu Thr His Tyr Ala Gln Lys Leu Gln Gly Arg Val Thr Met
180 185 190

Thr Thr Asp Thr Ser Thr Ser Thr Ala Tyr Met Glu Leu Arg Ser Leu
195 200 205

Arg Ser Asp Asp Thr Ala Val Tyr Tyr Cys Ala Arg Gly Gly Tyr Asp
210 215 220

Phe Asp Val Gly Thr Leu Tyr Trp Phe Phe Asp Val Trp Gly Gln Gly
225 230 235 240

Thr Thr Val Thr Val Ser
245

<210> SEQ ID NO 79
<211> LENGTH: 109
<212> TYPE: PRT
<213> ORGANISM: Artificial sequence
<220> FEATURE:
<223> OTHER INFORMATION: KIR scFv VL

<400> SEQUENCE: 79

Glu Ile Val Leu Thr Gln Ser Pro Val Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Met Tyr
85 90 95

Thr Phe Gly Gln Gly Thr Lys Leu Glu Ile Lys Arg Thr
100 105

<210> SEQ ID NO 80
<211> LENGTH: 123

<212> TYPE: PRT
<213> ORGANISM: Artificial sequence
<220> FEATURE:
<223> OTHER INFORMATION: KIR scFv VH

<400> SEQUENCE: 80

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Phe Tyr
20 25 30

Ala Ile Ser Trp Val Arg Gln Ala Pro Gly Gln Gly Leu Glu Trp Met
35 40 45

Gly Gly Phe Ile Pro Ile Phe Gly Ala Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Asp Asp Thr Ala Val Tyr Tyr Cys
85 90 95

Ala Arg Ile Pro Ser Gly Ser Tyr Tyr Tyr Asp Tyr Asp Met Asp Val
100 105 110

Trp Gly Gln Gly Thr Thr Val Thr Val Ser Ser
115 120

<210> SEQ ID NO 81
<211> LENGTH: 247
<212> TYPE: PRT
<213> ORGANISM: Artificial sequence
<220> FEATURE:
<223> OTHER INFORMATION: KIR scFv

<400> SEQUENCE: 81

Glu Ile Val Leu Thr Gln Ser Pro Val Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Met Tyr
85 90 95

Thr Phe Gly Gln Gly Thr Lys Leu Glu Ile Lys Arg Thr Gly Gly Gly
100 105 110

Gly Ser Gly Gly Gly Gly Ser Gly Gly Gly Gly Ser Gln Val Gln Leu
115 120 125

Val Gln Ser Gly Ala Glu Val Lys Lys Pro Gly Ser Ser Val Lys Val
130 135 140

Ser Cys Lys Ala Ser Gly Gly Thr Phe Ser Phe Tyr Ala Ile Ser Trp
145 150 155 160

Val Arg Gln Ala Pro Gly Gln Gly Leu Glu Trp Met Gly Gly Phe Ile
165 170 175

Pro Ile Phe Gly Ala Ala Asn Tyr Ala Gln Lys Phe Gln Gly Arg Val
180 185 190

Thr Ile Thr Ala Asp Glu Ser Thr Ser Thr Ala Tyr Met Glu Leu Ser
195 200 205

-continued

```
Ser Leu Arg Ser Asp Asp Thr Ala Val Tyr Tyr Cys Ala Arg Ile Pro
    210                 215                 220

Ser Gly Ser Tyr Tyr Tyr Asp Tyr Asp Met Asp Val Trp Gly Gln Gly
225                 230                 235                 240

Thr Thr Val Thr Val Ser Ser
                245


<210> SEQ ID NO 82
<211> LENGTH: 297
<212> TYPE: DNA
<213> ORGANISM: Artificial sequence
<220> FEATURE:
<223> OTHER INFORMATION: B2M with synonymous mutation

<400> SEQUENCE: 82

atccagagga ccccgaagat ccaggtttat tctcggcatc ctgccgaaaa tggaaaaagc     60

aattttctca actgttatgt gtctggattt cacccatctg acatagaggt tgaccttctt    120

aagaatggcg agagaatcga gaaggtcgaa cattcagact tgagcttcag caaggattgg    180

agcttttatc ttctttatta tactgaattt actcccactg aaaaggatga atacgcctgc    240

agggtaaacc atgtaacact cagtcagcca aagatcgtaa aatgggaccg agacatg       297
```